United States Patent
Kantrowitz

(10) Patent No.: US 10,912,872 B2
(45) Date of Patent: Feb. 9, 2021

(54) CARDIAC ASSIST DEVICE

(71) Applicant: VIADERM LLC, Ann Arbor, MI (US)

(72) Inventor: Allen B. Kantrowitz, Miami, FL (US)

(73) Assignee: VIADERM LLC, Ann Arbor, MI (US)

( * ) Notice: Subject to any disclaimer, the term of this patent is extended or adjusted under 35 U.S.C. 154(b) by 315 days.

(21) Appl. No.: 15/745,610

(22) PCT Filed: Jul. 22, 2016

(86) PCT No.: PCT/US2016/043482
§ 371 (c)(1),
(2) Date: Jan. 17, 2018

(87) PCT Pub. No.: WO2017/015534
PCT Pub. Date: Jan. 26, 2017

(65) Prior Publication Data
US 2018/0207335 A1    Jul. 26, 2018

Related U.S. Application Data

(60) Provisional application No. 62/324,198, filed on Apr. 18, 2016, provisional application No. 62/195,685, filed on Jul. 22, 2015.

(51) Int. Cl.
*A61M 1/10* (2006.01)
*A61M 1/12* (2006.01)
(Continued)

(52) U.S. Cl.
CPC .......... *A61M 1/1008* (2014.02); *A61F 2/856* (2013.01); *A61M 1/1072* (2013.01);
(Continued)

(58) Field of Classification Search
CPC ........ A61M 1/10; A61M 1/12; A61M 1/1072; A61M 1/125; A61M 1/122; A61M 1/1001;
(Continued)

(56) References Cited

U.S. PATENT DOCUMENTS

| | | |
|---|---|---|
| 4,051,840 A | 10/1977 | Kantrowitz et al. |
| 4,630,597 A | 12/1986 | Kantrowitz et al. |
| (Continued) | | |

FOREIGN PATENT DOCUMENTS

| | | |
|---|---|---|
| WO | 2000045872 A2 | 8/2000 |
| WO | 2014052894 A2 | 4/2014 |

OTHER PUBLICATIONS

Huang, D. et al., "Optical Coherence Tomography", Science, Nov. 22, 1991, pp. 1178-1181, vol. 254, Issue 5035, Author Manuscript, Available in PMC Nov. 9, 2015, 12 pages; https://www.ncbi.nlm.nih.gov/pmc/articles/PMC4638169/pdf/nihms692532.pdf.

(Continued)

*Primary Examiner* — Jon Eric C Morales
(74) *Attorney, Agent, or Firm* — Blue Filament Law PLLC

(57) ABSTRACT

A cardiac pump and an assist system is provided that increases blood ejection from a compromised heart. An implantable cardiac pump acting as an assist device provided includes an attachment system and locating features that enable a minimally invasive procedure to implant and deploy one or more aortic blood pumps in a patient. The insertable cardiac pump is replaceable without resort to a conventional open surgical procedure. Monitoring of cardiac pump operation allows for replacement in advance of chamber failure. The dynamics of blood-contacting interface of the cardiac assist device mimic the dynamics of the blood-contacting interface of a naturally occurring left ventricle, thereby minimizing flow-related device-associated pathologic disturbances of intravascular clotting mechanisms. A process of operating a cardiac assist device includes cyclically inflating and deflating one or more inflatable cardiac pumping chambers with timing and parameters as to pres- (Continued)

sure, deflection, and speed of inflation to in crease patient cardiac output.

18 Claims, 52 Drawing Sheets

(51) Int. Cl.
*A61F 2/856* (2013.01)
*A61F 2/915* (2013.01)

(52) U.S. Cl.
CPC .......... *A61M 1/1086* (2013.01); *A61M 1/122* (2014.02); *A61M 1/125* (2014.02); *A61M 1/127* (2013.01); *A61F 2/915* (2013.01); *A61M 1/106* (2013.01); *A61M 2205/3306* (2013.01); *A61M 2205/3317* (2013.01); *A61M 2205/3375* (2013.01); *A61M 2230/20* (2013.01)

(58) Field of Classification Search
CPC .. A61M 25/10; A61M 25/1011; A61B 5/0215
USPC .......................................................... 600/18
See application file for complete search history.

(56) References Cited

U.S. PATENT DOCUMENTS

| | | | |
|---|---|---|---|
| 4,634,422 A | 1/1987 | Kantrowitz et al. | |
| 5,242,415 A | 9/1993 | Kantrowitz et al. | |
| 5,599,329 A | 2/1997 | Gabbay | |
| 5,827,171 A | 10/1998 | Dobak, III et al. | |
| 5,833,619 A | 11/1998 | Freed et al. | |
| 5,833,655 A | 11/1998 | Freed et al. | |
| 5,904,666 A | 5/1999 | DeDecker et al. | |
| 6,132,363 A | 10/2000 | Freed et al. | |
| 6,228,018 B1 | 5/2001 | Downey et al. | |
| 6,471,633 B1 | 10/2002 | Freed | |
| 6,511,412 B1 | 1/2003 | Freed et al. | |
| 6,733,459 B1 | 5/2004 | Atsumi | |
| 7,374,531 B1 | 5/2008 | Kantrowitz | |
| 7,766,814 B2 | 8/2010 | Walsh | |
| 7,846,083 B2 | 12/2010 | Smith et al. | |
| 7,976,452 B2 | 7/2011 | Kantrowitz | |
| 8,293,284 B2 | 10/2012 | Baldassarre et al. | |
| 8,323,174 B2 | 12/2012 | Jeevanandam et al. | |
| 8,608,637 B2 | 12/2013 | Jeevanandam et al. | |
| 8,684,905 B2 | 4/2014 | Jeevanandam et al. | |
| 2001/0031907 A1 | 10/2001 | Downey | |
| 2003/0083539 A1 | 5/2003 | Leschinsky | |
| 2004/0097784 A1 | 5/2004 | Peters et al. | |
| 2008/0281147 A1 | 11/2008 | Kantrowitz | |
| 2009/0131741 A1 | 5/2009 | Kantrowitz | |
| 2010/0211008 A1 | 8/2010 | Wiest | |
| 2012/0108886 A1 | 5/2012 | Jeevanandam et al. | |
| 2012/0116439 A1 | 5/2012 | Ho | |
| 2012/0179184 A1 | 7/2012 | Orlov | |
| 2012/0308406 A1 | 12/2012 | Schumacher | |
| 2013/0184515 A1 | 7/2013 | Ovil et al. | |
| 2013/0331639 A1 | 12/2013 | Campbell et al. | |
| 2014/0088340 A1 | 3/2014 | Kantrowitz et al. | |
| 2014/0135567 A1 | 5/2014 | Marotta | |
| 2014/0316189 A1 | 10/2014 | Spence et al. | |
| 2015/0018600 A1 | 1/2015 | Zilbershlag | |

OTHER PUBLICATIONS

Raman, Jai et al., "Subclavian Artery Access for Ambulatory Balloon Pump Insertion", The Annals of Thoracic Surgery, Sep. 2010, pp. 1032-1034, vol. 90, Issue 3, © 2010 by The Society of Thoracic Surgeons; DOI: 10.1016/j.athoracsur.2009.11.082; https://www.annalsthoracicsurgery.org/article/S0003-4975(09)02426-6/pdf.

Tsai, T-H et al., "Ultrahigh speed endoscopic optical coherence tomography using micromotor imaging catheter and VCSEL technology", Biomedical Optics Express, Jun. 14, 2013, pp. 1119-1132, vol. 4, Issue 7, © 2013 Optical Society of America; DOI:10.1364/BOE.4.001119; https://www.ncbi.nlm.nih.gov/pmc/articles/PMC3704093/pdf/1119.pdf.

Kirklin, J.K. et al., "Sixth INTERMACS annual report: A 10,000-patient database", The Journal of Heart and Lung Transplantation, Jun. 2014, pp. 555-564, vol. 33, Issue 6, © 2014 International Society for Heart and Lung Transplantation; DOI: 10.1016/j.healun.2014.04.010; https://www.jhltonline.org/article/S1053-2498(14)01093-6/fulltext.

International Search Report dated Oct. 12, 2016 for International Application No. PCT/US2016/043482 filed Jul. 22, 2016.

2nd Examination Report issued in corresponding Australian Appln. No. 2016297622, dated Apr. 3, 2020.

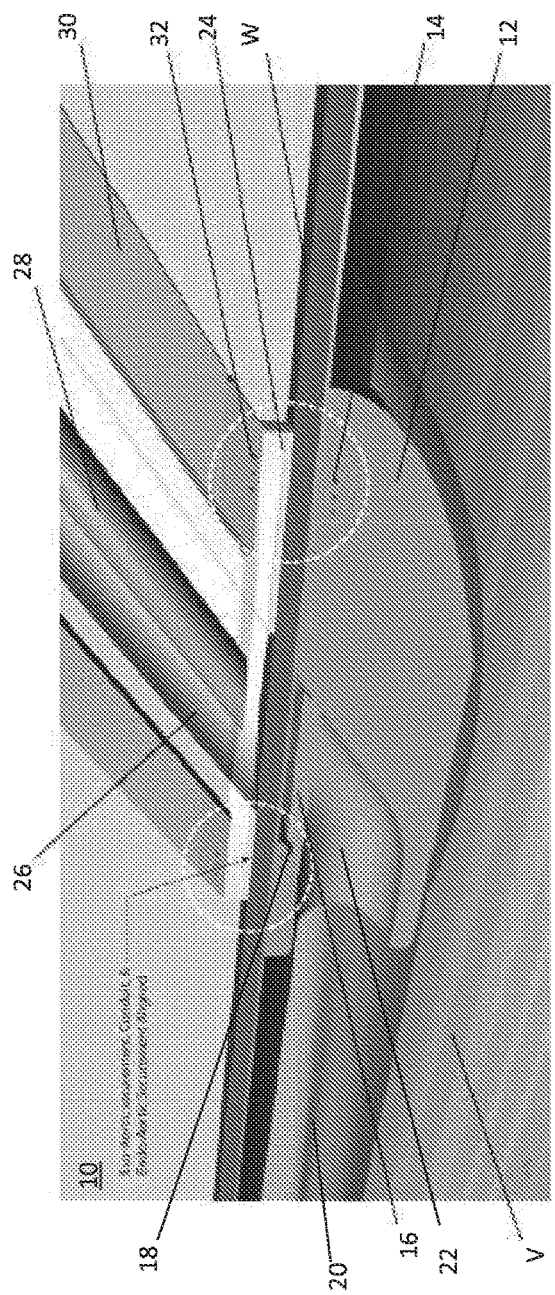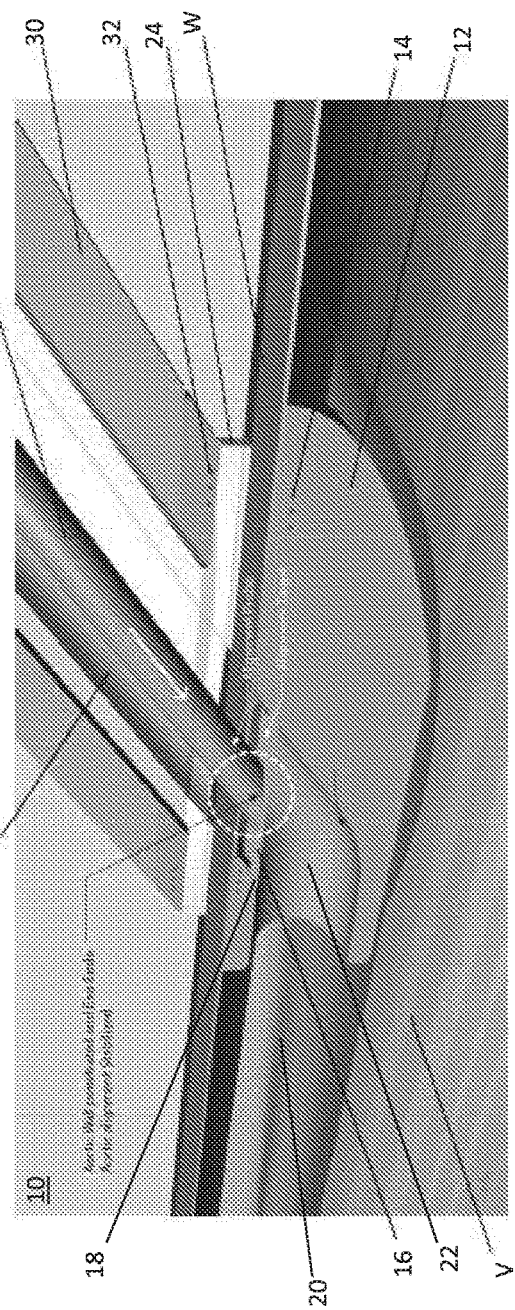
FIG. 1C
FIG. 1D

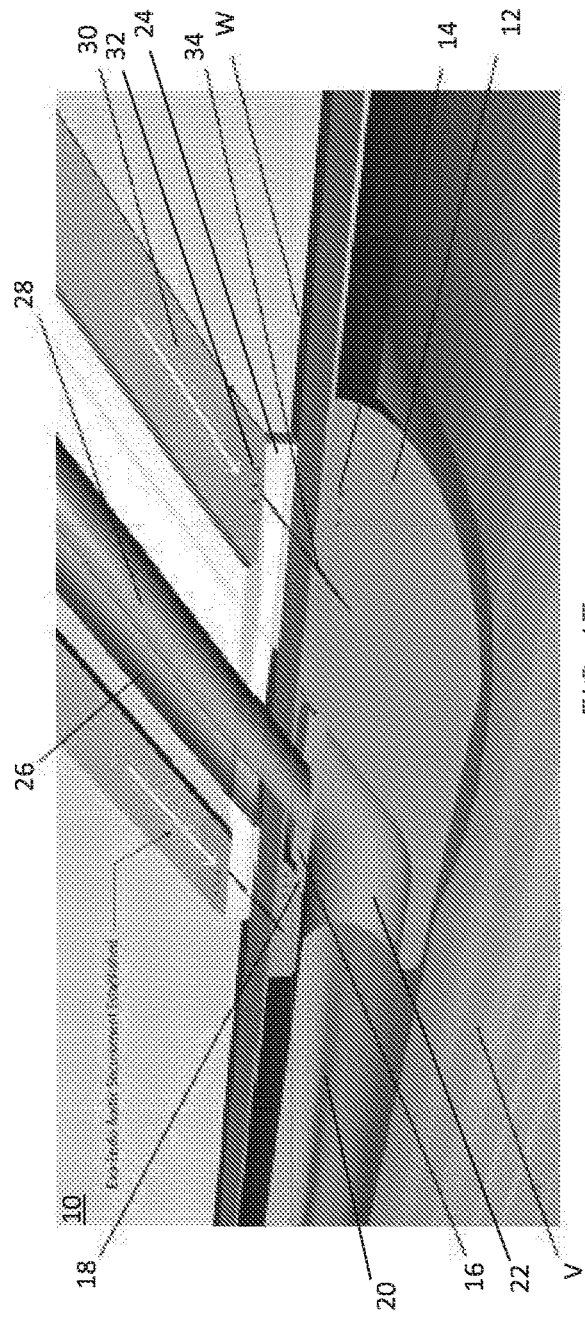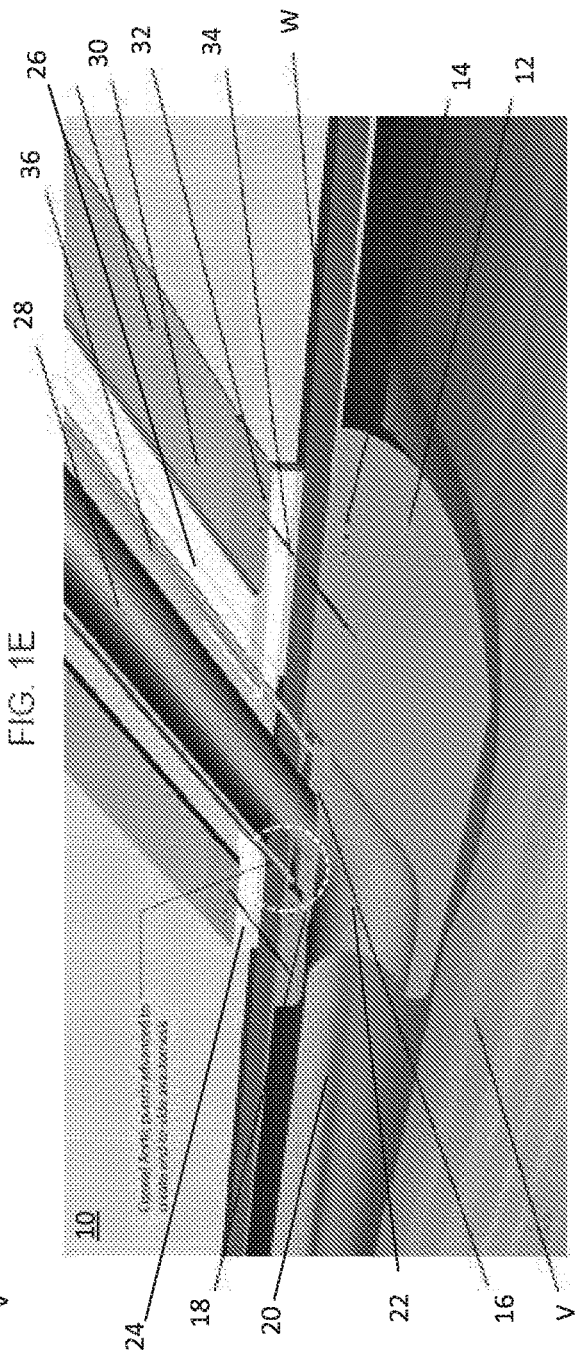

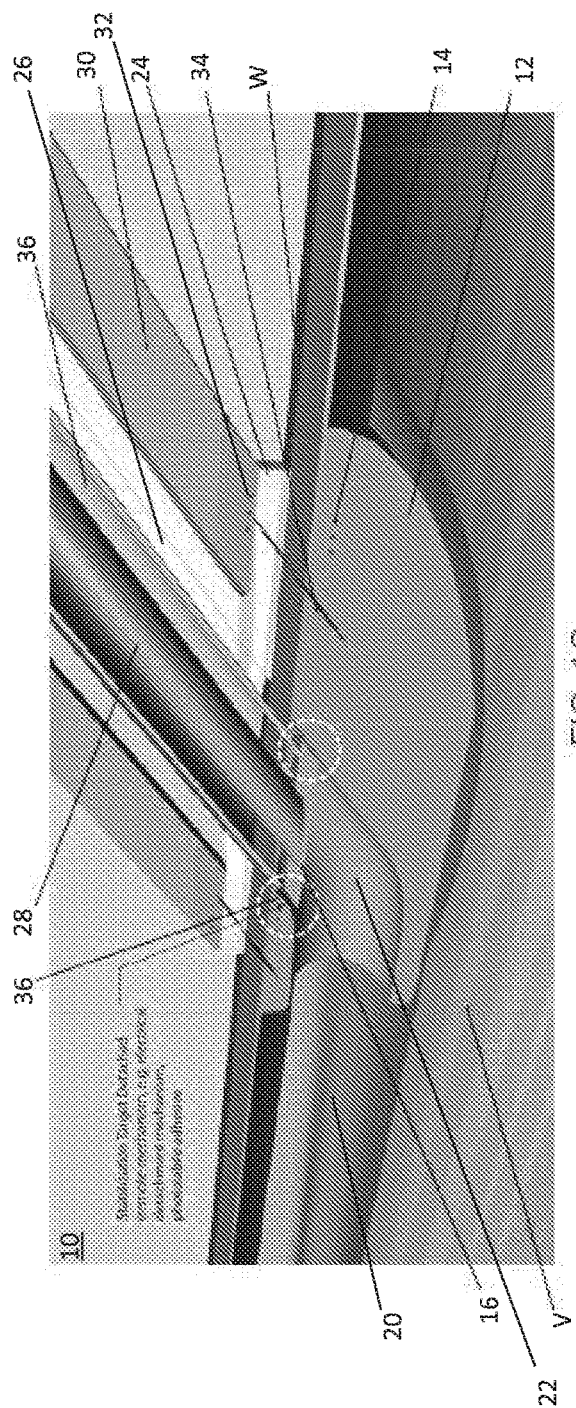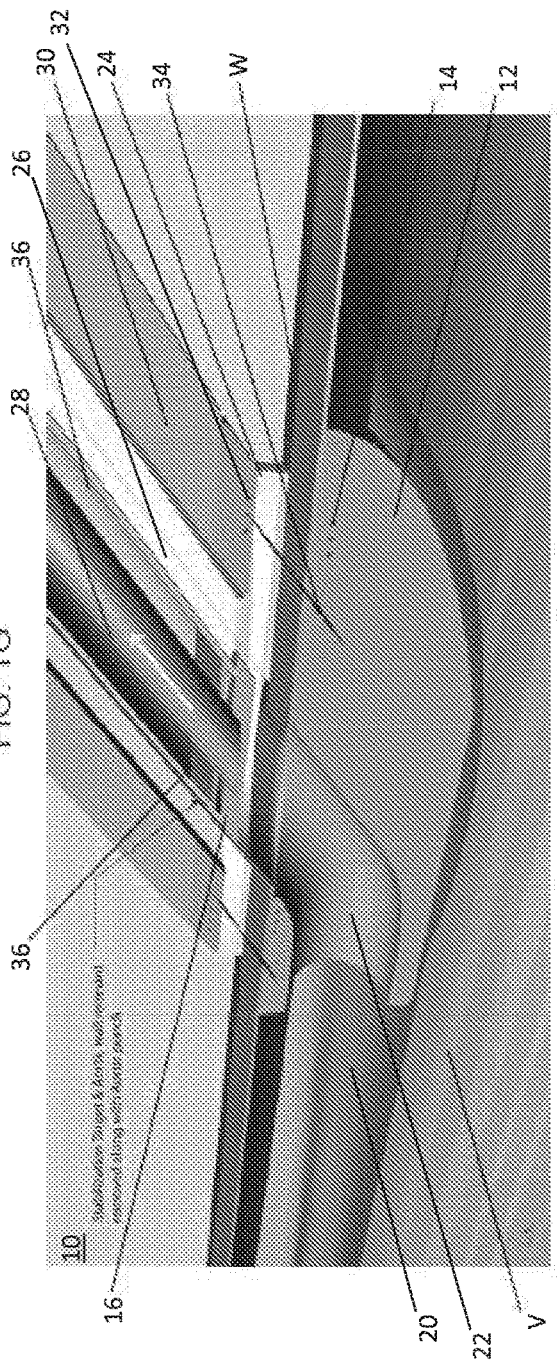

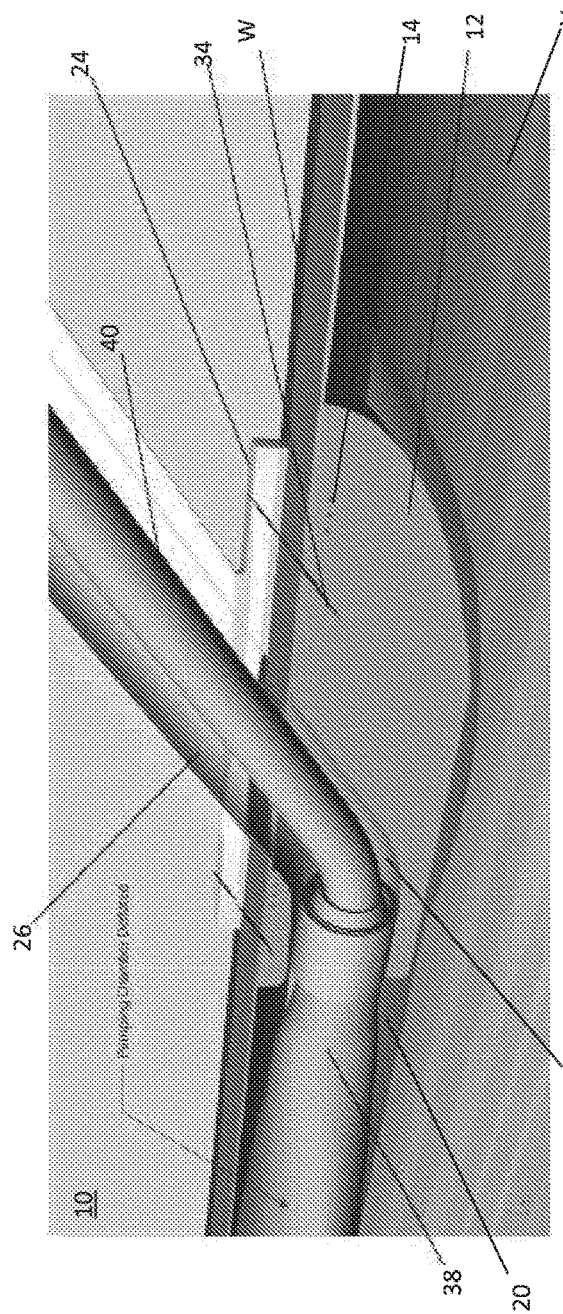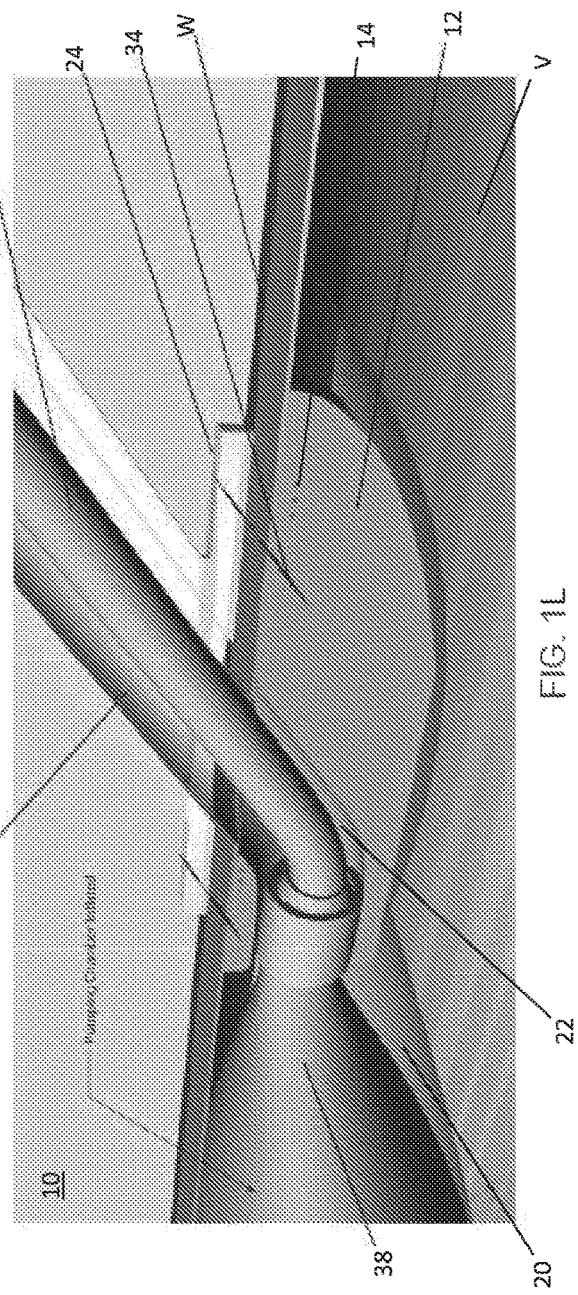

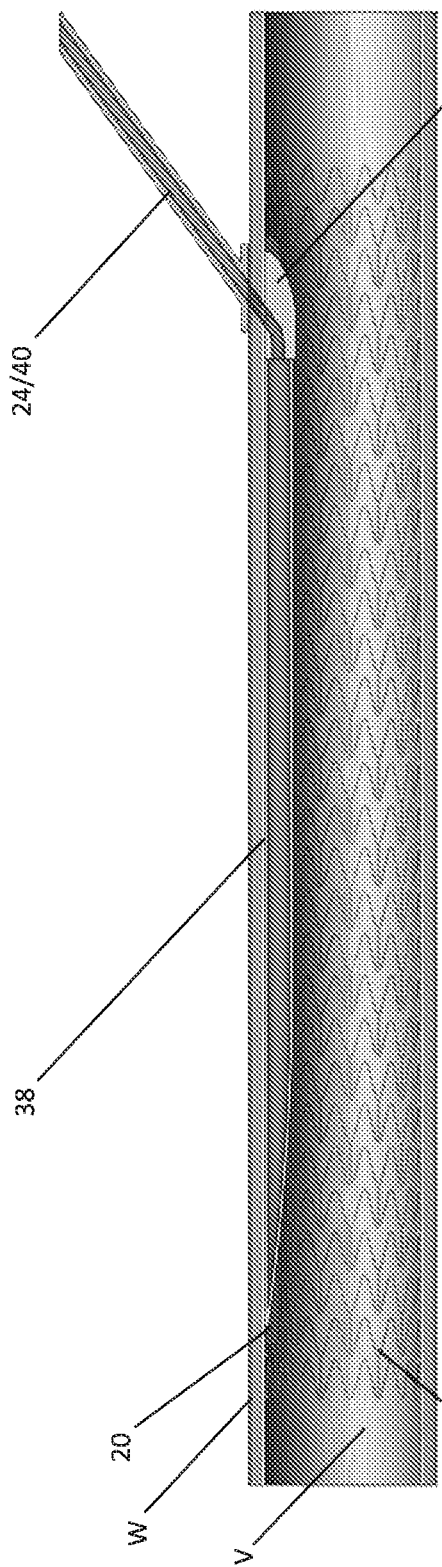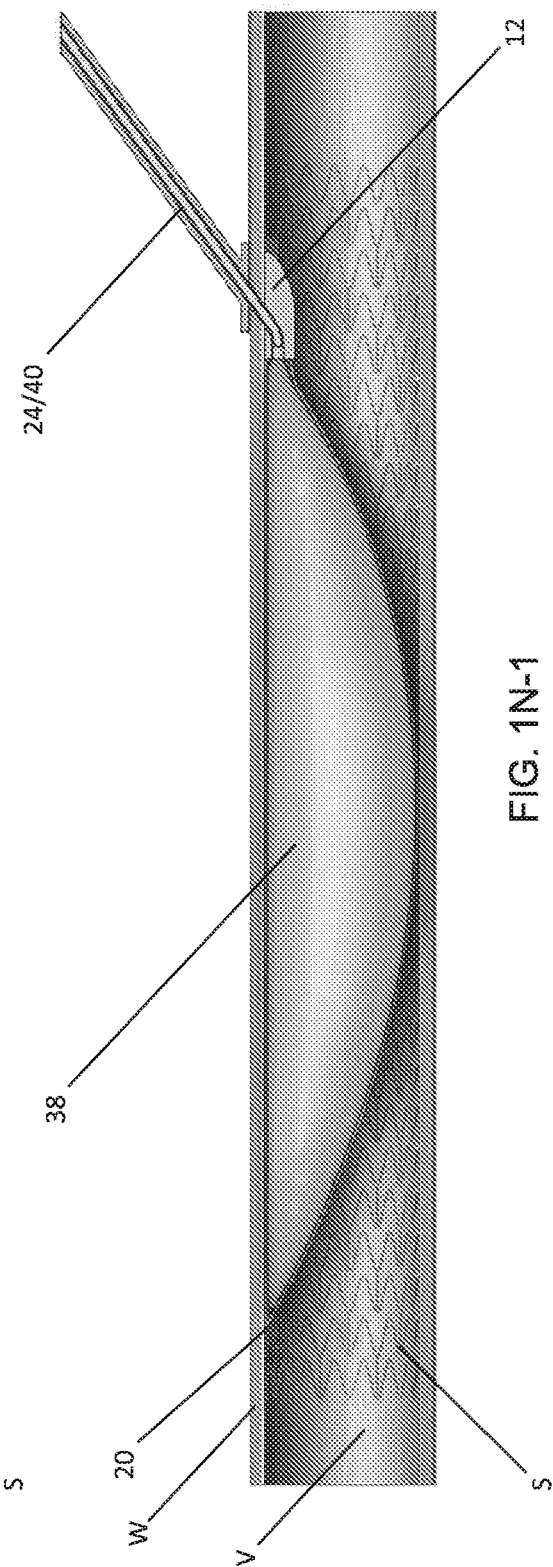

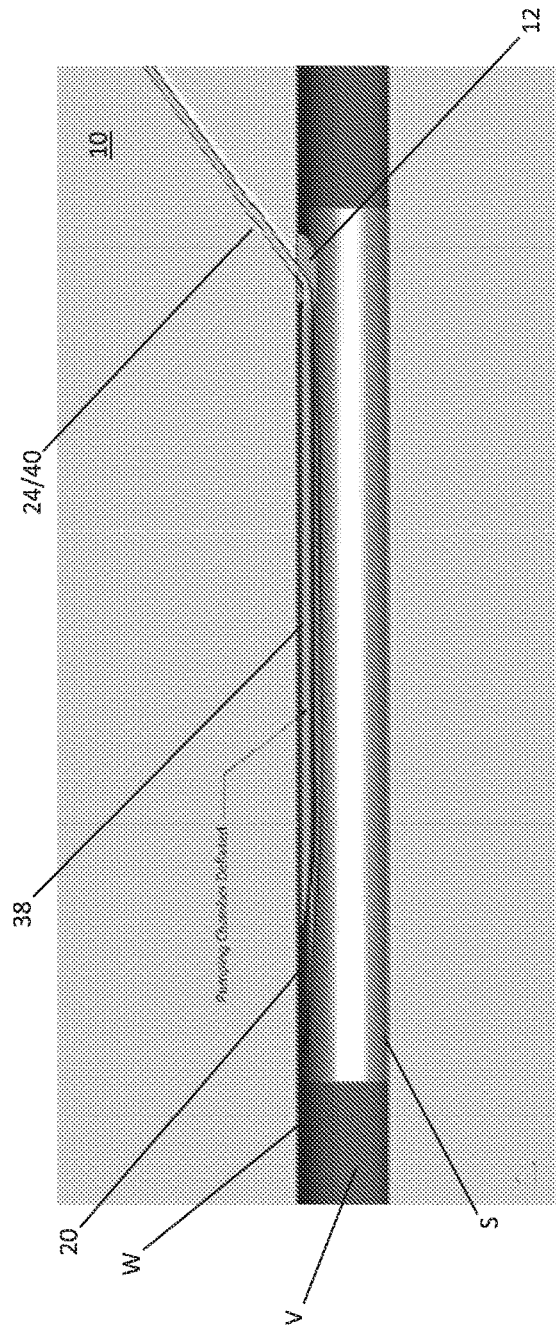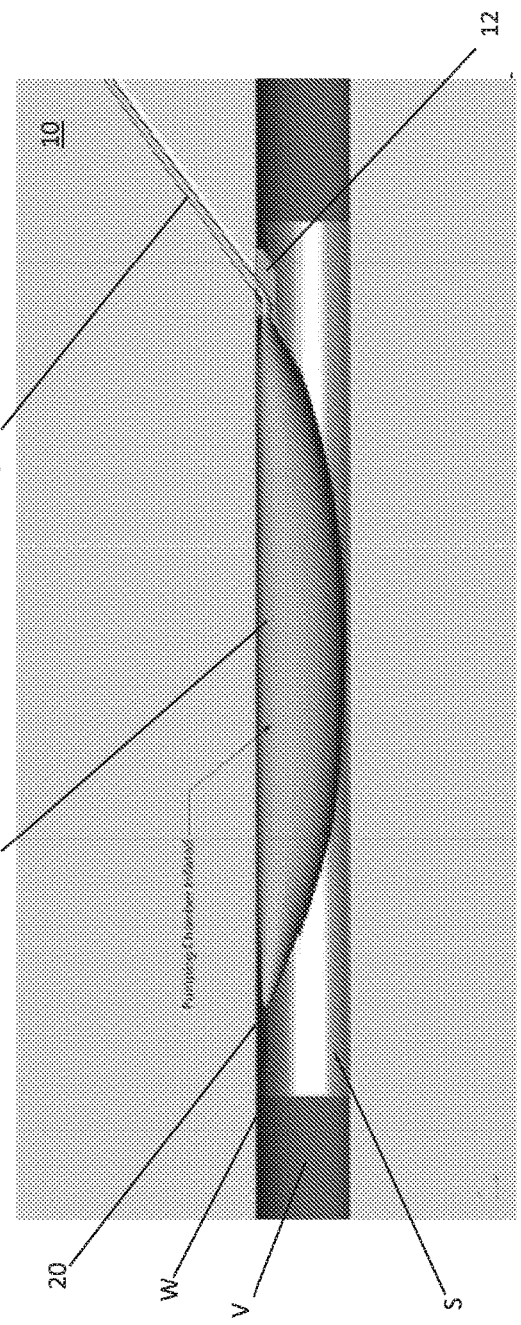

FIG. 3A-2 (Detail A)

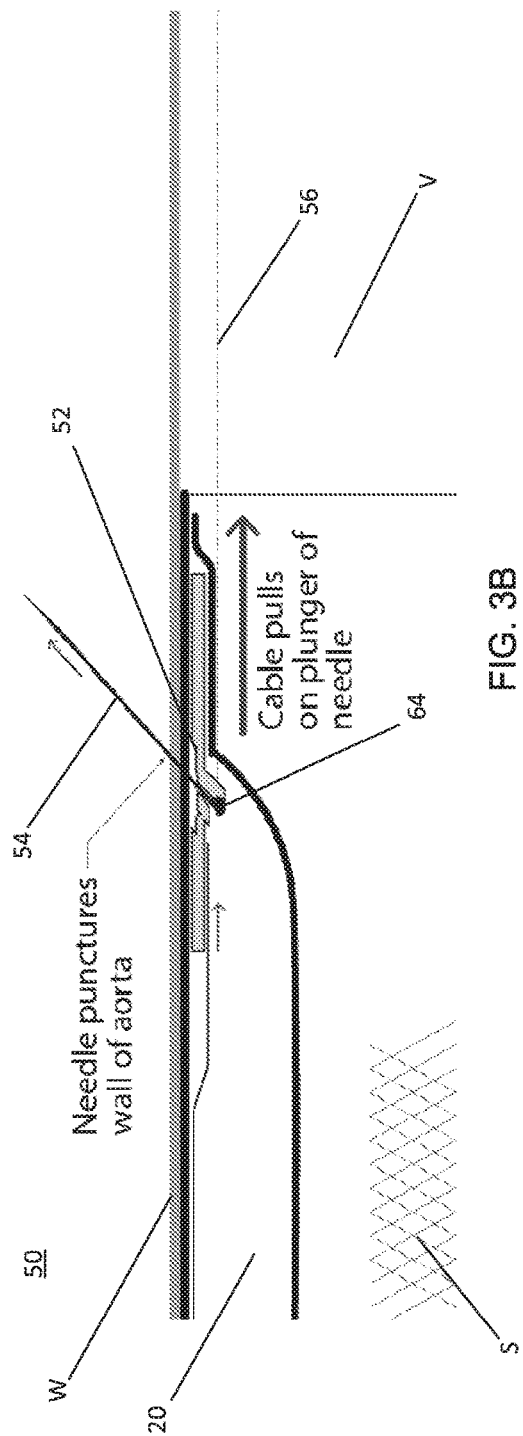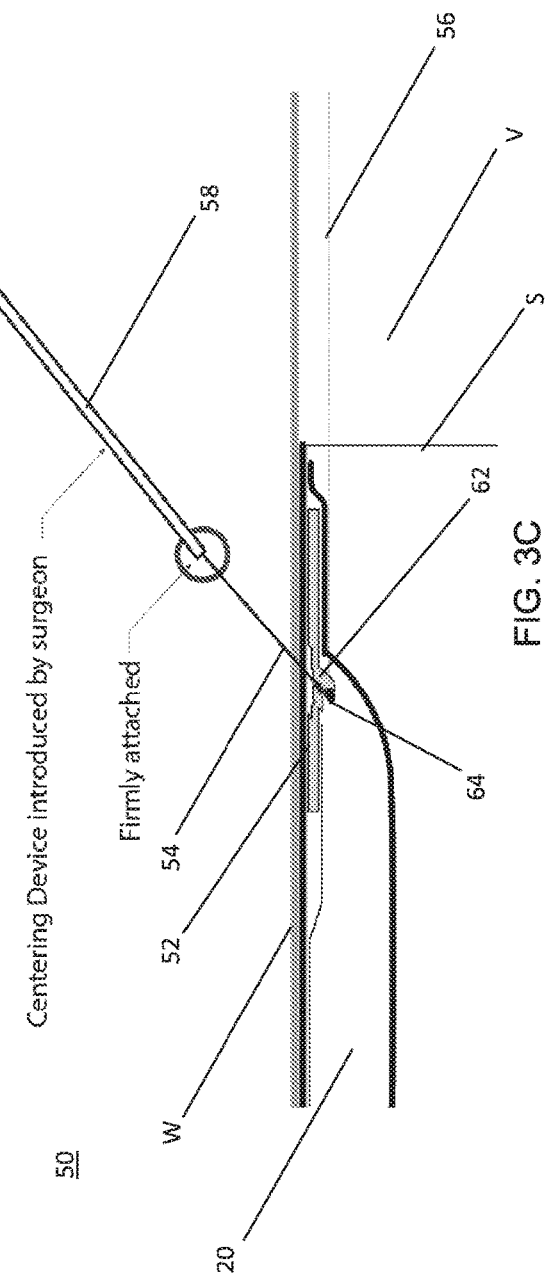

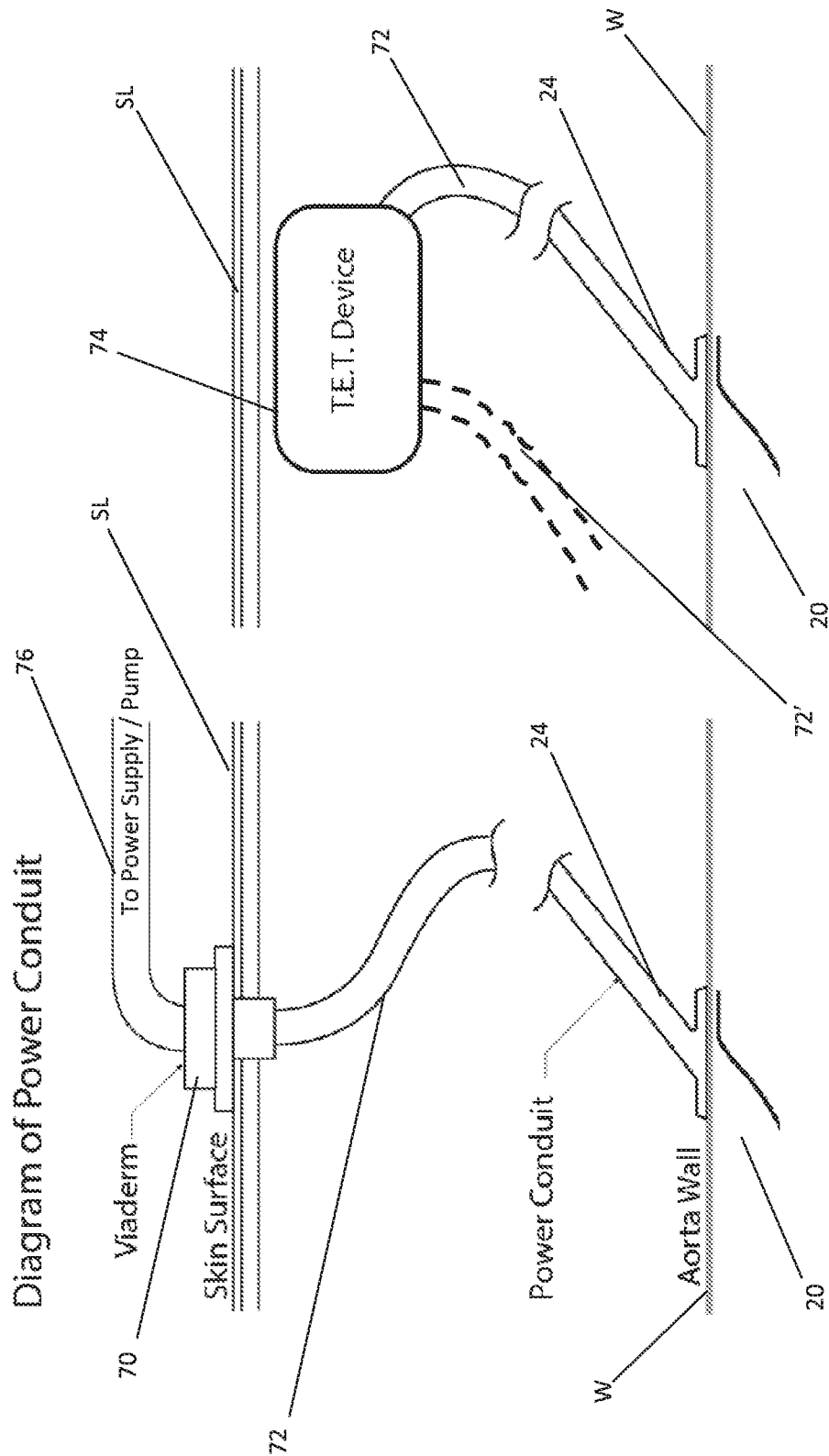

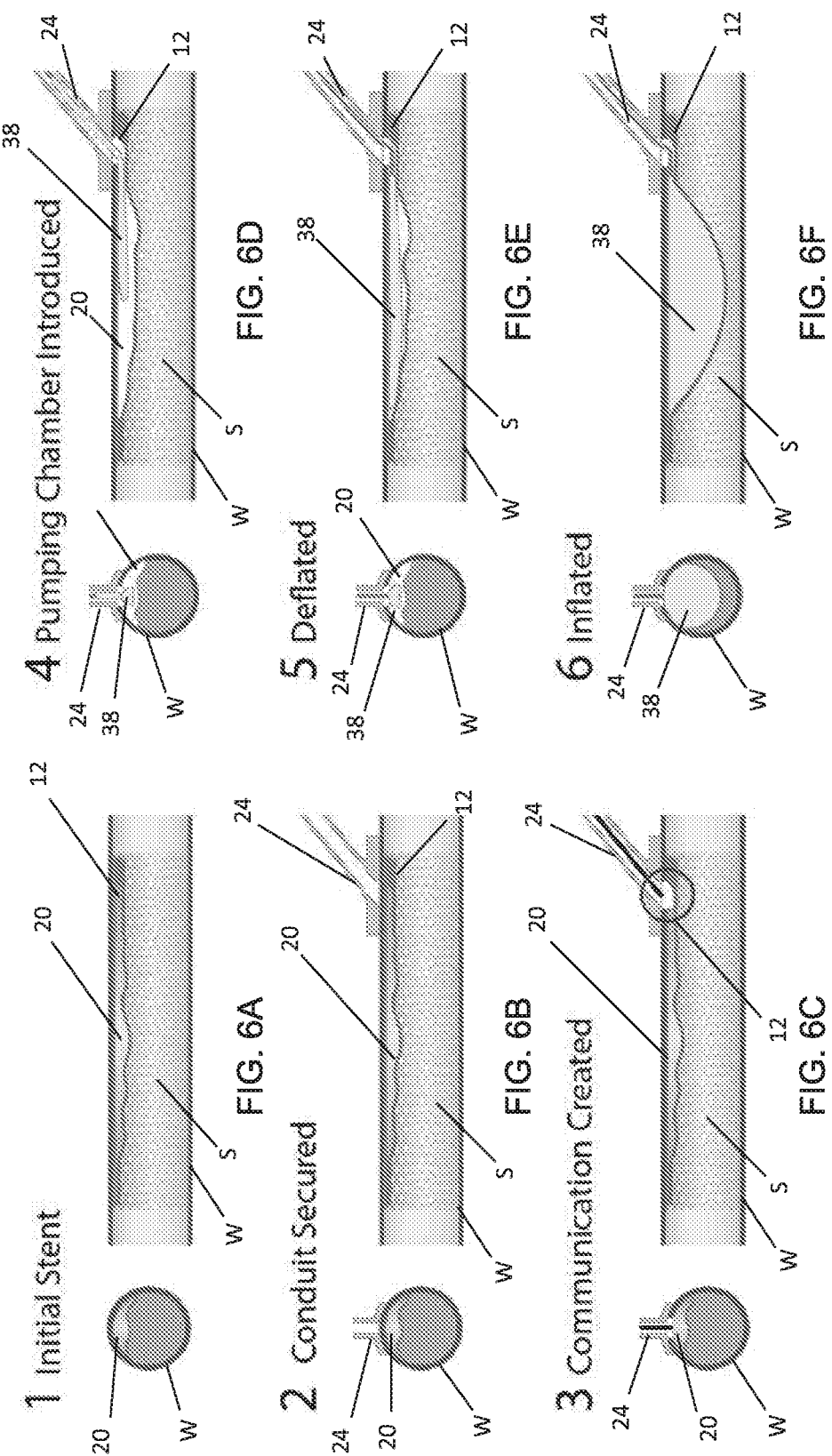

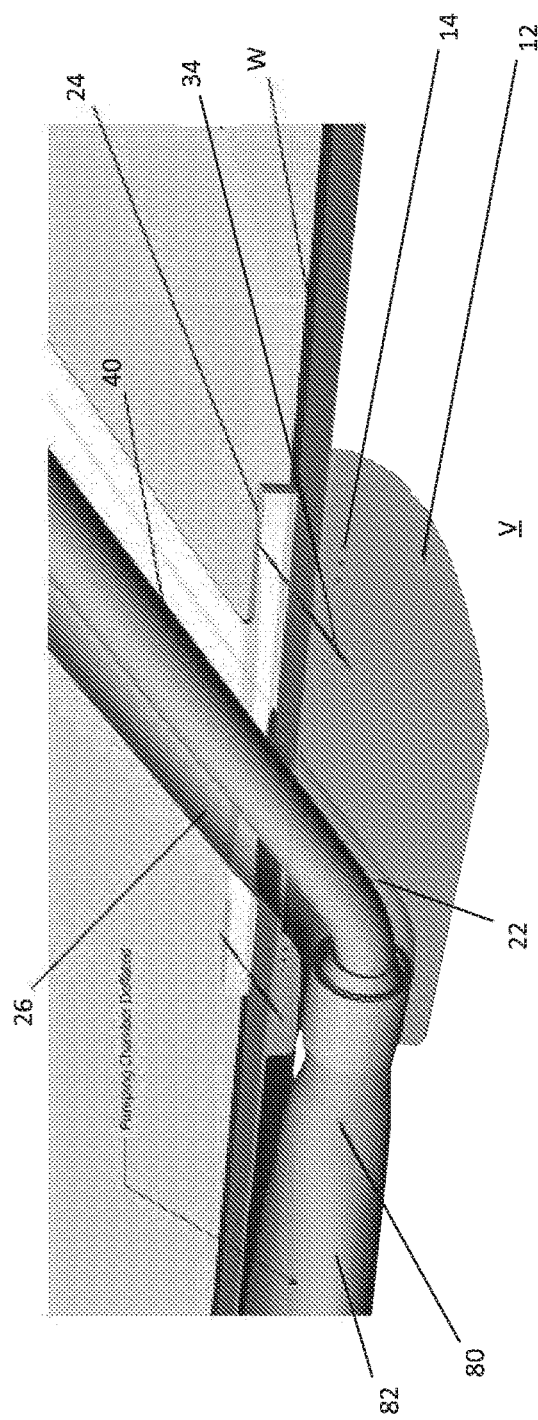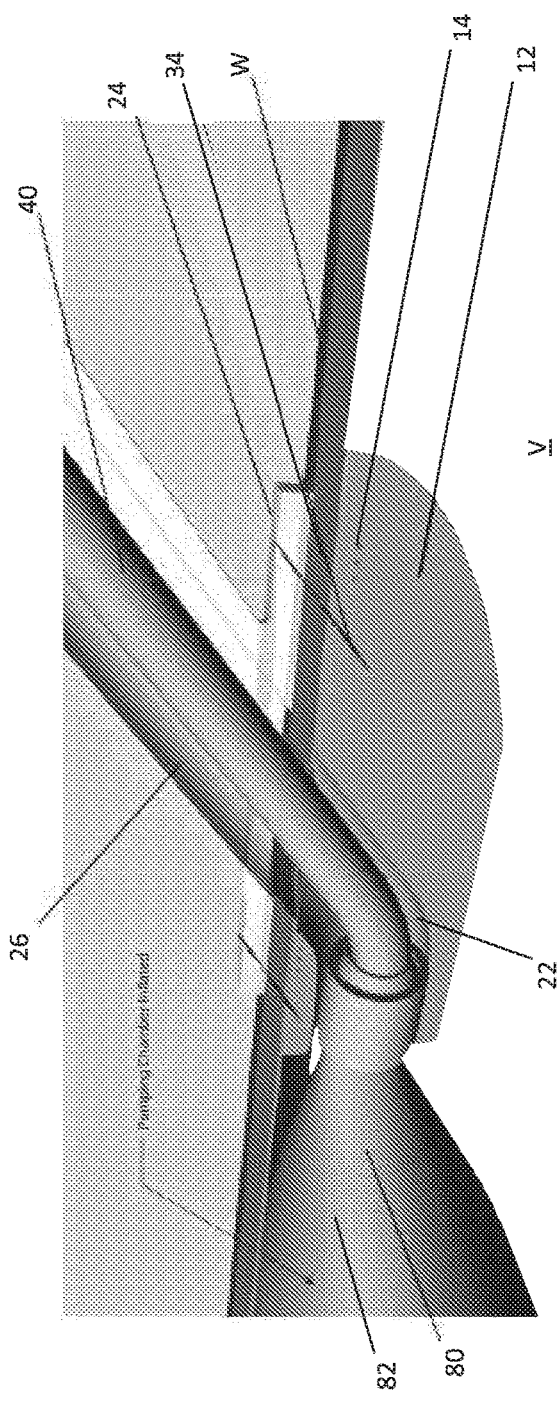

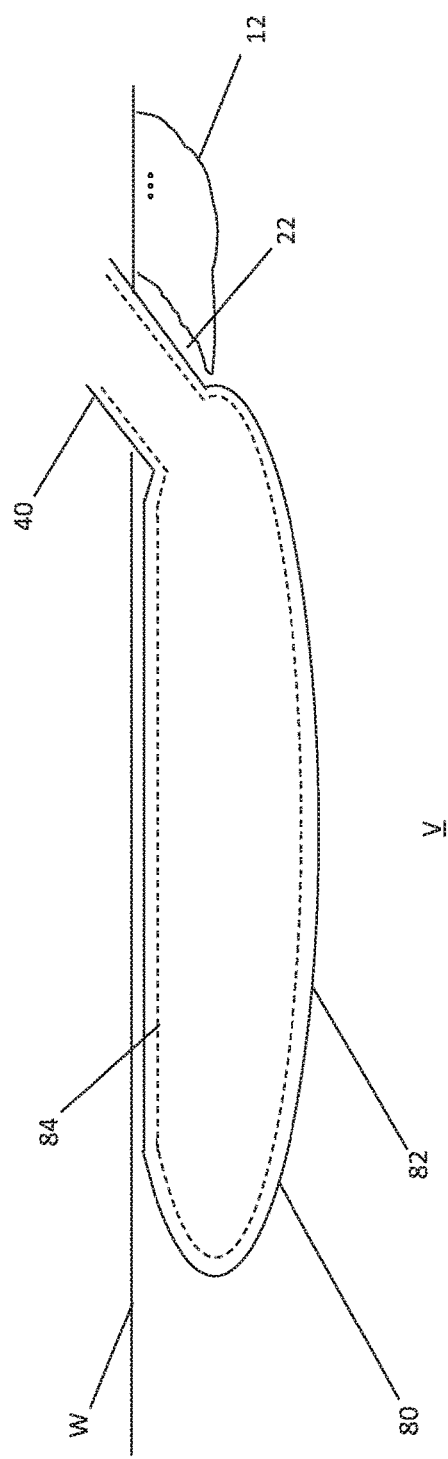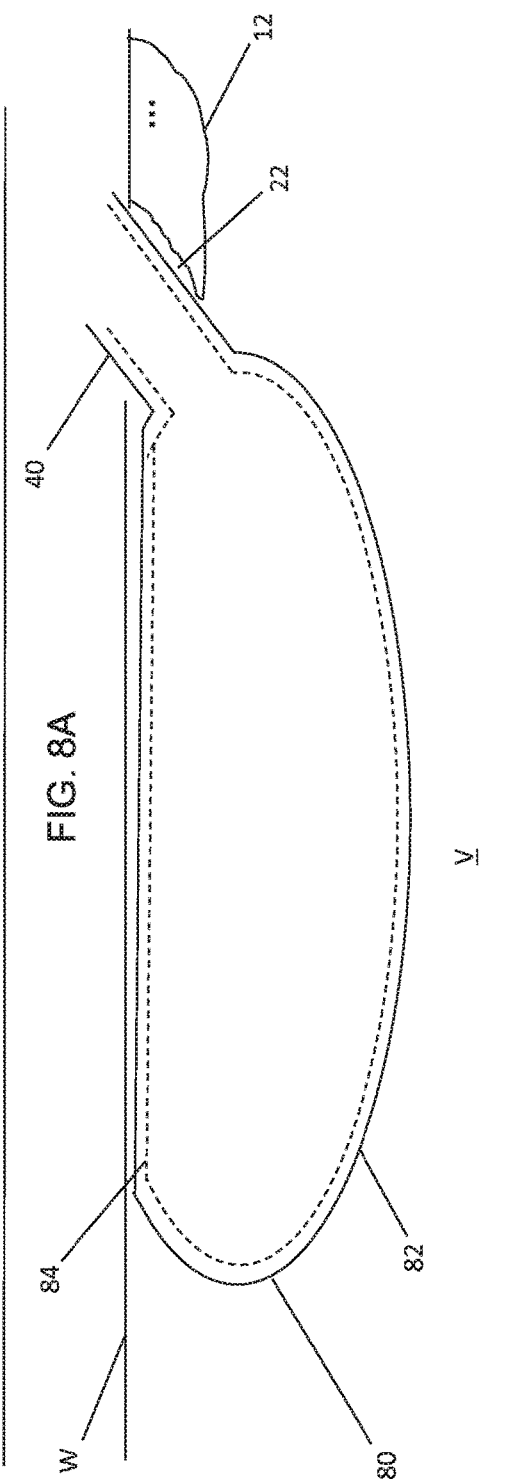

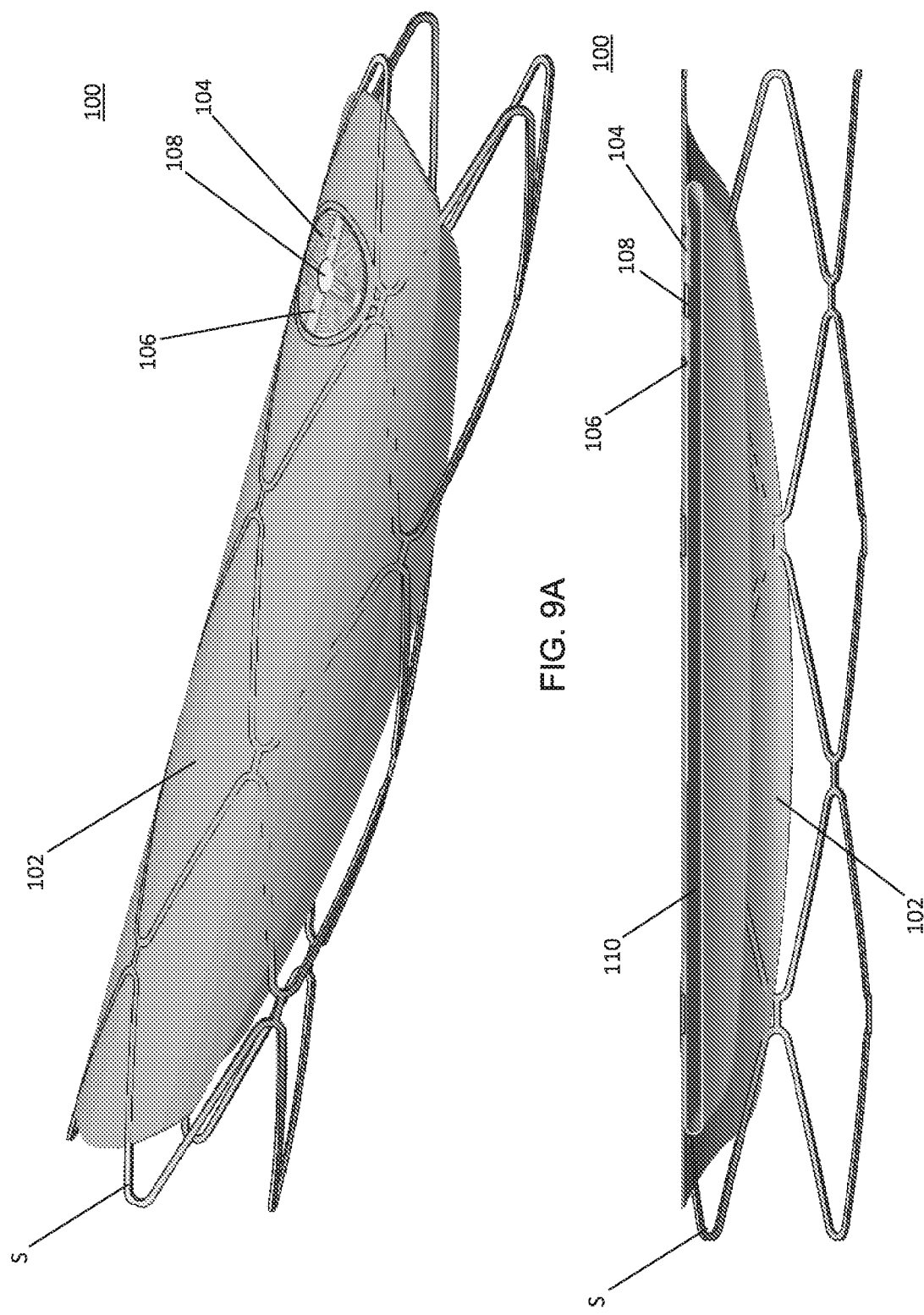

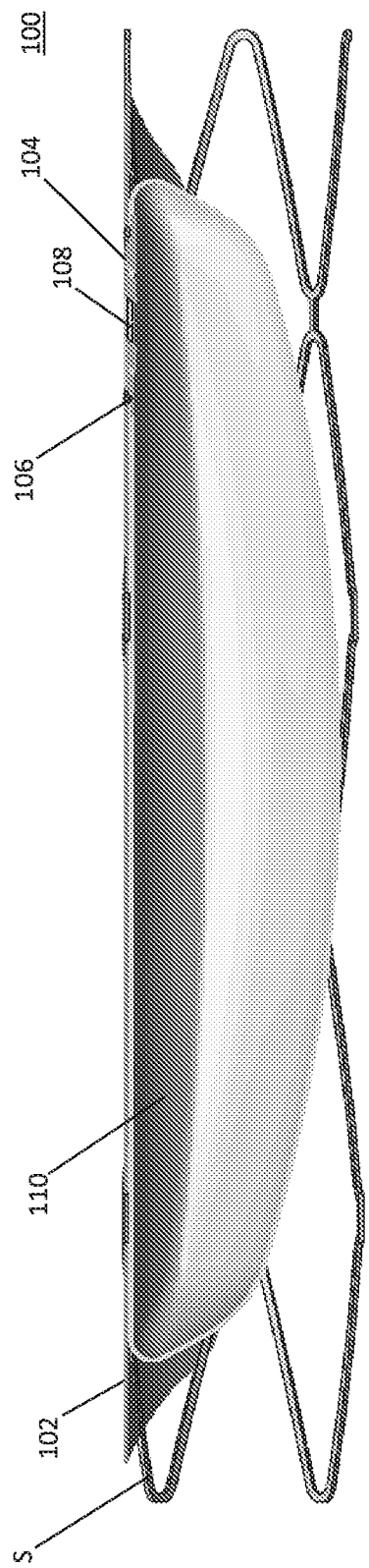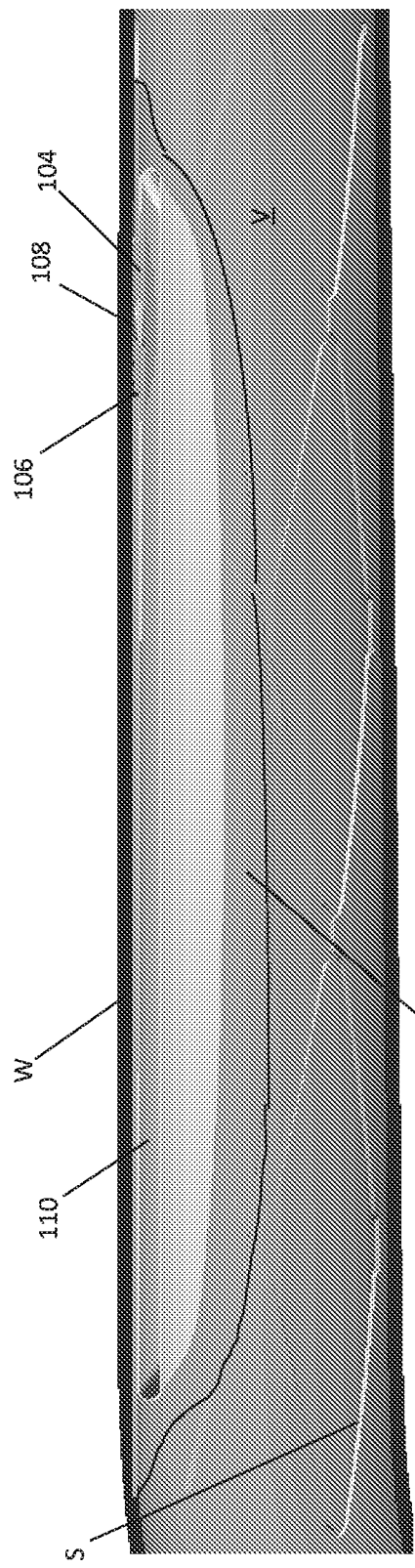
FIG. 9C
FIG. 9D

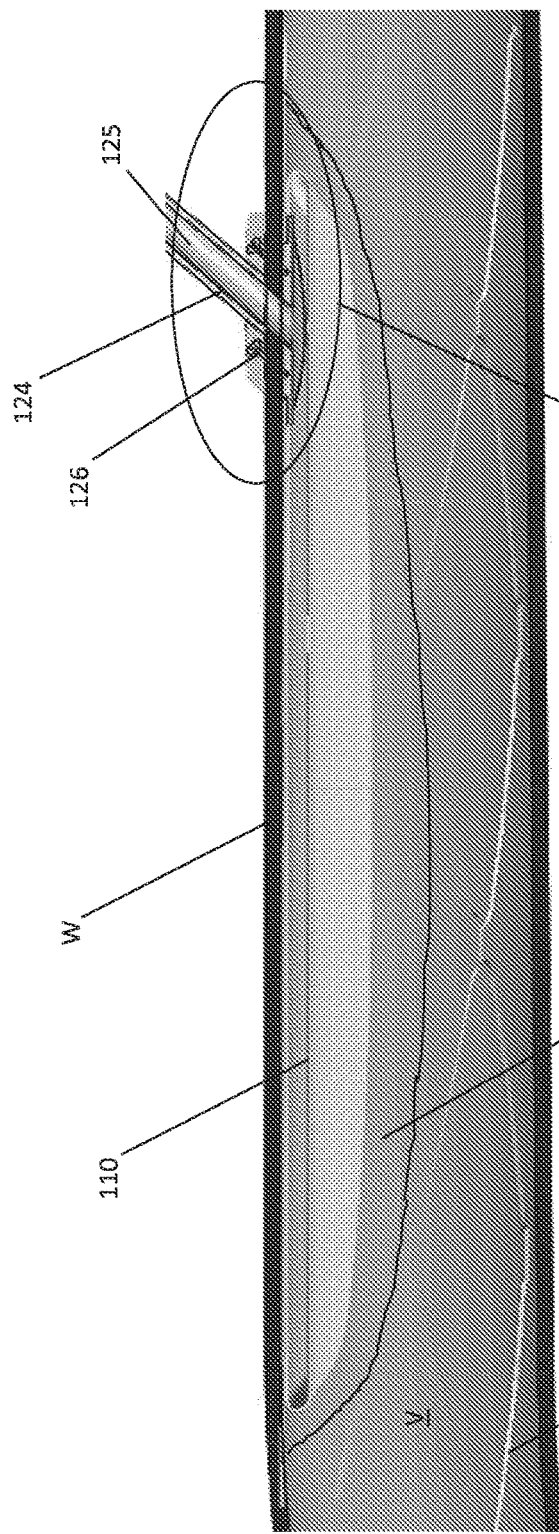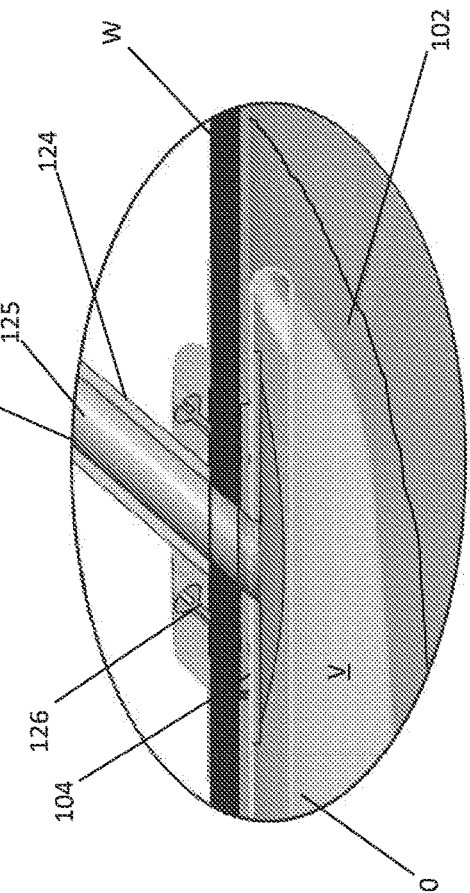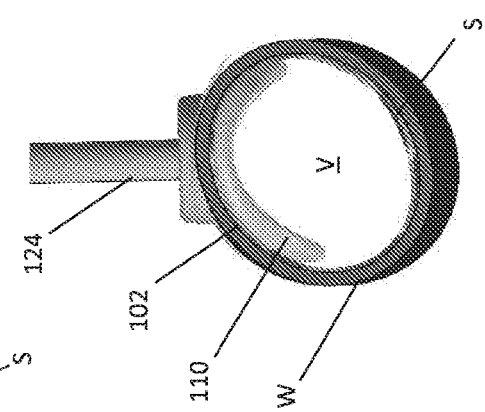

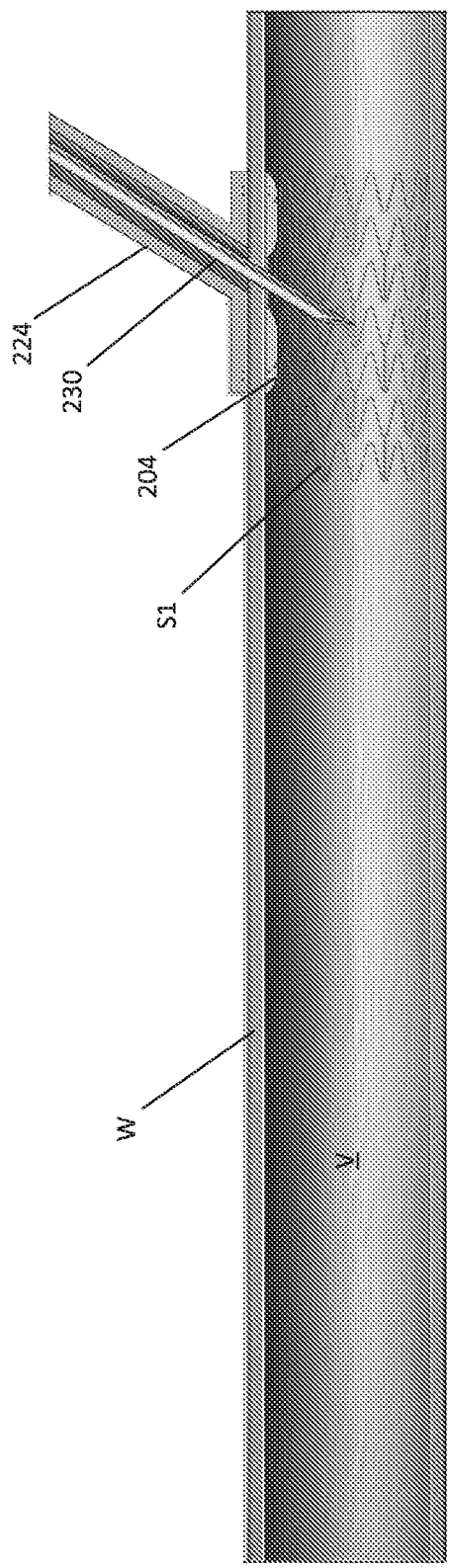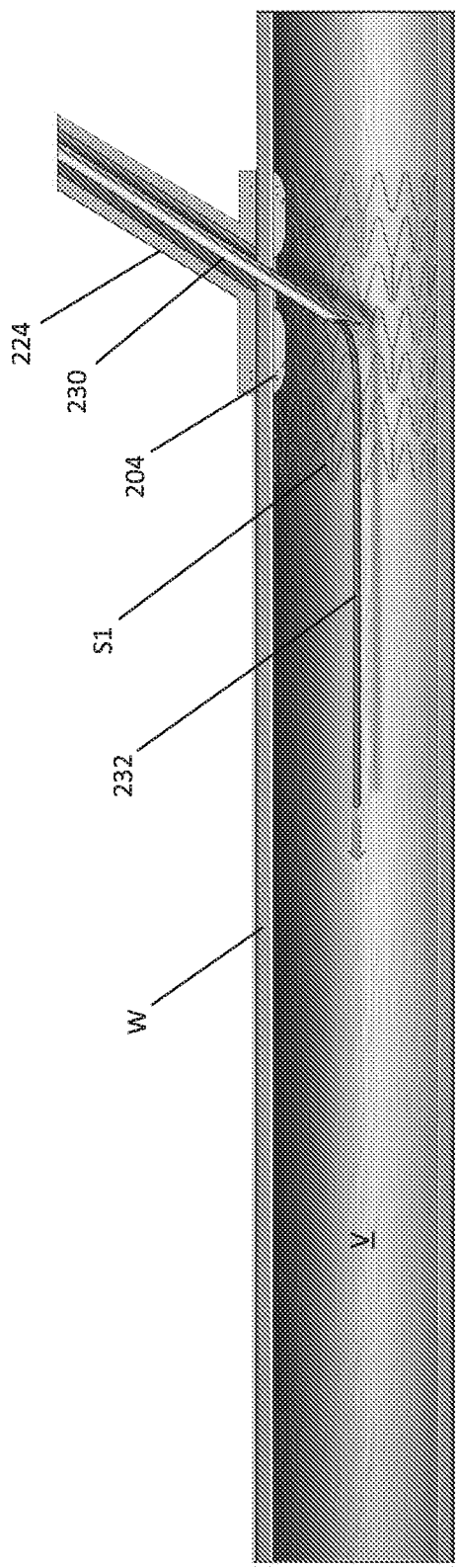

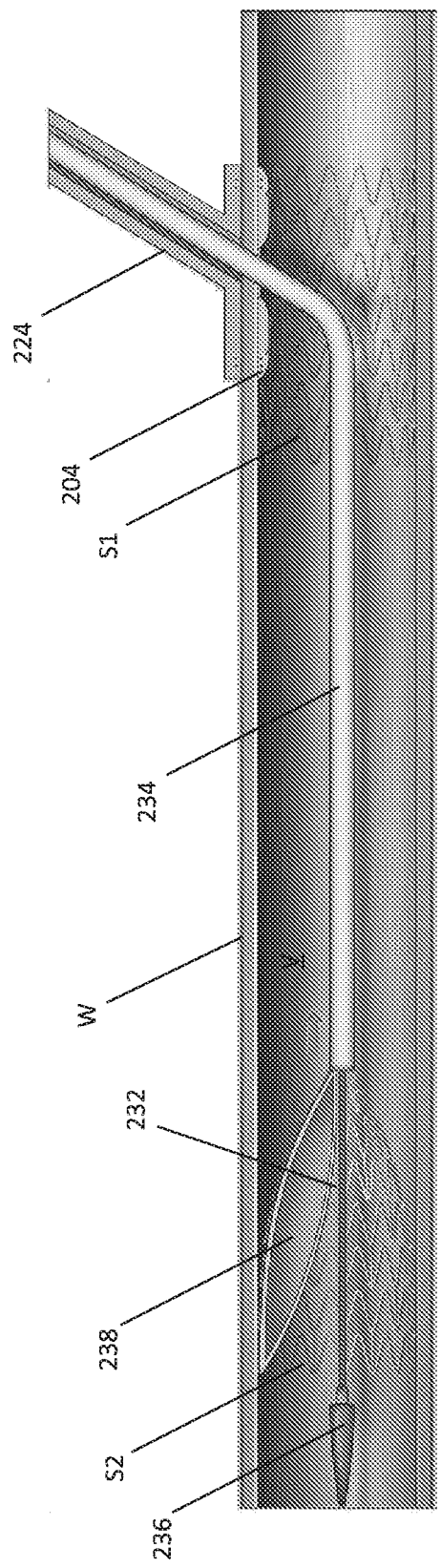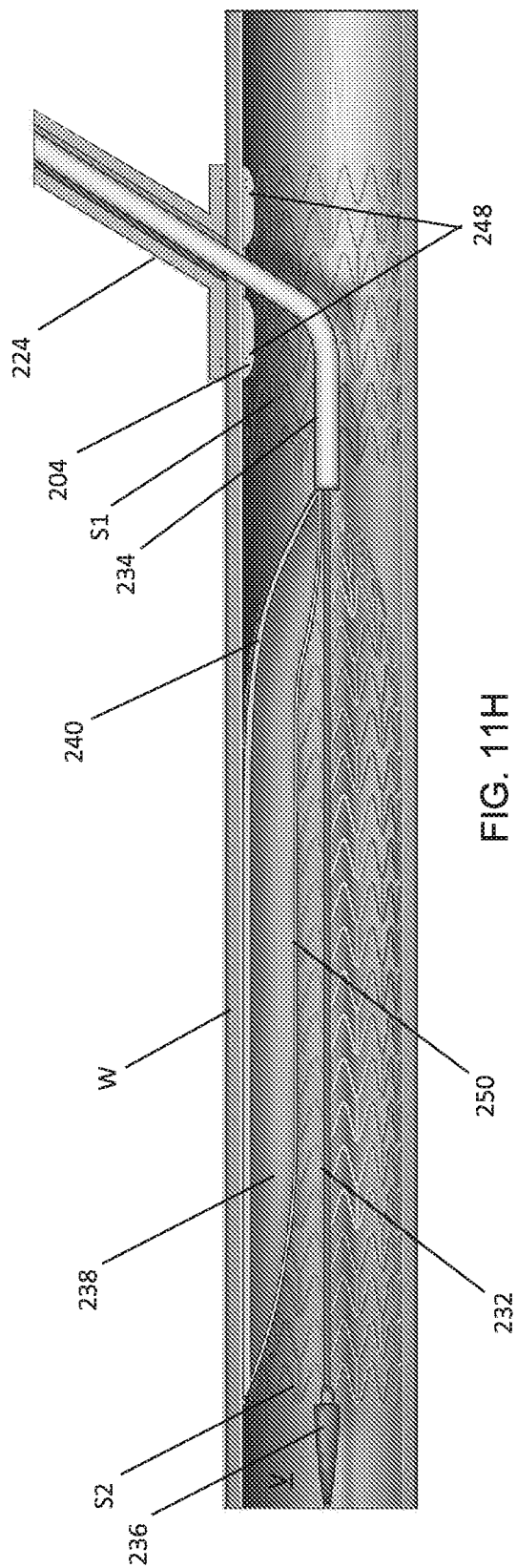
FIG. 11G
FIG. 11H

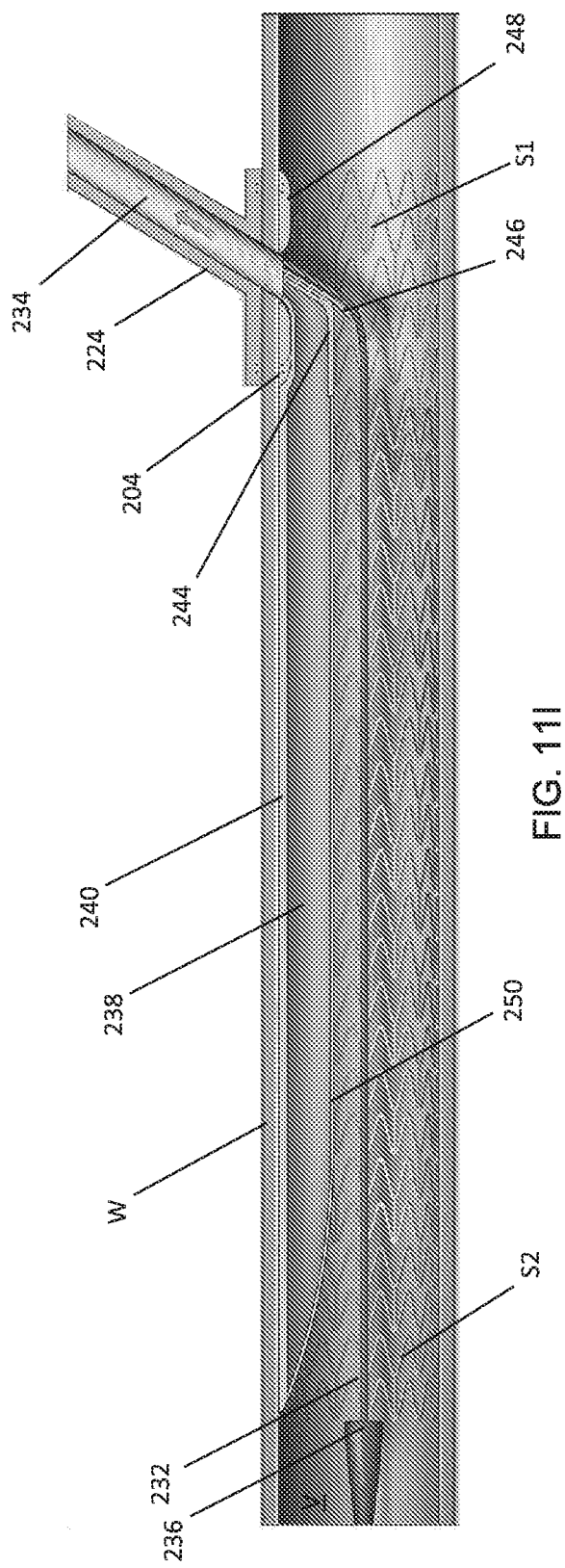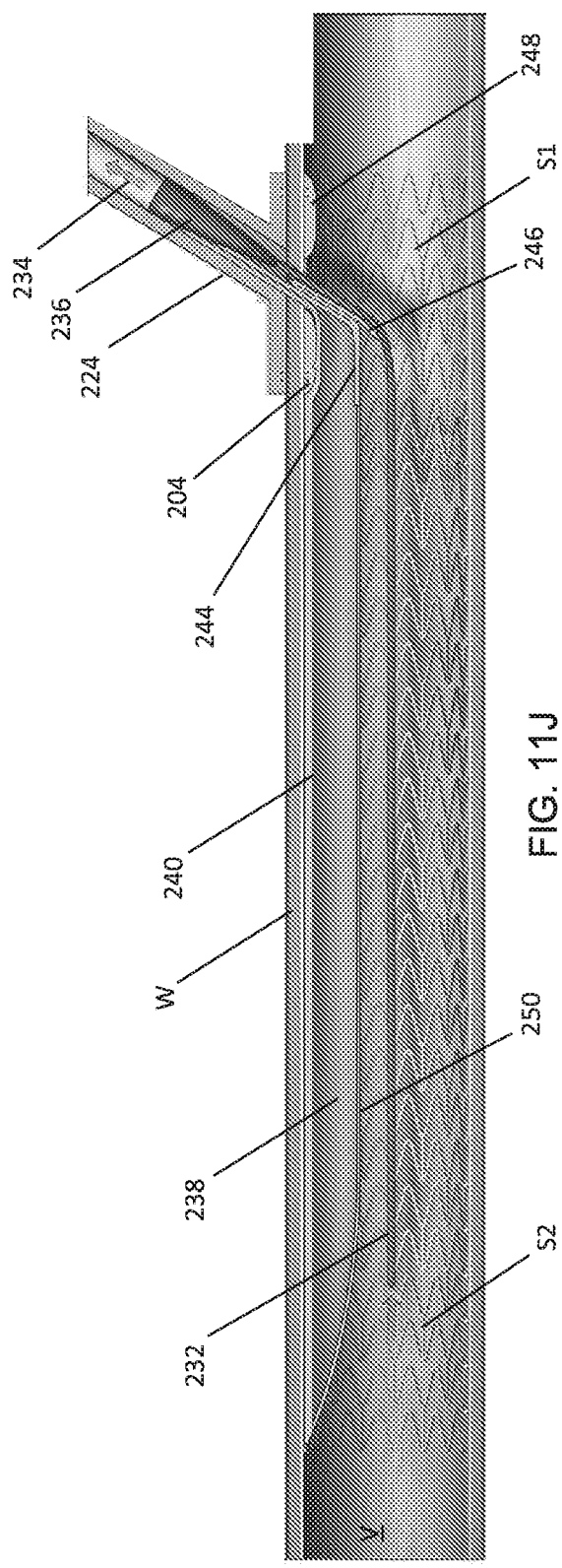
FIG. 11I
FIG. 11J

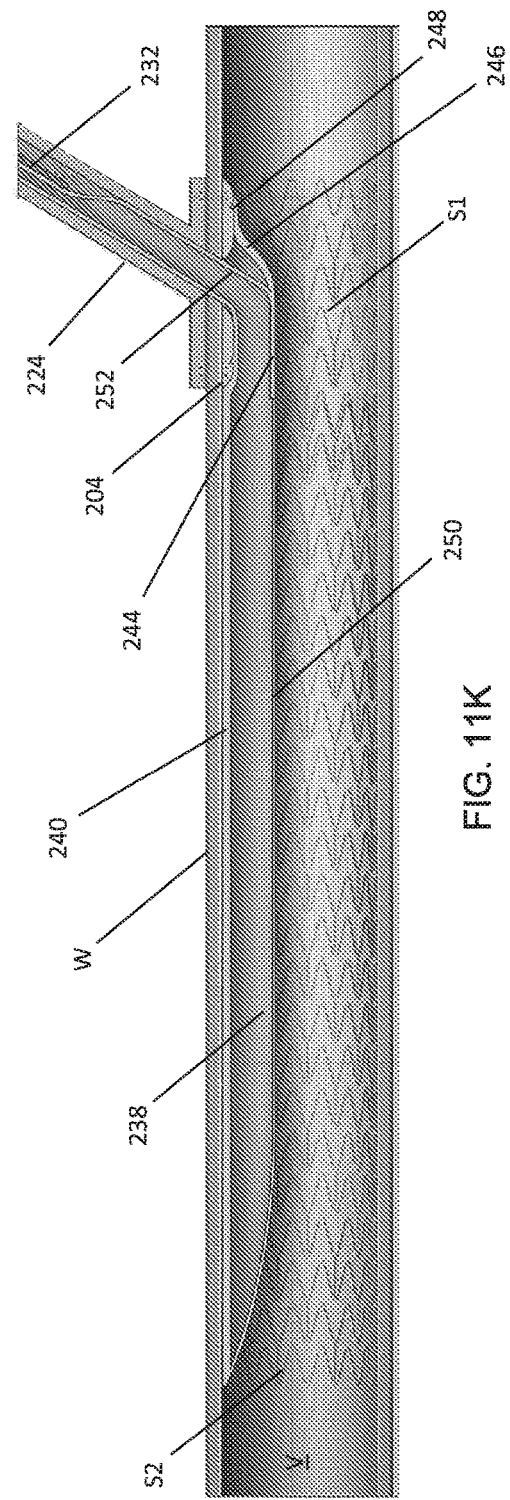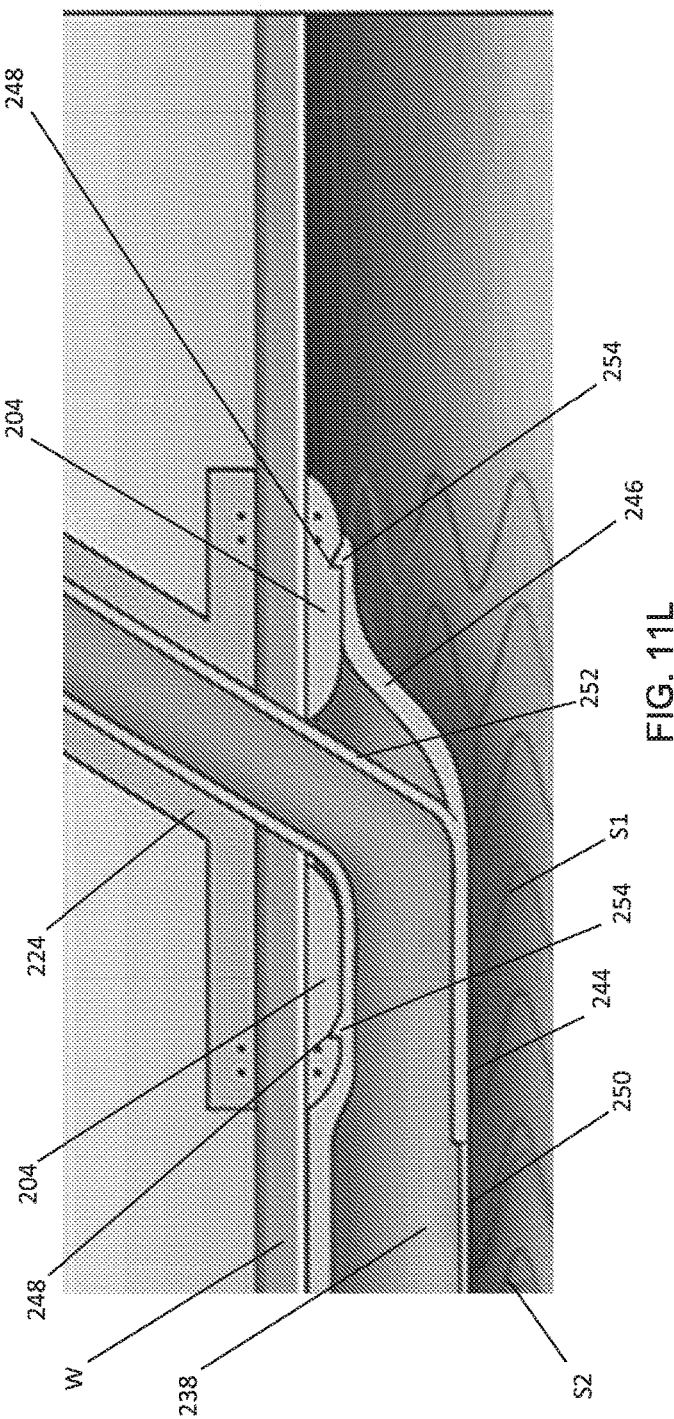

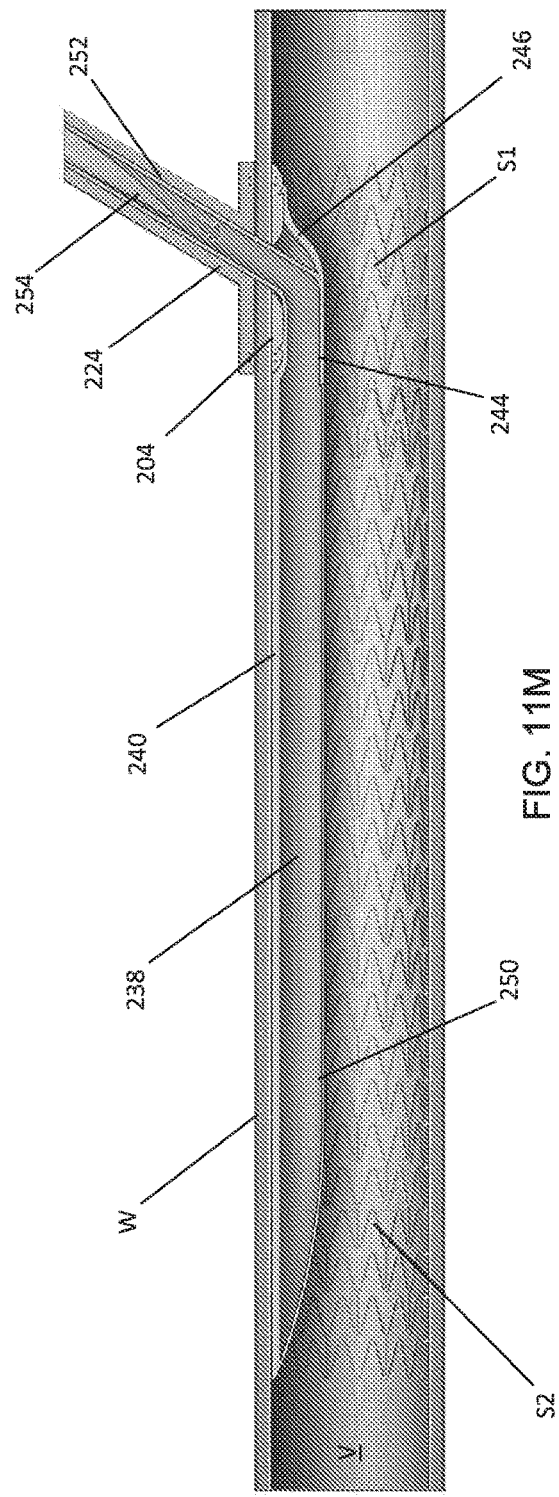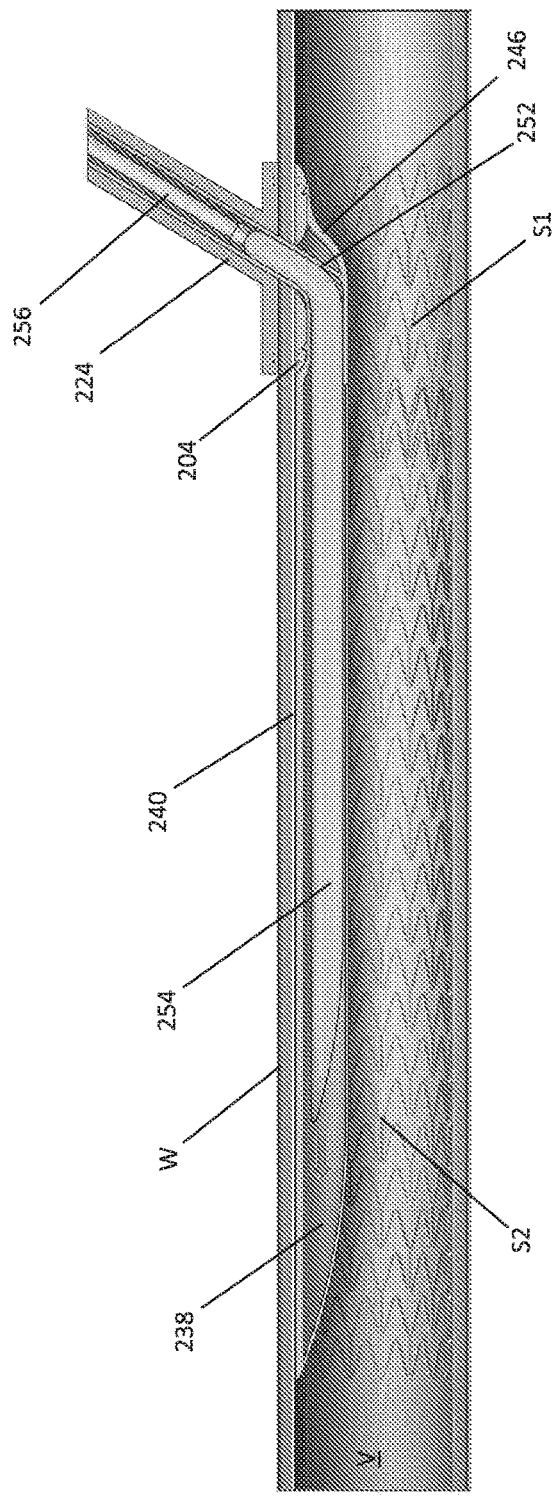

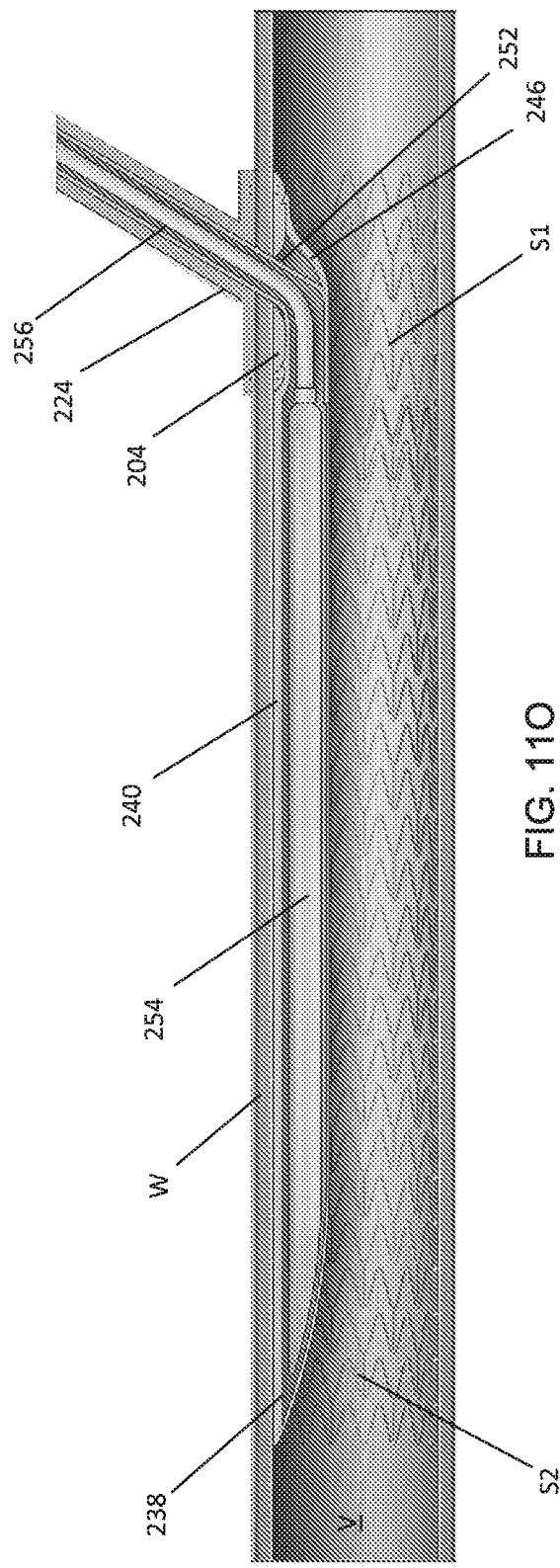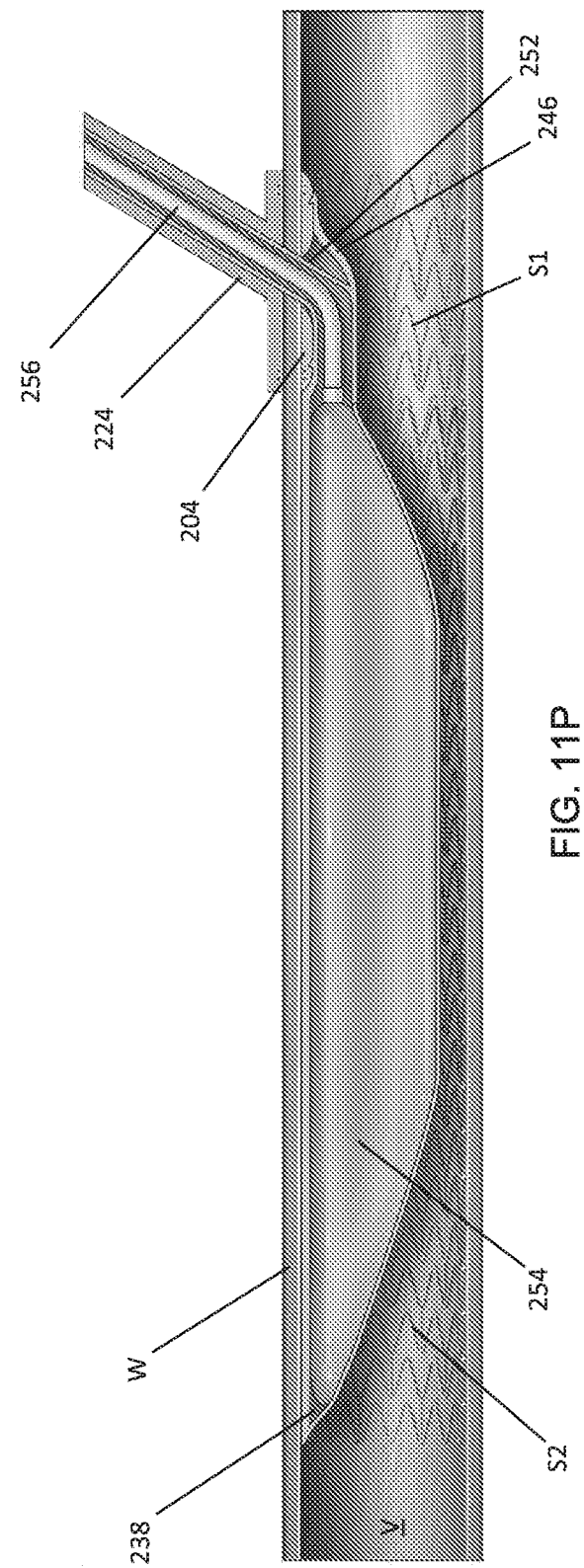

CARDIAC ASSIST DEVICE

CROSS REFERENCE TO RELATED APPLICATIONS

This application claims priority benefit of U.S. Provisional Application Ser. No. 62/195,685 filed 22 Jul. 2015, and U.S. Provisional Application Ser. No. 62/324,198 filed 18 Apr. 2016; the contents of which are hereby incorporated by reference.

FIELD OF THE INVENTION

The present invention in general relates to medical devices and systems and in particular to a minimally invasive cardiac assist device and method of implantation thereof.

BACKGROUND OF THE INVENTION

Heart disease is one of the leading causes of death. Currently, medical science cannot reverse the damage done to the cardiac muscle by heart disease. One solution is a heart transplant; however, the number of cardiac patients in need of a heart transplant far exceeds the limited supply of donor hearts available.

The scarcity of human hearts available for transplant, as well as the logistics necessary to undertake heart transplant surgery, makes a permanently implantable cardiac assist device is a viable option for many heart patients. An aortic blood pump can be permanently surgically implanted in the wall of the aorta to augment the pumping action of the heart. The aortic Hood pump is one example of a mechanical auxiliary ventricle assist device. When positioned in the aorta such a device can be referred to as dynamic aortic patch, or permanent balloon pump. Historically such a device has been implanted by Adrain Kantrowitz and coworkers via open thoracotomy technique so as to permit open aortotomic insertion of the aortic patch. Alternatively, the aortic blood pump can be inserted endovascularly.

Typically, the aortic blood pump includes a flexible bladder to be inflated and deflated in a predetermined synchronous pattern with respect to the diastole and systole of the patient to elevate aortic blood pressure immediately after aortic valve closure. Inflation and deflation of the bladder can be accomplished by means of a supply tube connected to the bladder and can be connected to a percutaneous access device (PAD). The PAD can be permanently surgically implanted in a patient's body to provide a through-the-skin coupling for connecting the supply tube to an extra-corporeal fluid pressure source. Alternatively, the fluid pressure source can be implanted wholly within the body, energized by electromagnetic means across intact skin, or energized by or chemical energy found within the body or some other means. Electrical leads from electrodes can implanted in the myocardium are likewise brought out through the skin by means of the PAD. The aortic valve status or any cardiovascular parameter that is associated with this status can be employed to control the fluid pressure source to inflate and deflate the inflatable chamber in a predetermined synchronous relationship with the heart action.

It is appreciated that fluid flow can be induced through a variety of means of energizing the shape change of a device component fluidly coupled to the blood column. This is illustratively accomplished with piezoelectrics, biochemicals, MEMs structures, hydraulics, ferrofluidics, electromagnetics, direct mechanical force application, or a combination thereof.

The aortic blood pump acts to assist or augment the function of the left ventricle and is typically restricted to use in patients who have some functioning myocardium. The aortic blood pump does not need to be operated full time, and in fact, can be operated periodically on a scheduled on-time, off-time regimen. Typically, the patient can be at least temporarily independent of the device for periods of one to four hours or more, since the aortic blood pump does not require continuous operation.

U.S. Pat. No. 4,051,840 discloses a dynamic aortic patch that is surgically implanted in the thoracic aorta and is systematically inflated and deflated to generate pressure waves in the bloodstream. An alternative formulation of the hemodynamics of the counterpulsation device phasically alters the aortic compliance so as to lower the afterload on the left ventricle. The pressure waves assist the heart by augmenting the circulation of the blood through the body. The patch includes a flexible inflatable bladder and an independent envelope. The envelope has a reinforced surface for limiting and directing inflation of the bladder inwardly toward the lumen of the aorta.

U.S. Pat. No. 6,471,633 discloses a dynamic aortic patch with an elongate bladder having a semi-rigid shell body portion and a relatively thin membrane portion defining an inflatable chamber. At least one passage extends through the shell body defining an opening in the inner surface of the shell body. The flexible membrane can be continuously bonded to the shell body adjacent the peripheral side edge to define the enclosed inflatable chamber in communication with the passage. The membrane has a reduced waist portion defining a membrane tension zone adjacent to the opening of the passage into the chamber to prevent occluding the entrance while deflating the chamber. An outer layer can be bonded to the outer side of the semi-rigid wall portion of the aortic blood pump and cut with a freely projecting peripheral edge portion to provide a suture flange for suturing the aortic blood pump in place within an incision in the aorta.

Further details regarding the structure and function of the aortic blood pump and associated devices and controls can be obtained from U.S. Pat. No. 6,511,412 issued Jan. 28, 2003; U.S. Pat. No. 6,471,633 issued Oct. 29, 2002; U.S. Pat. No. 6,132,363 issued Oct. 12, 2000; U.S. Pat. No. 5,904,666 issued May 18, 1999; U.S. Pat. No. 5,833,655 issued Nov. 11, 1998; U.S. Pat. No. 5,833,619 issued Nov. 10, 1998; U.S. Pat. No. 5,242,415 issued Sep. 7, 1993; U.S. Pat. No. 4,634,422 issued Jan. 6, 1987; and U.S. Pat. No. 4,630,597 issued Dec. 23, 1986 which are incorporated by reference in their entirety herein.

While conventional aortic balloon pumps are well known to the art, a stable aortic blood pump implant is desirable. For example, the constant movement of blood, movement of the vessel wall and the movement of the pump itself can result in deformation of the pump and vessel damage at blood/pump and vessel/pump interface area. There is a continuing need for a cardiac pump including a structure adapted to maintain implant stability that is implanted with minimally invasive surgical incisions with accurate location placement.

SUMMARY OF THE INVENTION

A cardiac assist device includes an expandable primary pumping element in operational communication with a securement positioned within a stent, where the stent is configured for placement within a vessel of a patient. There is at least one locating feature on the securement allowing a conduit external to the vessel to be accurately located and then joined the securement through a wall of the vessel. The secondary pumping element is insertable into the primary pumping element.

A cardiac assist device includes at least two primary pumping elements, each of the at least two primary pumping elements are in operational communication with a securement positioned within a stent, where each stent is configured for placement within a vessel of a patient. A first conduit is external to the vessel, where the first conduit is joined to a first securement through a wall of the vessel. A second conduit is external to the vessel, where the second conduit is joined to a second securement through a wall of the vessel. There is at least one locating first feature on the first securement, and at least one locating second feature on the first securement. A first secondary pumping element is insertable into a first of the at least two expandable primary pumping elements, and a second secondary pumping element is insertable into a second of the at least two expandable primary pumping elements. Such a configuration is well suited for a base cardiac device that is added in multiples based on the desired pumping capacity for a range of individuals or those patients with extraordinary pumping capacity requirement that cannot be accomplished by a single vessel trait.

A process of implanting a cardiac device includes creating an end-to-side anastomosis in a wall of a vessel, joining a prirruary pumping element in operational communication with a securement within the vessel to a conduit external to the vessel, the conduit joined to the securement through the end-to-side anastomosis in the wall of the vessel, and inserting a secondary pumping element into the primary pumping element through the conduit.

A process of operating a cardiac assist device implanted in a patient includes cyclically inflating and deflating a first inflatable cardiac primary pumping element with timing and parameters for increasing cardiac output of the patient, while also monitoring von Willebrand factor protein for a conformational change in patient blood associated with excess blood shearing or other measure of shear stress imposed by the myocardial wall on the cellular circulating elements of the blood or macromolecules, and adjusting the device operation parameters to inhibit the absolute number of the protein with the conformational change.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which like reference numerals refer to like parts throughout the several views, and wherein:

FIGS. 2A-2I are a series of simplified cross-sectional views further describing the implantation and deployment of a cardiac assist device of FIGS. 1A-1N in accordance with embodiments of the invention;

FIGS. 3A-3I are a series of cross-sectional views of a needle and plunger to assist in the implantation and deployment of a cardiac assist device in accordance with embodiments of the invention;

FIG. 5A is a cross-sectional side view of a percutaneous access device implanted in a patient for providing a power or actuating connection to a cardiac assist device according to an embodiment of the invention;

FIG. 5B illustrates the use of an implanted transcutaneous energy transfer module (TET) for providing power or actuating connection to a cardiac assist device according to an embodiment of the invention;

FIGS. 6A-6F are a series of cross-sectional side views showing the implementation and actuation of a ventricular assist device in accordance with embodiments of the invention;

FIGS. 7A-7D are a series of partial cutaway perspective views showing the implantation and deployment of a cardiac assist device in accordance with embodiments of the invention;

FIGS. 8A and 8B are cross-sectional views of an aortic assist device as a flexible encasement with a balloon inside in a deflated and inflated state, respectively. In accordance with embodiments of the invention;

FIGS. 9A-9D are a series of perspective and cross-sectional views of an aortic assist device integrated with a stent for delivery into an artery in accordance with embodiments of the invention;

FIGS. 10A-10L are a series of perspective and cross-sectional views showing the implementation and actuation of the aortic assist device shown in FIGS. 9A-9D in accordance with embodiments of the invention.

DETAILED DESCRIPTION OF THE INVENTION

A cardiac pump and an assist system according to the present invention have utility to increase blood ejection from a compromised heart. An implantable cardiac pump acting as an assist device provided by the present invention includes an attachment system and locating features that enable a minimally invasive procedure to implant and deploy one or more aortic blood pumps in a patient. Embodiments of the insertable cardiac pump are replaceable without resort to a conventional open surgical procedure. Still other embodiments of the present invention allow for monitoring of cardiac pump operation to allow for replacement in advance of chamber failure. Additionally, as the dynamics (velocity and acceleration) of the blood-contacting surface of existing rotary continuous flow cardiac assist devices may be associated with flow-related pathologic disturbances in intravascular clotting mechanisms (such as conformational changes in von Willebrands factor or other measure of shear stress imposed by the myocardial wall on the cellular circulating elements of the blood or macromolecules), the dynamics of blood-contacting interface of the inventive cardiac assist device mimic the dynamics of the blood-contacting interface of the naturally occurring left ventricle, thereby minimizing flow-related device-associated pathologic disturbances of intravascular dotting mechanisms. A process of operating a cardiac assist device includes cyclically inflating and deflating one or more inflatable cardiac pumping chambers with timing and parameters as to pressure, deflection, and speed of inflation to increasing cardiac output of the patient. By monitoring the von Willebrand factor protein for conformational changes in patient blood associated with excess blood shearing, the one or more parameters needed to inhibit the absolute number of the protein with the conformational change are adjusted as to the operation of a cardiac implant device, including those described herein. Such parameters represent a tool in both the structural and operational aspects of a cardiac assist device.

Figure 1A:
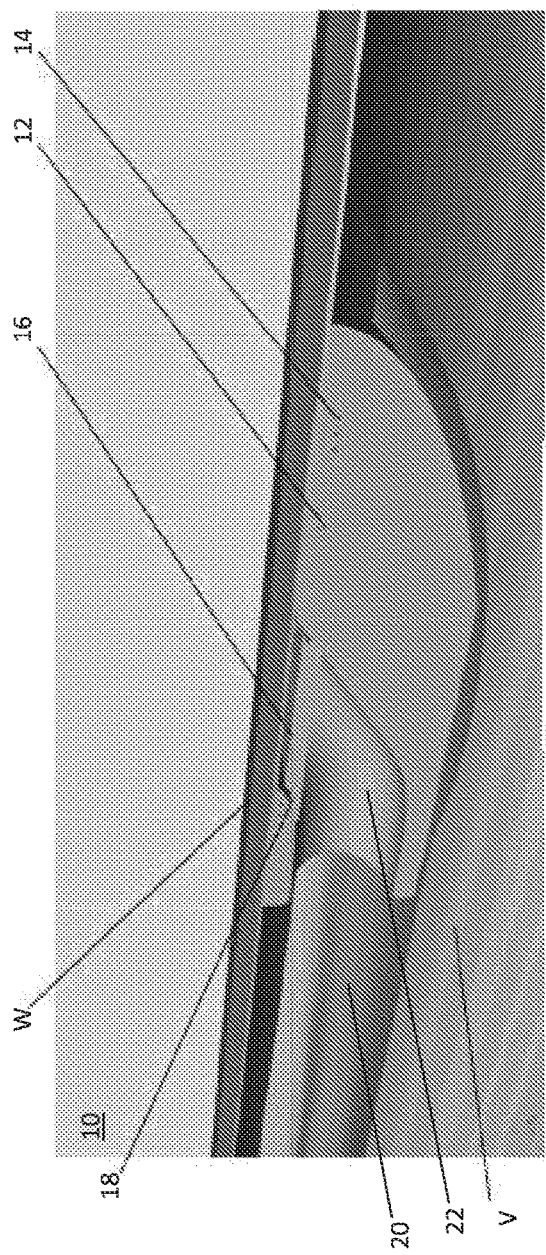
FIGS. 1A-1N are a series of partial cutaway perspective views showing the implantation and deployment of a cardiac assist device in accordance with embodiments of the invention.

An embodiment of a system 10 for the attachment and deployment of a cardiac pump is described in FIGS. 1A-1N as a series of partial cutaway perspective views in conjunction with the cross-sectional views of FIGS. 2A-2I that further describe the implantation and deployment of a cardiac assist device inclusive of the pump depicted with respect to FIGS. 1A-1N. In FIG. 1A an endo-aortic securement 12 (hereinafter referred to as securement 12) connected to a non-distensible collapsed sub-neo-intimal primary pumping element 20 (hereinafter referred to as primary pumping element 20 or synonymously as a luminal confinement or a pocket) are shown implanted in a patient vessel V, illustratively including the aorta. Implantation of the endo-aortic securement 12 and luminal confinement 20 occurs through a vascular catheter illustratively inserted in the leg or groin area of the patient. Alternatively, the implantation is by the subclavian artery, axial artery, directly through the wall of the aorta, or another vessel. The securement 12 has locating features 14 and a stabilization/alignment target 16 that is attached to the securement 12 in some inventive embodiments, via a detachable feature 18; such feature being a ring, perforable septum, or movable iris. The stabilization/alignment target 16 covers an introductory guide channel 22 for passage into luminal confinement 20.

An often overlooked aspect of cardiac assist devices is the reliable implantation of the same. To this end, an endo-aortic securement 12, a sub-neo-intimal primary pumping element 20, or a combination thereof are retained in a position within the aorta through resort to an expandable mesh stent S in dilation against the endoluminal wall of the aorta (not shown for visual clarity until FIG. 1M). As a result, the device is positionally stable prior to trans-aortic puncture and during cardiac pumping cycles. It is appreciated that the stent is readily treated with a primary coating to promote long-term stent stability and therefore the device 10 anchored thereto. Such coating substances illustratively include heparin, antibiotics, radiopaque agents, anti-thrombogenic agents, anti-proliferative agents, anti-angiogenic agents; each alone, or in combination. It is further appreciated that a secondary coating overlying the first coating is provided to promote sustained release of the underlying coating substance. Such secondary coatings illustratively include polylactic acid, polyglycolic acid, polyethylene oxide, polycaprolactone, polydioxanones, combinations thereof, and co-polymers thereof.

In certain inventive embodiments, the secondary luminal confinement 20 is formed from a material that induces immunocompatible granulation tissue overgrowth thereon or in-growth therein to effectively render the luminal confinement 20 non-provocative from thrombotic events against the adluminal surface of the luminal confinement 20. Coatings operative herein illustratively include poly-L-lysine (PLL), polymethyl coguanidine-cellulose sulphate (PMCG)-CS/PLL-sodium alginate (SA), polyethyleneimine, poly(dimethyldiallylammonium chloride), chitosan, polyacrylacid, carboxymethylcellulose, cellulose sulfate, pectin, and combinations thereof to form multilayers. It is appreciated that such coatings are readily impregnated with compounds that reduce the immune cascade, these illustratively include heparin and factor H.

Figure 1B:
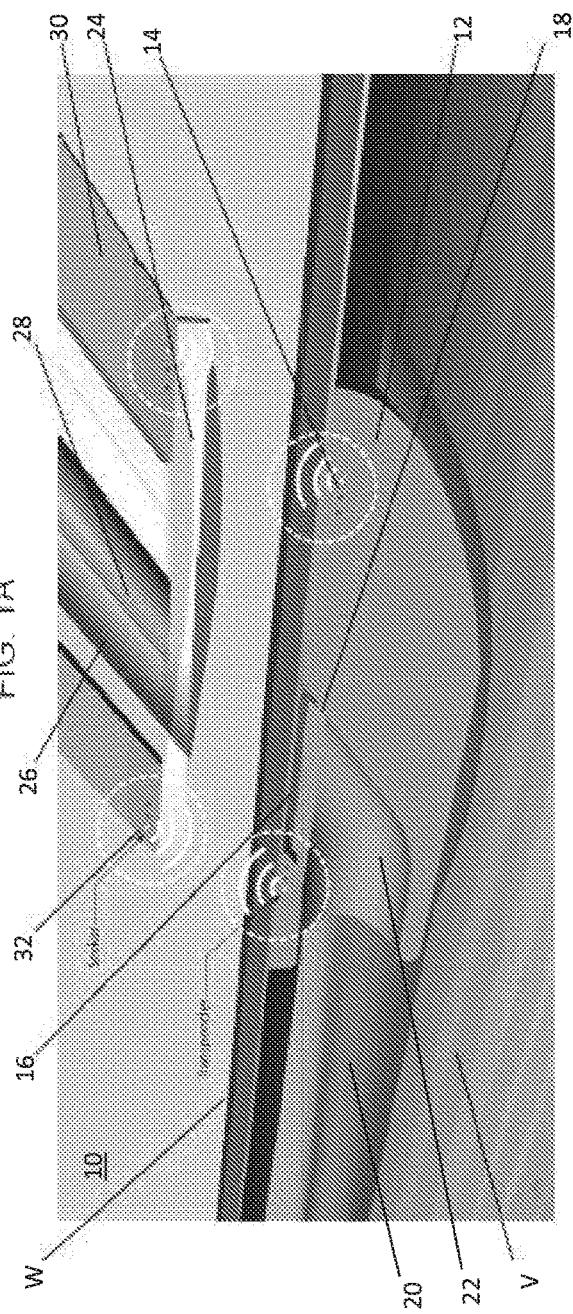
Figure 2A:
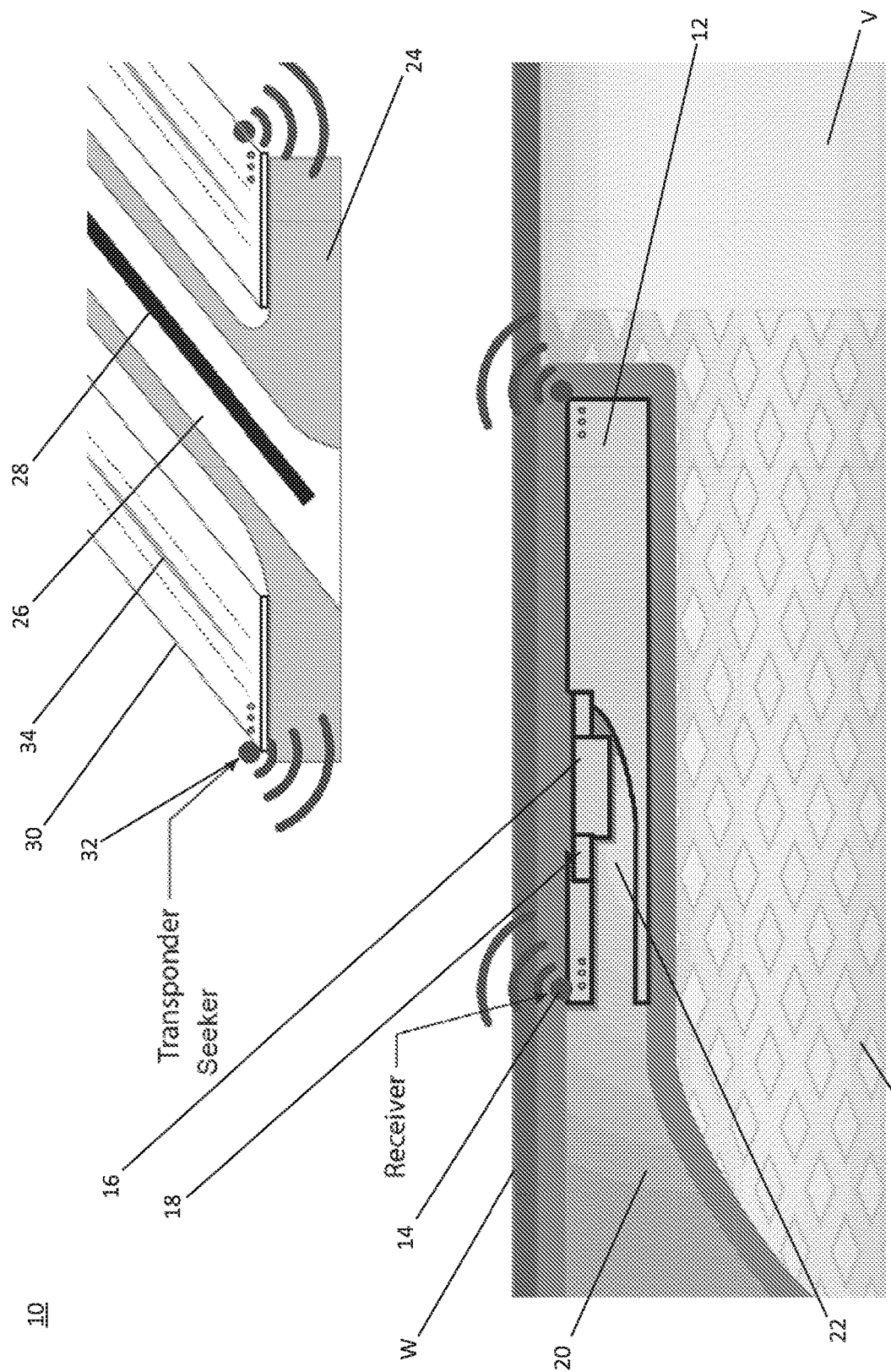
Figure 2B:
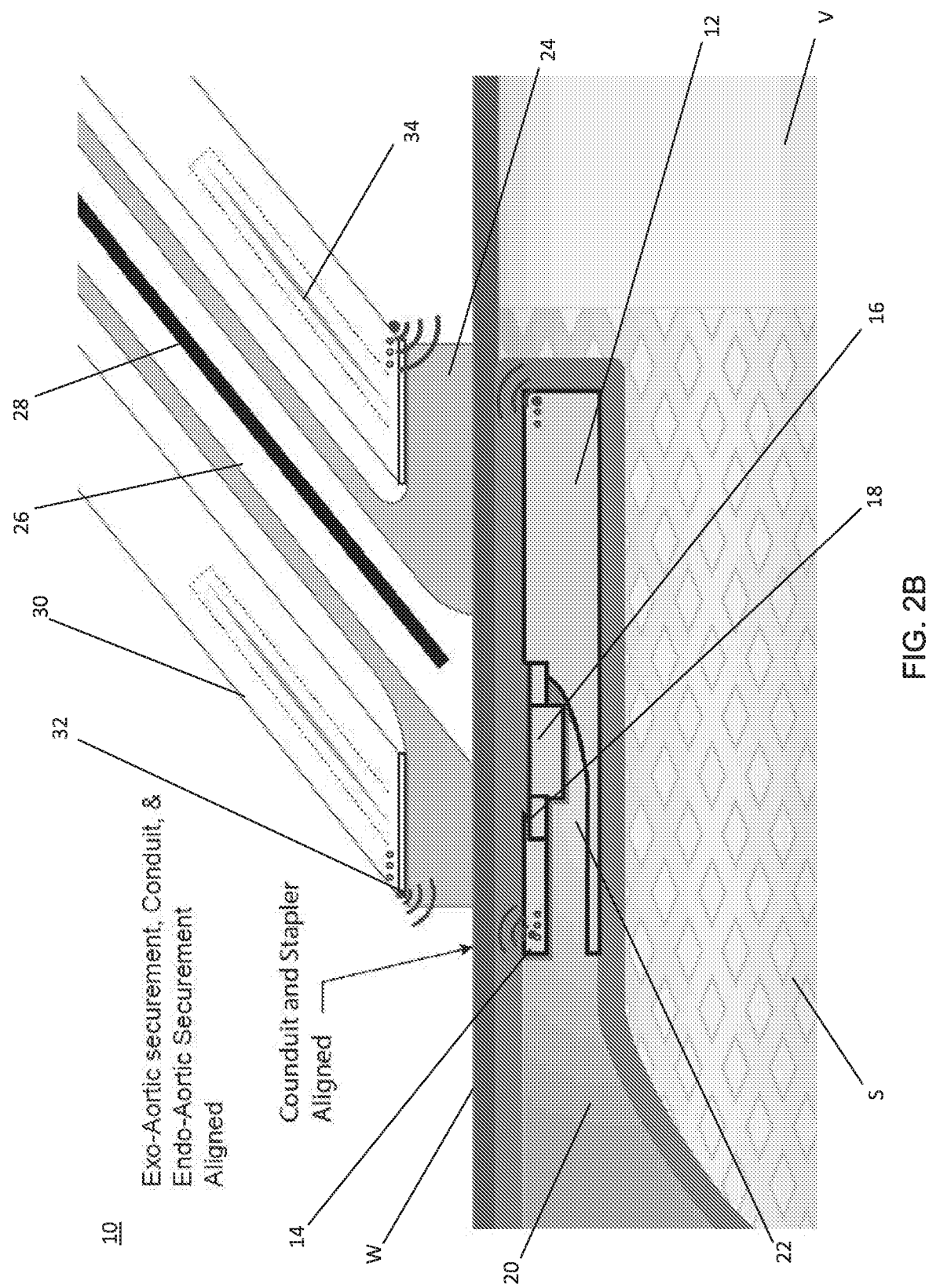
Figure 2C:
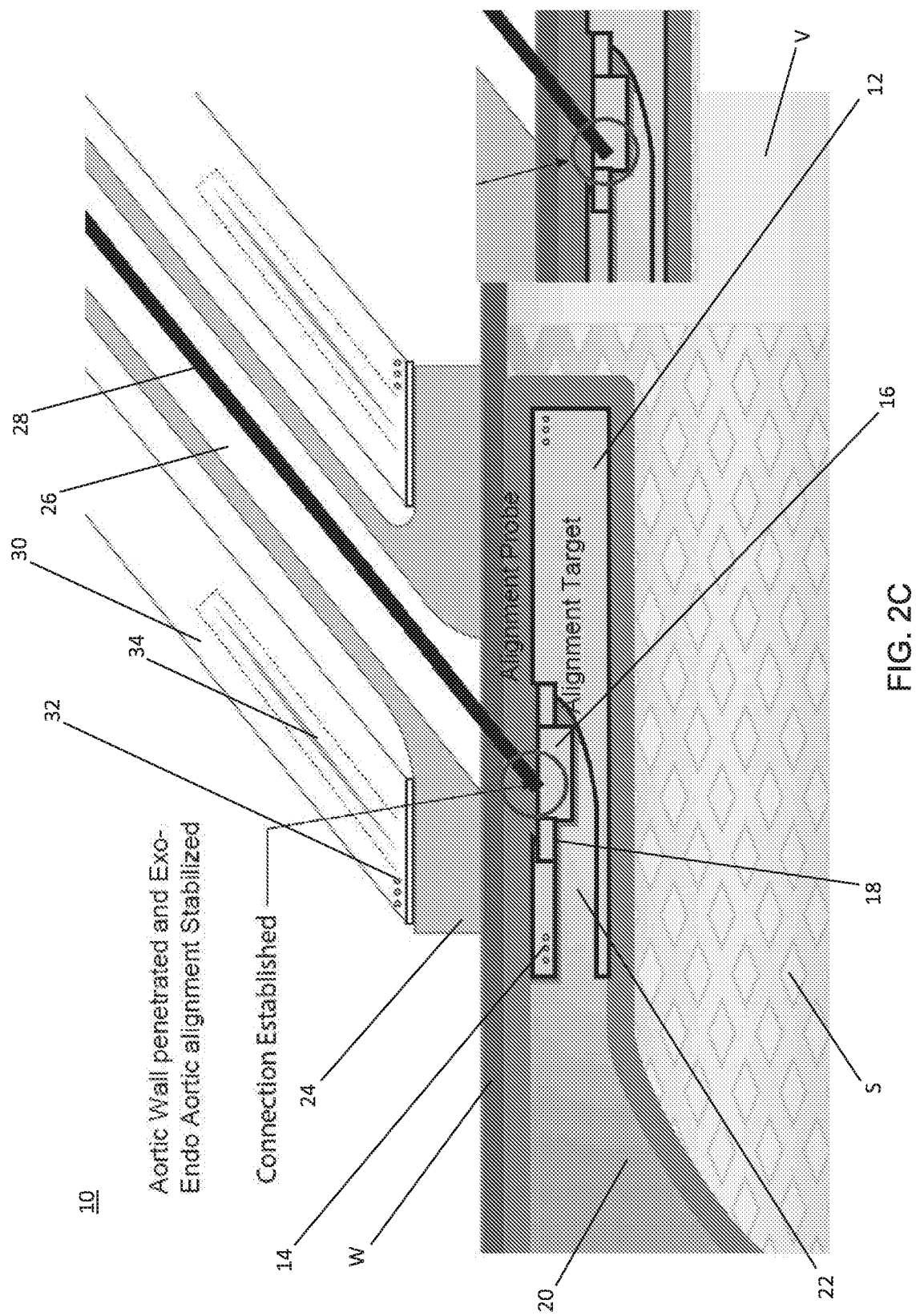

FIG. 1B illustrates the introduction of an exo-aortic securement device illustratively including a stapler, which as shown has a circular shape for providing staples 34 (see FIG. 1E) in a circular perimeter, to attach the flange portion of a conduit 24 through the wall W of the vessel V to the securement 12. It is noted that other perimeter shapes illustratively including oval, square, rectangular may be used to secure the flange of the conduit 24 to the securement 12. It is appreciated that other fasteners deployed from a securement device 30 to join the expandable luminal confinement in mechanical communication with a securement within the vessel to a conduit external to the vessel also include tissue adhesives, screws, thread-like sutures, or other mechanical fasteners conventional to surgery. As shown, the exo-aortic securement device 30 (hereinafter referred to as securement device 30) fits around the conduit 24. Upon docking to the securement device 30 to the securement 12, a hemostatic seal is formed in some embodiments. The securement device 30 has complimentary location features 32 to the locating features 14 on securement 12. The conduit 24 has an aperture 26 configured for insertion of an alignment probe 28 that aligns with the stabilization target 16 as shown in FIG. 1C and FIG. 2B, and once aligned the alignment probe 28 penetrates the wall W of the vessel V and stabilizes the stabilization/alignment target 16 as shown in FIG. 1D and FIG. 2C.

In a specific inventive embodiment the locating features 14 as shown in FIG. 1B are a set of transponders, which may be passive or active, that react to the transmitted seeker signals from the complimentary location features 32 located on the securement device 30 in a similar manner to radio frequency identification RFID based technology. In FIG. 2A the complimentary location features 32 located on the securement device 30 are configured as a transponder/seeker that send signals to the locating features 14 configured as a receiver on the securement 12. Additionally, other locating methods illustratively including light emitting diodes (LED), ultrasound, magnets arrayed as complimentary location features 32, and fluormetry may be used for locating features or fiducial markings for aligning the conduit 24 with the securement 12 to provide an access path into the vessel V.

Figure 1I:
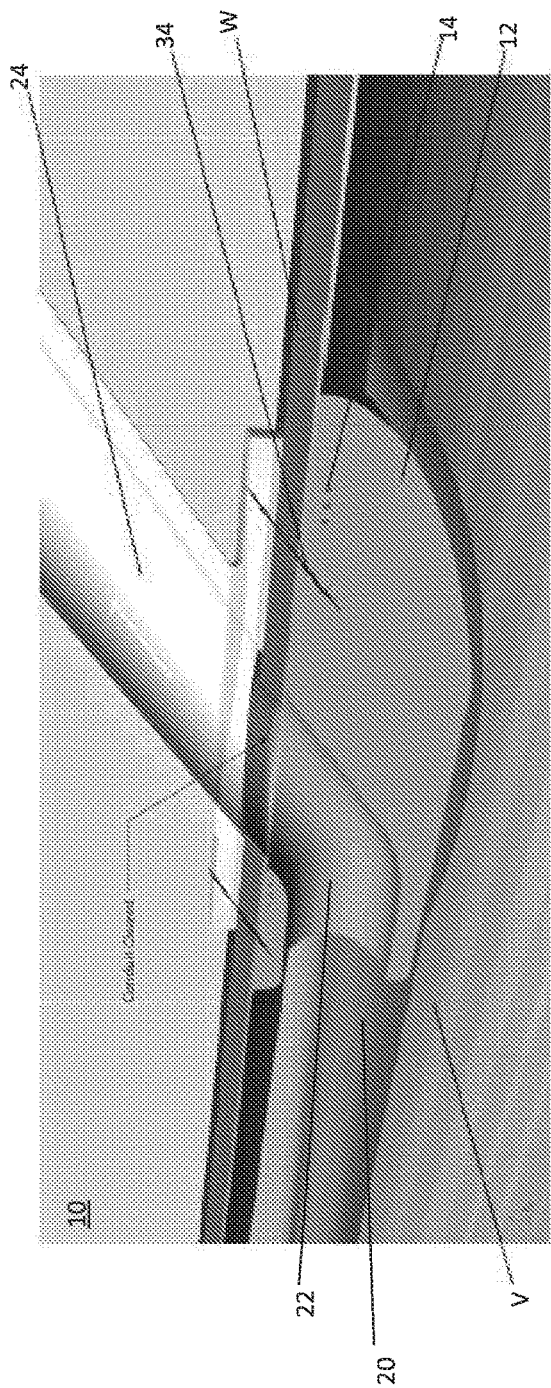
Figure 1J:
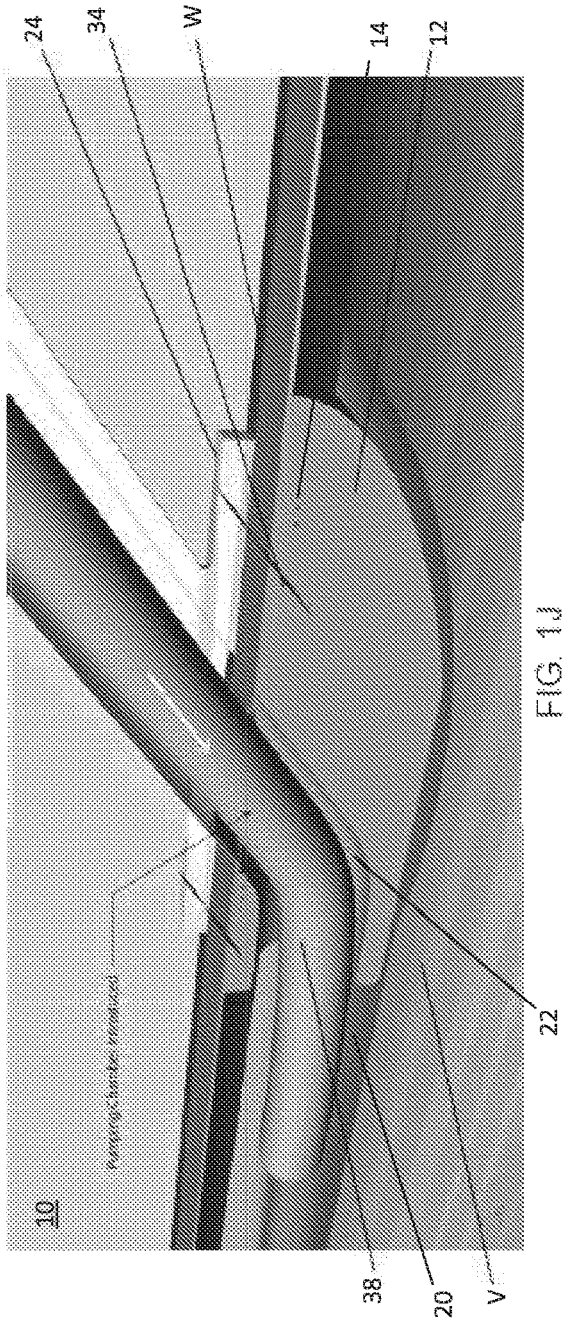
Figure 2D:
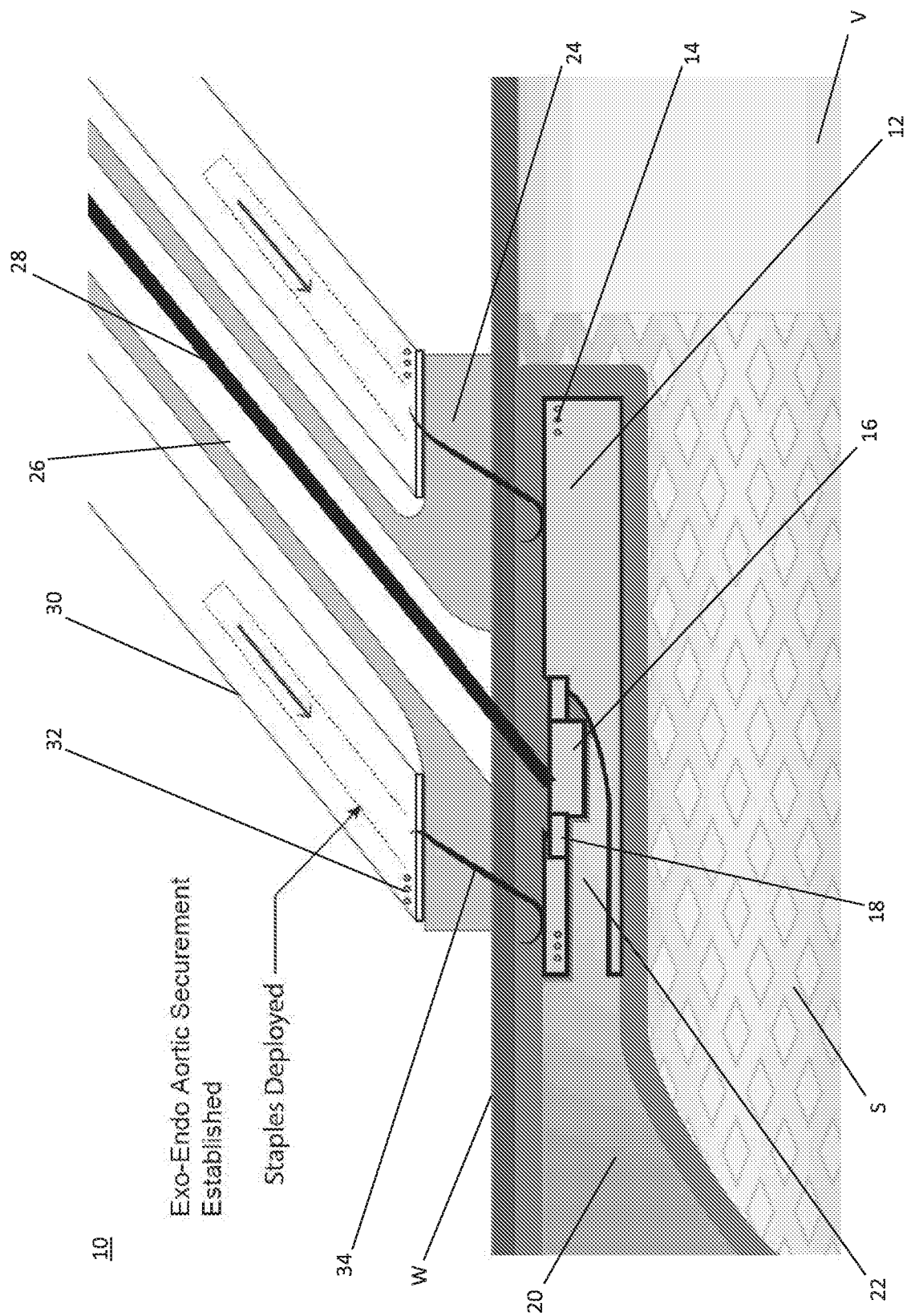
Figure 2E:
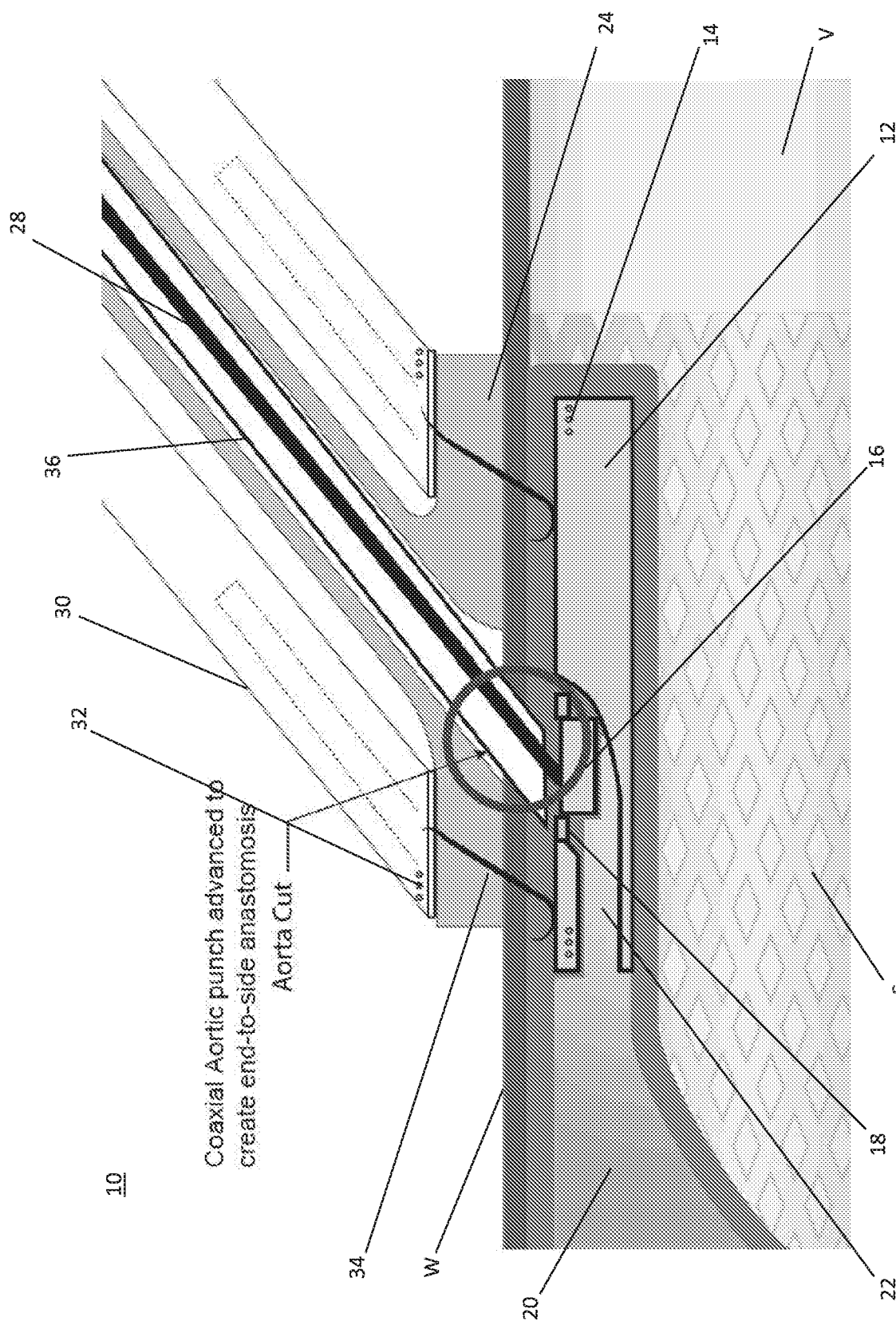
Figure 2F:
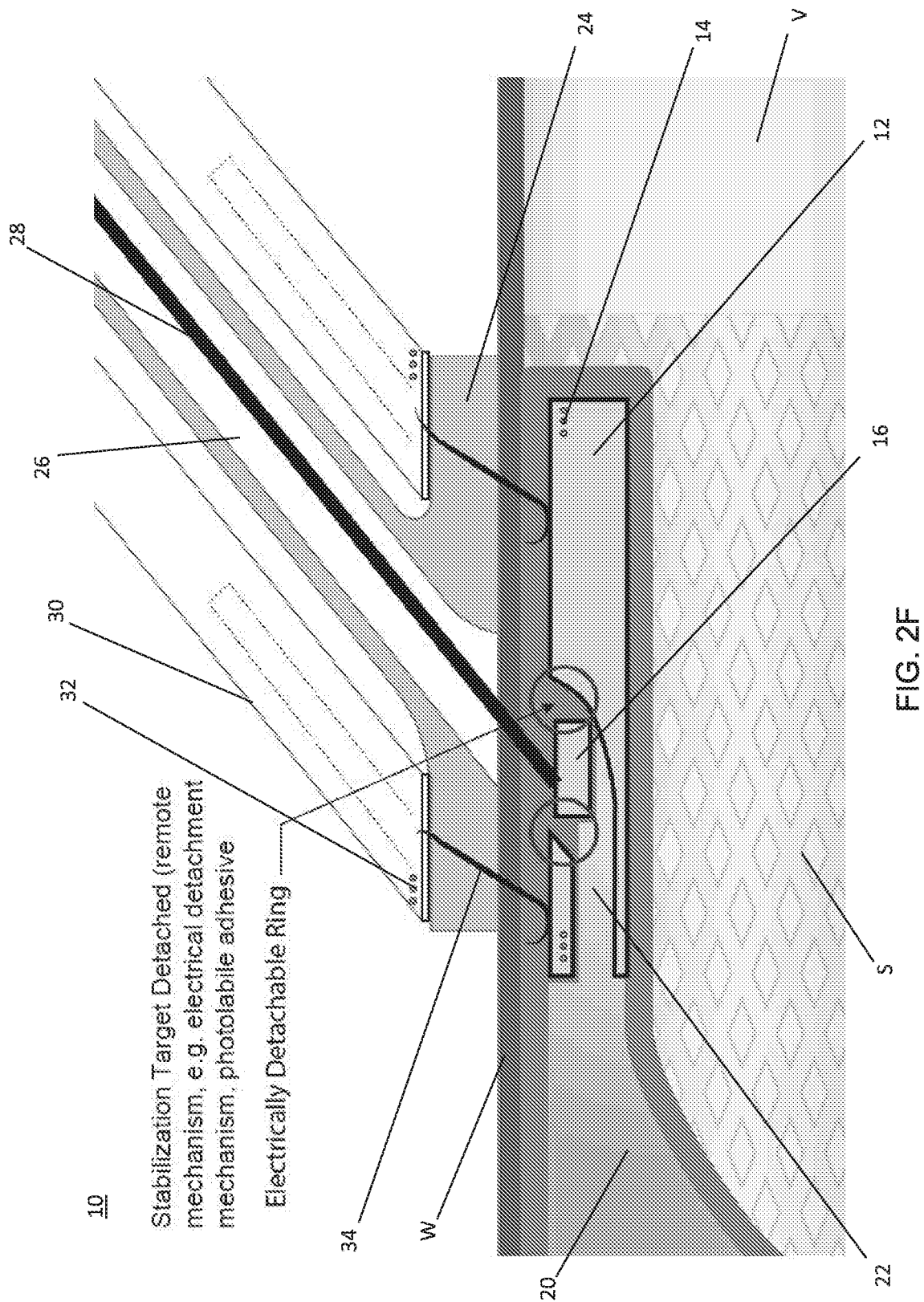
Figure 2G:
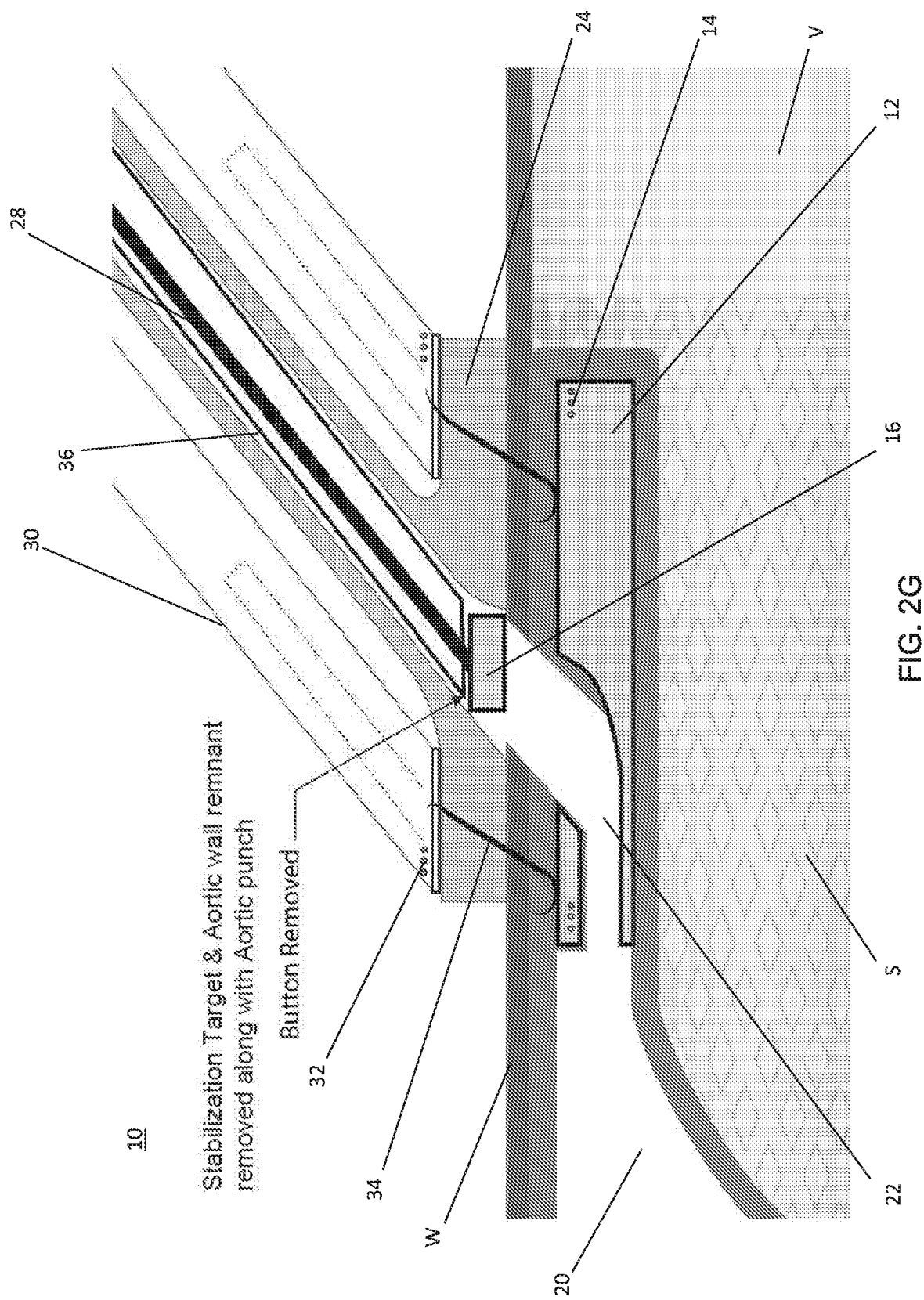
Figure 2H:
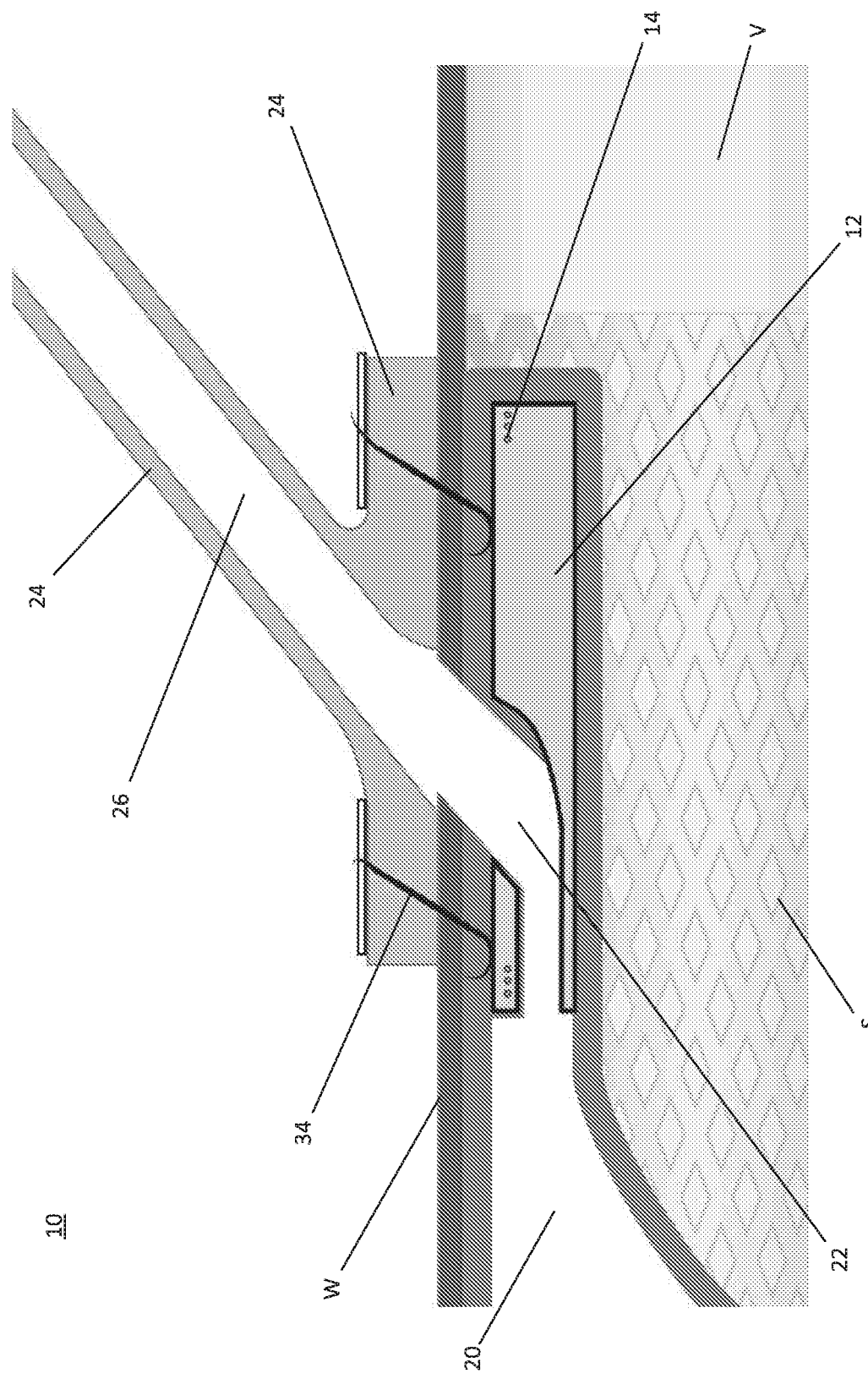
Figure 21:
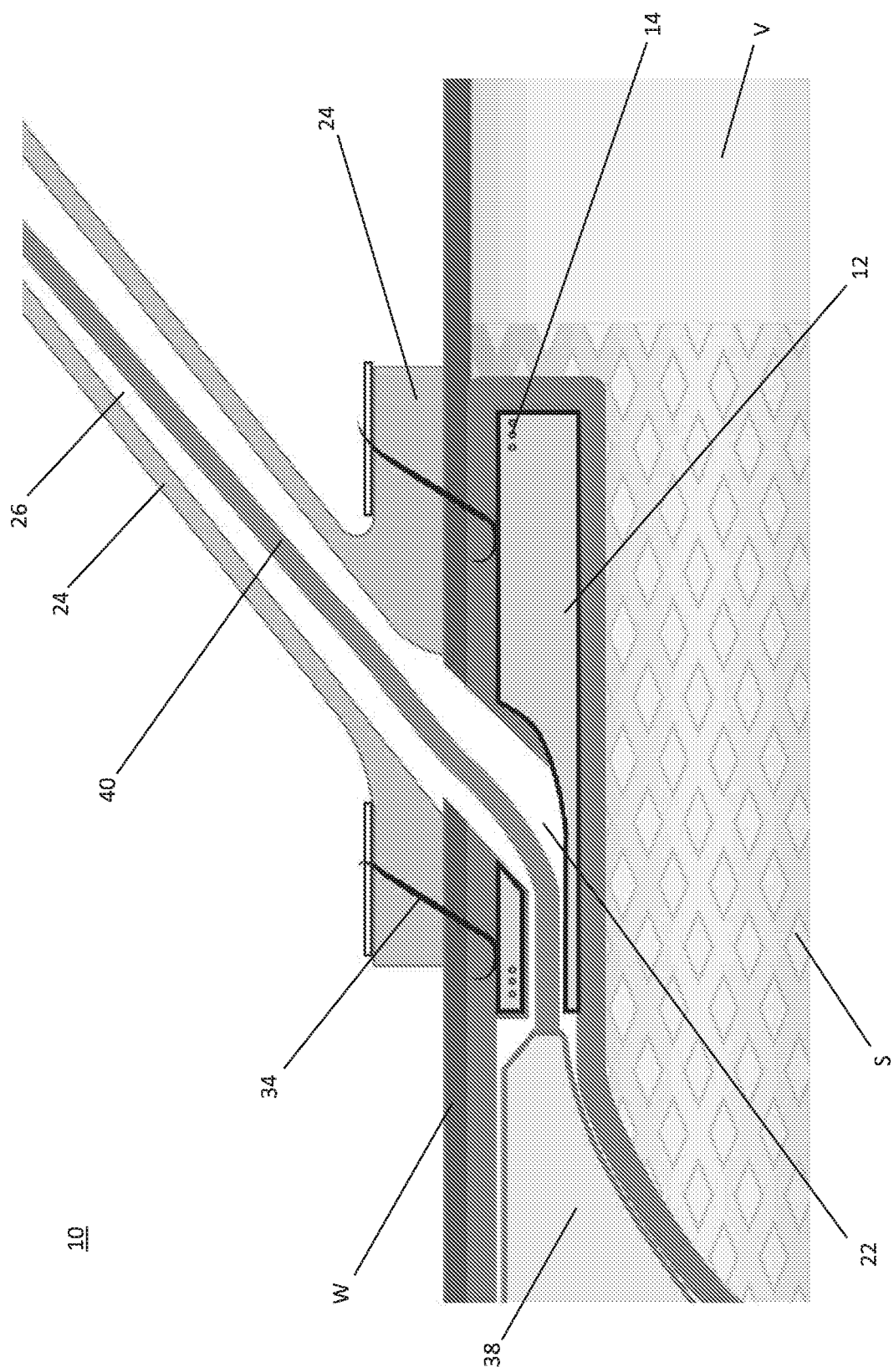
Figure 1:
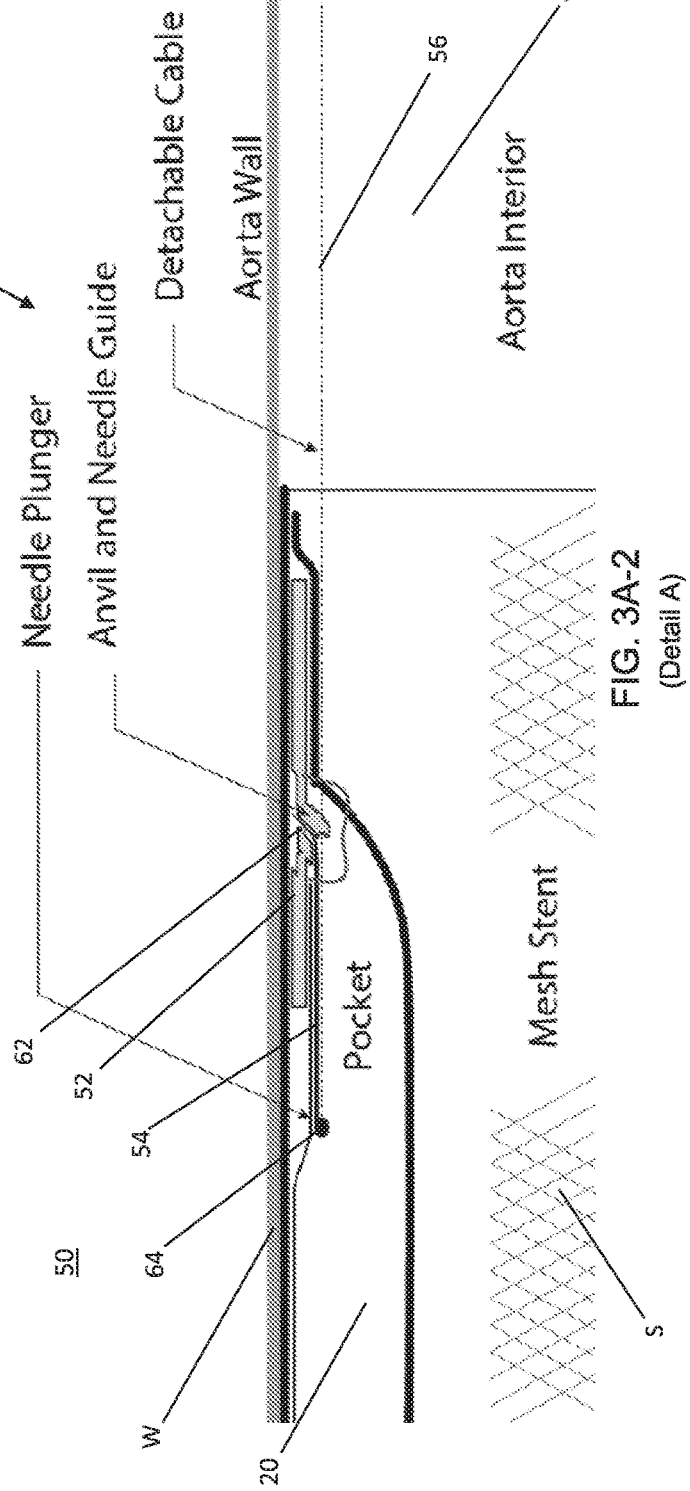

Once the alignment probe 28 is attached to and stabilizes the stabilization/alignment target 16, an exo-endo aortic securement is established using a series of fasteners illustratively shown as staples 34, where the staples 34 are dispensed from the stapler 30, and the staples 34 pierce through an optional buttress (not depicted), then through the flange portion of the conduit 24 and through the wall W and into the securement 12 that has been implanted in the vessel V, illustratively shown as an aorta in FIG. 1E and FIG. 2D. In FIG. 1F and FIG. 2E a coaxial aortic punch 36 is advanced through the aperture 26 of the conduit 24 to create end-to-side anastomosis of the wall W of the vessel V, and the stabilization/alignment target 16 is detached by breaking the detachable ring 18 that holds the stabilization/alignment target 16 to the securement 12 in FIG. 1G and FIG. 2F. In a specific embodiment a Doppler flow meter or similar flow detection sensor may be associated with the coaxial aortic punch 36, or optionally any of the system components proximate to the anticipated aortic punch site, to check for fluid leaks at the interface of the flange 24, securement 12, and the stent S. It is appreciated that optical coherence tomography (OCT) performs micrometer-scale or catheter based imaging ultrasound probe, cross-sectional and three-dimensional imaging by measuring the echo time delay of backscattered light in order to preclude an aortic puncture in the vicinity of an aortic wall defect. Optionally the aortic puncture function can be accomplished with a laser source, ultrasonic, water jet, or other conventional techniques to form a geometrically controlled opening in the aortic wall at a defined location. Detachment of the detachable ring 18 may be accomplished by a remote mechanism that illustratively includes electrical detachment or photolabile adhesive. In FIG. 1H and FIG. 2G, the stabilization/alignment target 16 and remnant of the wall W is removed along with the coaxial vascular punch 36 to provide a clear passage between the conduit 24 and the introductory guide channel 22 of the securement 12 that leads into the primary pumping element 20 as shown in FIG. 1I and FIG. 2H. In FIG. 1J a cardiac pumping chamber 38 in a deflated state, optionally delivered in a removable protective cover sheet (not shown), is introduced via the conduit 24 and through the introductory guide channel 22 of the securement 12 and into the luminal confinement 20. In FIG. 1K the cardiac pumping chamber 38 in the deflated state is fully inserted in the primary pumping element 20 with the insertion line 40 is now visible. In a specific embodiment, the cardiac pumping chamber 38 and insertion line 40 are introduced into a patient via an embedded percutaneous access device (PAD) 70 as shown in FIG. 5A. In FIG. 1L and FIG. 2I the cardiac pumping chamber 38 is inflated so as to expand the luminal confinement 20. FIGS. 1M-1 and 1M-2 are a side cutaway view of the vessel V with a stent S in the region of the securement 12 and the luminal confinement 20, where the pumping chamber 38 is deflated.

FIGS. 1N-1 and 1N-2 are a side cutaway view of the vessel V with a stent S in the region of the securement 12 and the luminal confinement 20, where the pumping chamber 38 is inflated so as to expand the luminal confinement 20 and move a volume of blood in the vessel V. The inflation cycle of the pumping chamber acts as a cardiac assist device to increase blood ejection from a compromised heart of a patient in need thereof. While the expansion of the pumping chamber 38 is depicted as occluding the aorta, it should be appreciated that this is an exaggeration for visual clarity and that such occlusion is implicated in an impair counterpulsation effect, as well as in conformational changes in von Willebrand factor commonly associated with clot formation in downstream vasculature.

Figure 3A:
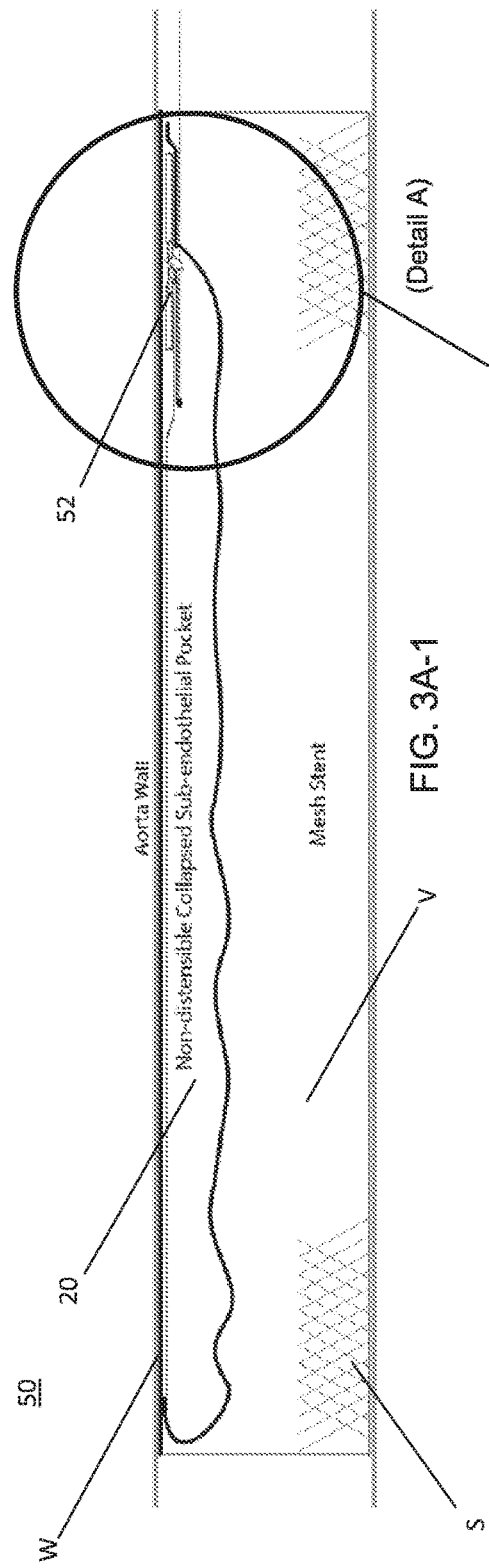
Figure 3D:
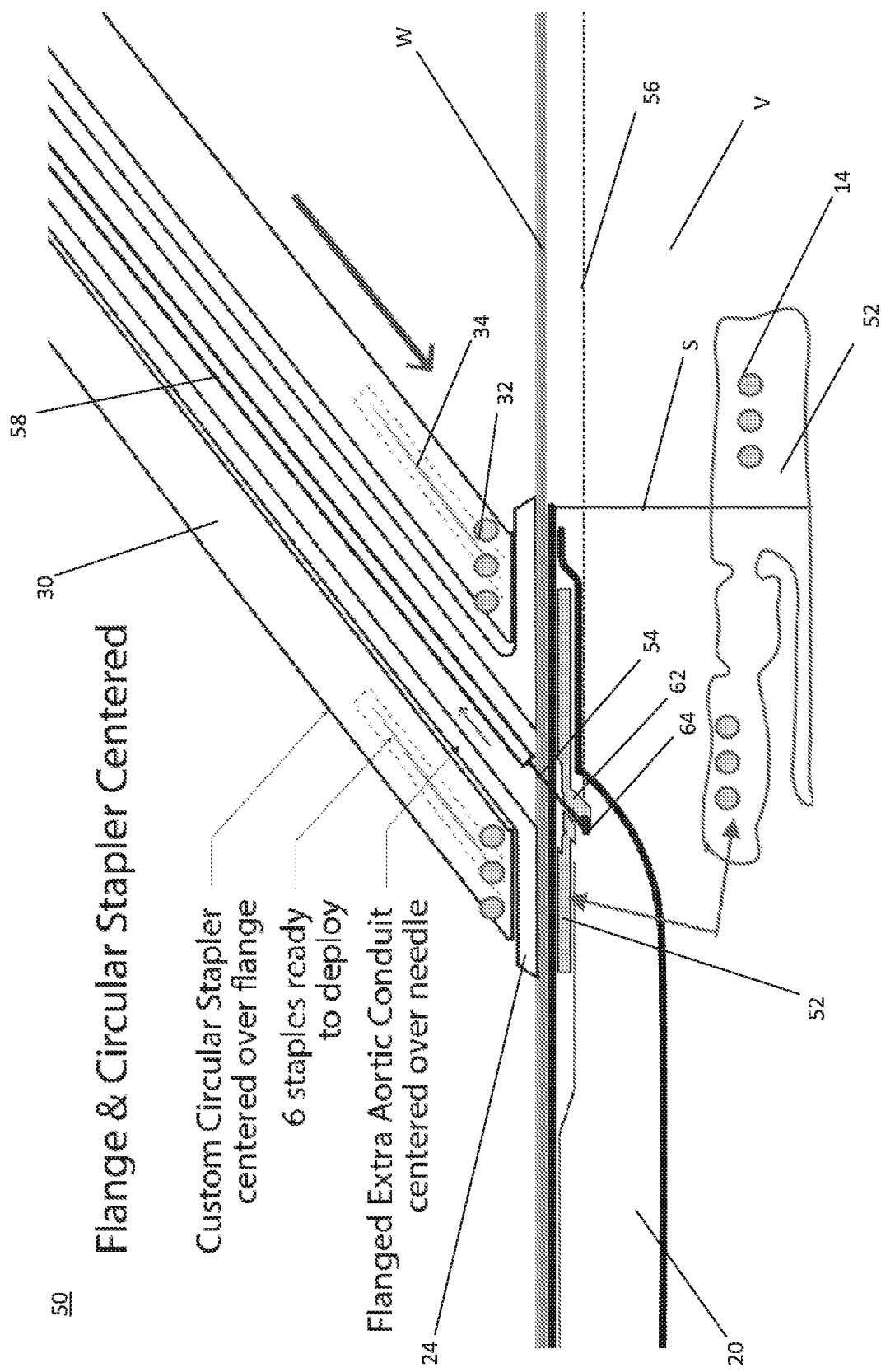
Figure 3E:
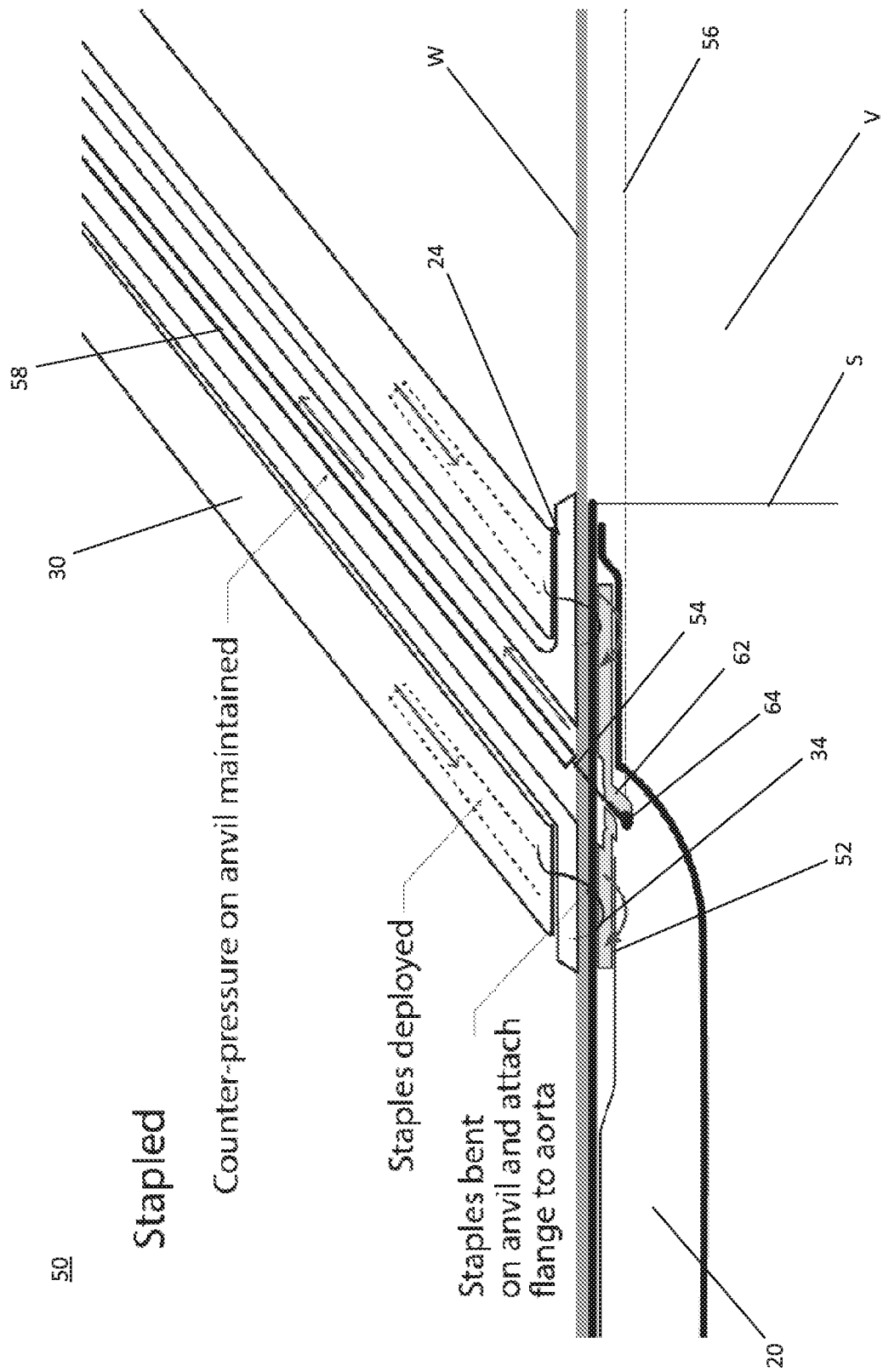
Figure 3F:
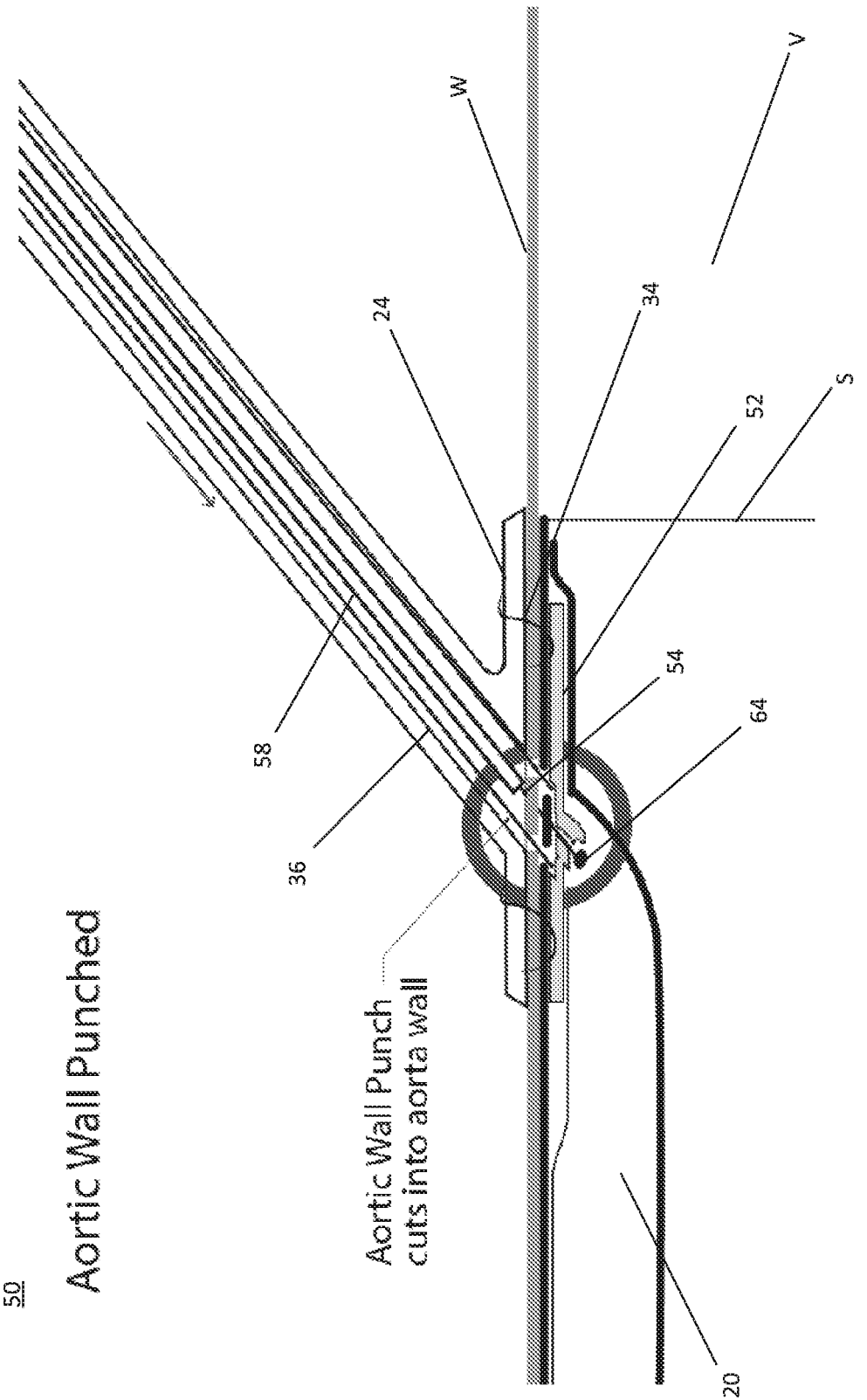
Figure 3G:
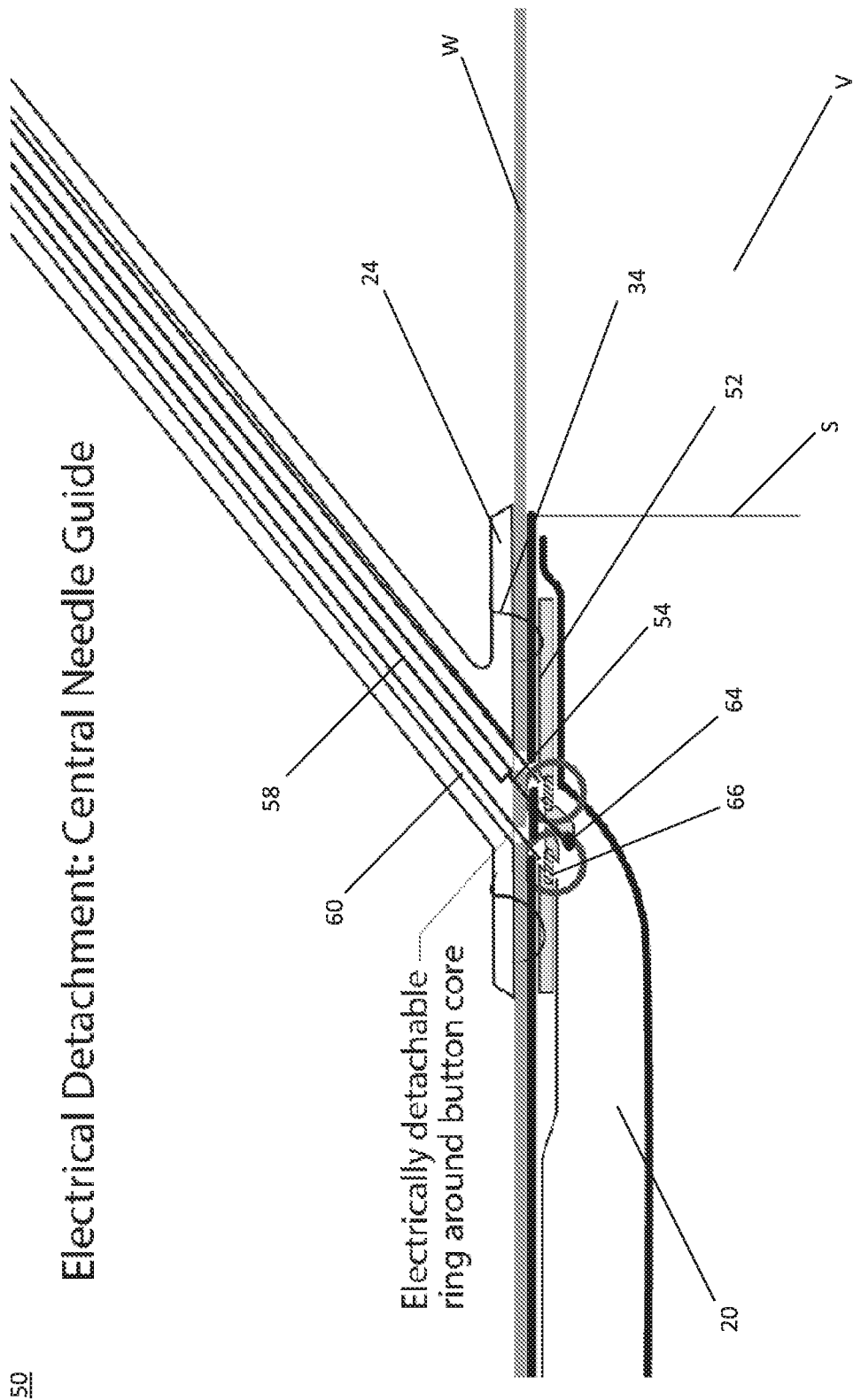
Figure 3H:
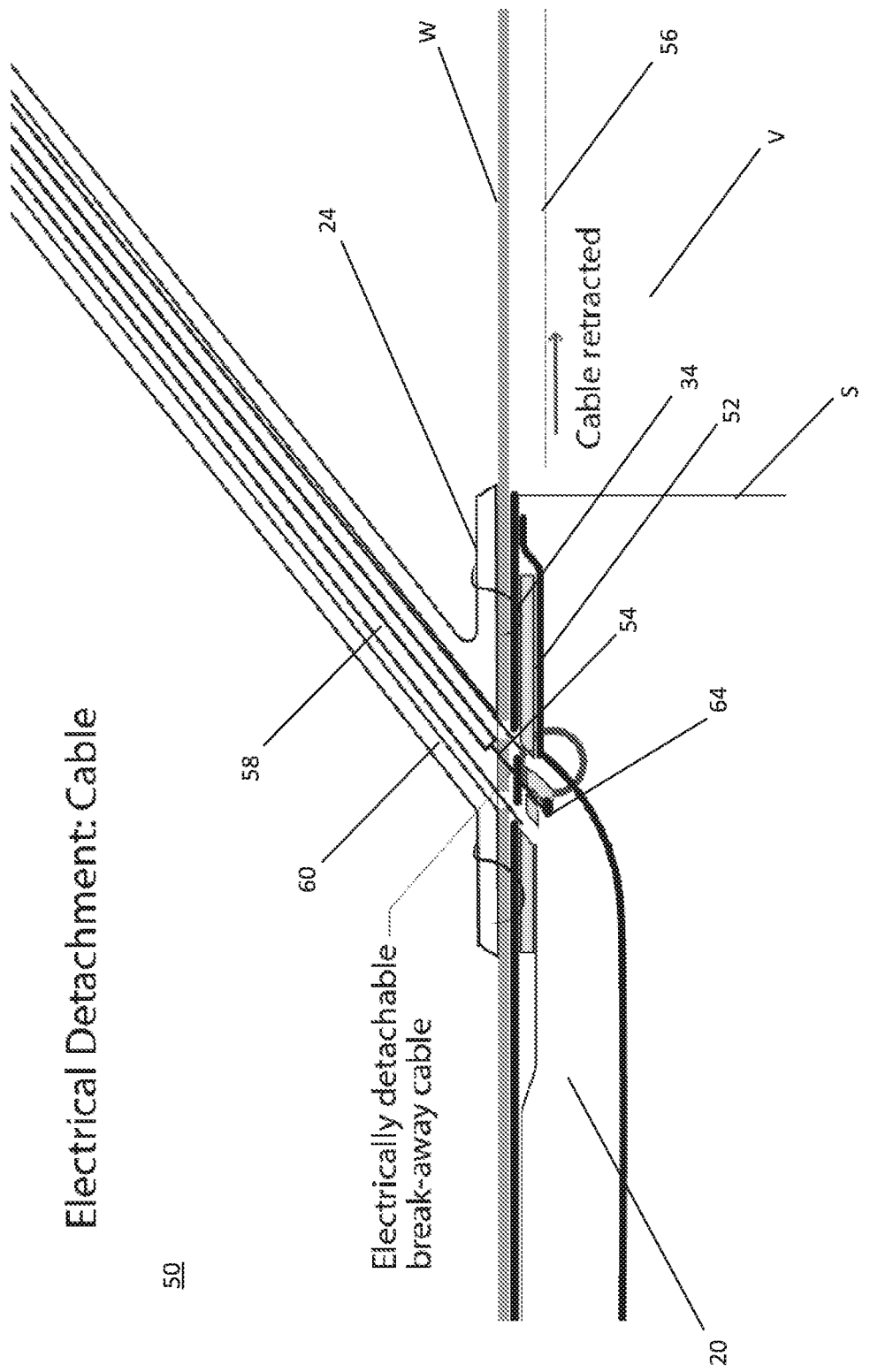
Figure 31:
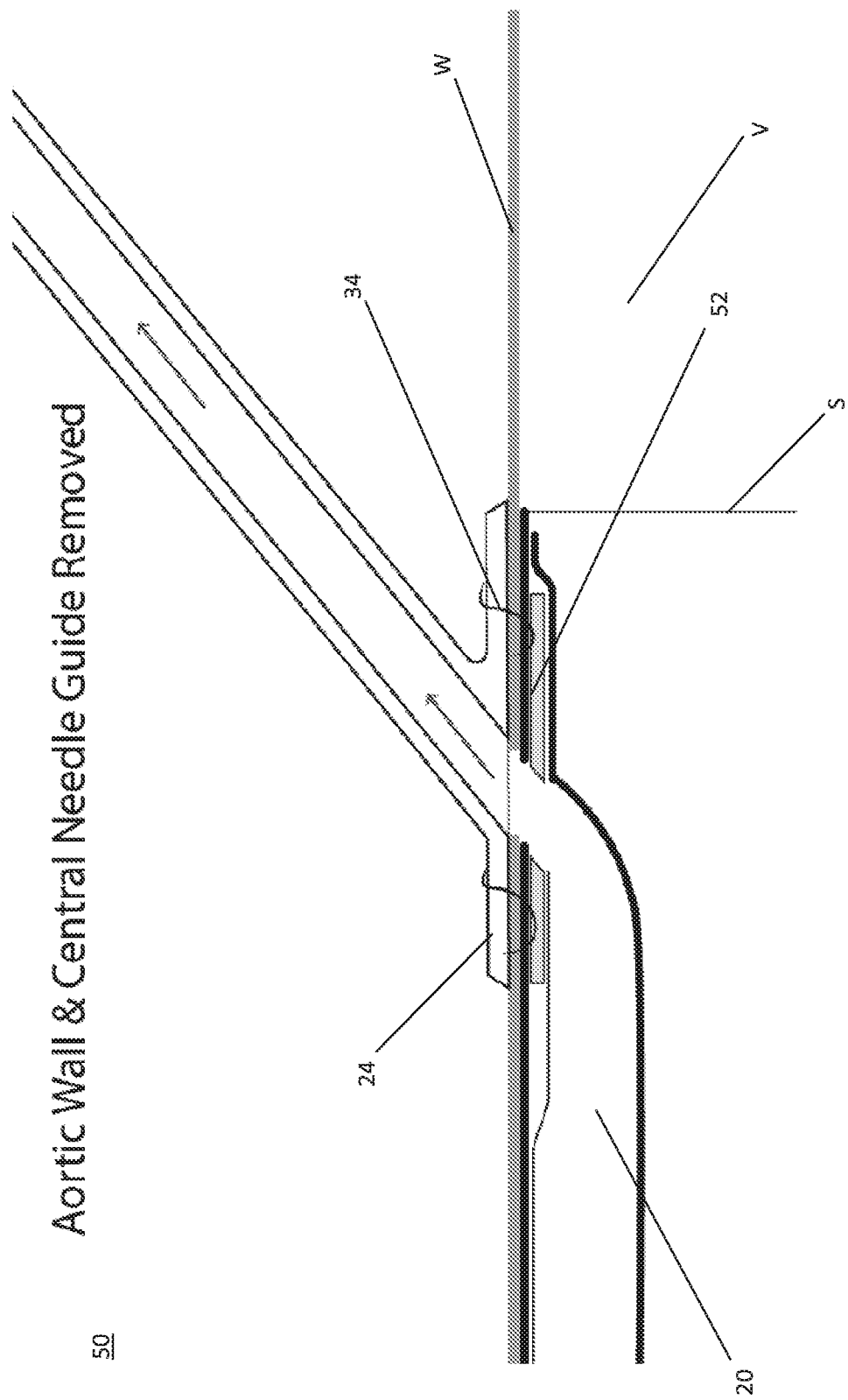
Figure 4A:
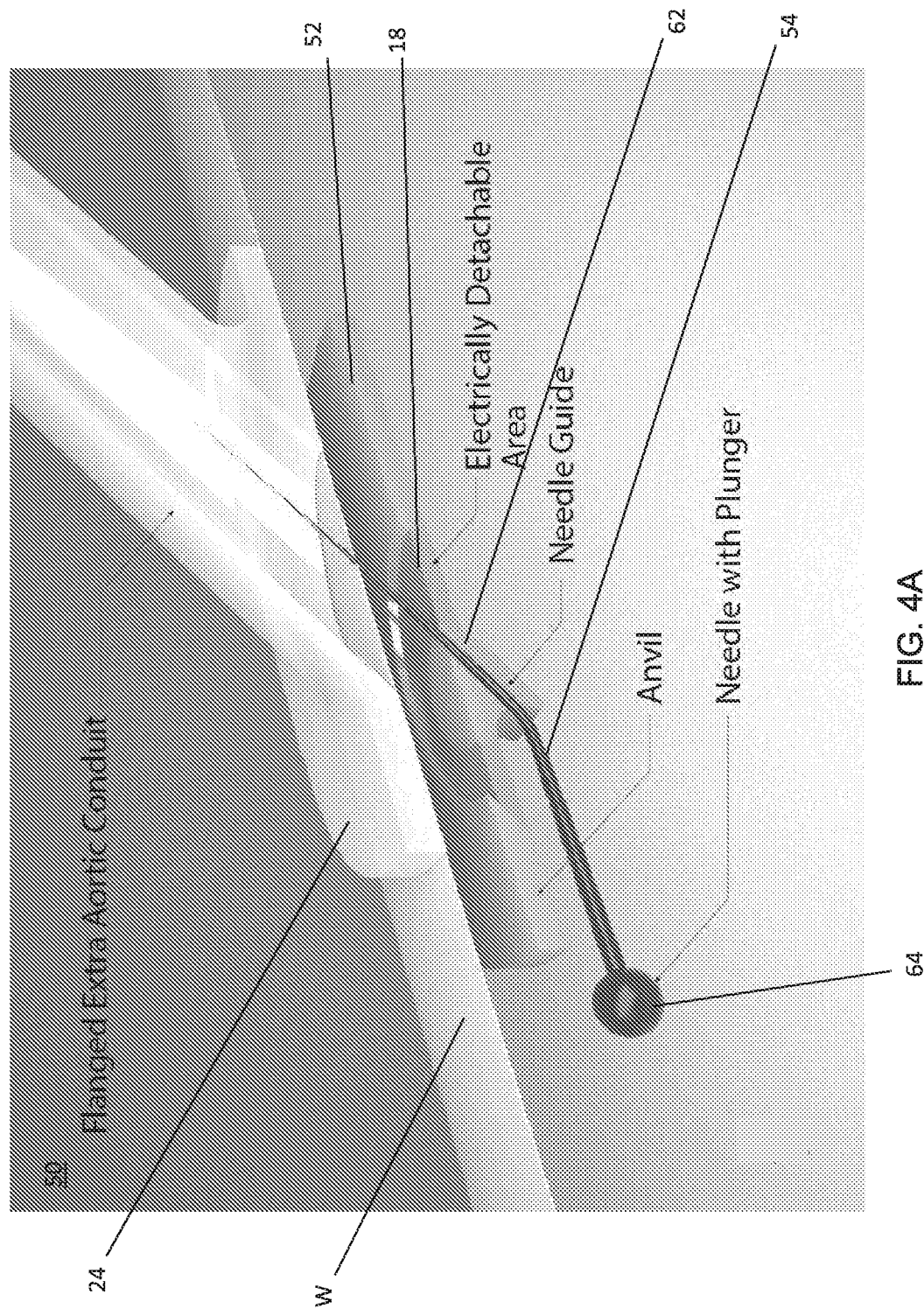
FIGS. 4A-4C are a series of perspective cross-sectional views of a needle and plunger to assist in the implantation and deployment of a cardiac assist device in accordance with embodiments of the invention.
Figure 4B:
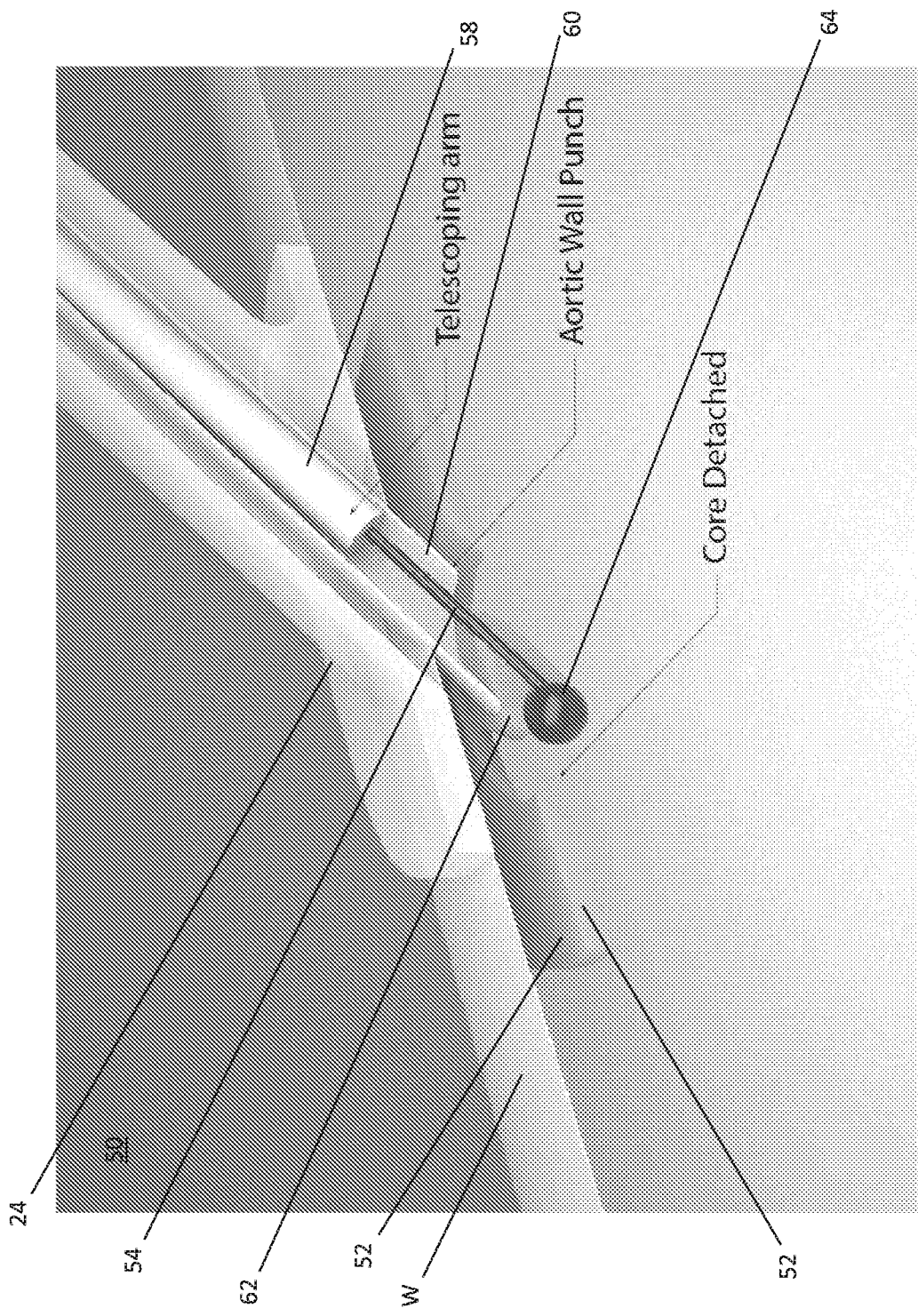
Figure 4C:
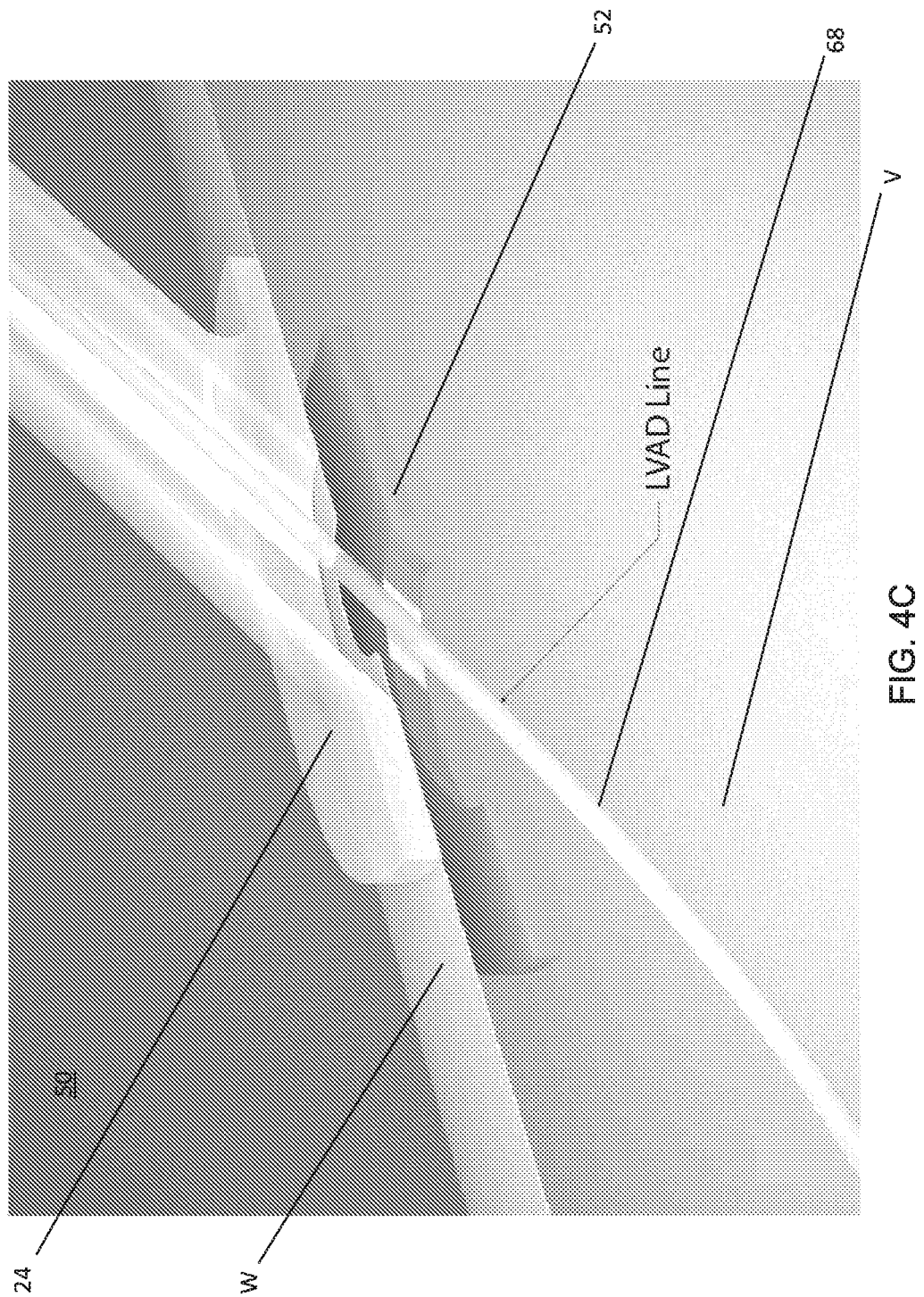

An embodiment of a system 50 for the attachment and deployment of a cardiac blood pump, or permanent blood pump is described in FIGS. 3A-3I as cross-sectional views and in FIGS. 4A-4C as perspective cross-sectional views of a needle 54 and plunger 64 to assist in the implantation and deployment of a cardiac assist device in accordance with embodiments of the invention. As shown in FIG. 3A-1 and in greater detail in FIG. 3A-2 and FIG. 4A, an anvil 52 and needle guide 62 connected to a non-distensible collapsed sub-neo-intimal primary pumping element 20 (hereinafter referred to as pocket 20) are shown implanted along with a stent S in a patient vessel V illustratively including the aorta. Implantation of the endo-aortic securement anvil 52 and secondary luminal confinement 20 is via conventional methods that illustratively include the use of a vascular catheter. The plunger end 64 of needle 54 is connected to a detachable cable 56, where the cable 56 pulls on the plunger 64 and draws the needle 54 inward into the needle guide 62 where the needle guide 62 directs the needle 54 upward and outward toward the wall W of the vessel V so as to puncture the wall W as shown in FIG. 3B and FIG. 4A. In FIG. 3C a centering probe/telescope 58 is introduced into the patient and is firmly attached to the needle 54. In a specific embodiment the centering probe/telescope 58 is introduced into a patient via a percutaneous access device (PAD) 70 as shown in FIG. 5A. Subsequently, a flanged extra aortic conduit 24 is centered about the centering probe/telescope 58, with fine location placement determined via optional locating features 14 on the anvil 52 and complimentary locating features 32 on the stapler 30 that fits over the conduit 24. In an alternate embodiment, a fluid source for cardiac pump inflation is either a gas or a liquid that are driven periodically into the chamber 38 to create blood movement through a fluid drive system that is wholly implanted and powered by internal batteries or via an external wireless charging device In a specific inventive embodiment the locating features 14 as shown above in FIG. 1B may be a set of transponders, which may be passive or active, that react to the transmitted seeker signals from the complimentary location features 32 located on the securement device 30 in a similar manner to radio frequency identification RFID based technology. In a specific embodiment the complimentary location features 32 located on the securement device 30 are configured as a transponder/seeker that send signals to the locating features 14 configured as a receiver on the anvil 52. Additionally, other locating methods illustratively including light emitting diodes (LED), and fluormetry may be used for locating features or fiducial markings for aligning the conduit 24 with the anvil 52 to provide an access path into the vessel V. It is appreciated that in some embodiments, an anvil surface has a dimple to deflect a slightly misaligned probe 28 into contact the pole of a dimple.

In FIG. 3D the stapler 30 is placed about the conduit 24. In the embodiment shown the stapler 30, which as shown has a circular shape for providing staples 34 in a circular perimeter, to attach the flange portion of a conduit 24 through the wall W of the vessel V to the anvil 52. It is noted that other perimeter shapes illustratively including oval, square, rectangular may be used to secure the flange of the conduit 24 to the anvil 52. In FIG. 3E two or more staples 34 are deployed from the stapler 30. In a specific embodiment six staples 34 are deployed around the perimeter of the flange of the conduit 24 and anvil 52. As shown in FIG. 3E counter pressure on the anvil 52 is maintained by pulling up on the centering probe/telescope 58 in an embodiment as the staples 34 are bent upward and back by the anvil 52. In FIG. 3F a vascular wall punch 36 is introduced in the conduit 24 and cuts into and through the wall W. In FIG. 3G and FIG. 4B an electrically detachable ring 66 is exercised to free the needle guide 62. In FIG. 3H the cable 56 is electrically detached from the plunger 64. In FIG. 3I the punched section of the wall W is removed along with the now separated needle guide 62 through the conduit 24 to create a clear channel to the primary pumping element 20. FIG. 4C illustrates the introduction of an operational line 68 through the conduit 24 and into the vessel V.

FIG. 5A is a cross-sectional side view of a percutaneous access device (PAD) 70 implanted in a patient for providing a power or actuating connection 72 via conduit 24 to a ventricular assist device according to an embodiment of the invention. In a specific embodiment the PAD 70 through the skin surface layers (SL) illustratively including the epidermis, dermis, and subcutaneous tissue provides for a semi-permanent connection to an out-of-body power source or pump 78 as shown in FIG. 5D. As is described in greater detail in the prior patents incorporated herein by reference in their entirety, a tube or line 76 can be led from the implanted cardiac pump chamber to a percutaneous access device implanted and projecting through a patient's skin or have wholly implanted fluid drive system and sensor package Regardless of the nature of the fluid drive system. In some embodiments the fluid includes a marker that when permeating the chamber 38 is indicative of the membrane defining the chamber 38. A marker for a gaseous fluid illustrative includes a diatomic gas that is enriched in either the ortho or para isomers. In a specific embodiment, the diatomic gas is hydrogen that is detected in MRI devices. In still other embodiments, the diatomic gas is isotopically enriched. In instance when the fluid is a liquid, conventional detectable markers are used for detection by techniques illustratively including MRI, ultrasound, and X-ray spectroscopies. It is appreciated that a sensor to detect cardiac pump chamber inflation pressures and/or other operation parameters is readily provided in communication with the fluidics.

The percutaneous access device allows the tube and leads as needed for sensors or other operational aspects, to be operatively connected to or disconnected from an external fluid drive system and controller. In operation, the secondary pumping element 38 or multiple such chambers are each independently cyclically inflated and deflated with a pressurized fluid with a synchronicity relative to the patient heart. Preferably, the synchronous cyclical inflation and deflation can be based on a set of programmable patient parameters relating to heart function. The fluid driver 78 may supply an inflation fluid as either a gas or a liquid to expand the cardiac pumping chamber 38 within the primary pumping element 20 of the ventricular assist device. It is appreciated that gases other than air are operative with the present invention to induce pump inflation. These gases illustratively include helium, nitrogen, argon, and mixtures thereof. While these gases have lower viscosities than air, such gases necessitate tethering the recipient of an inventive blood pump implant to a compressed gas tank thereby reducing the mobility of the recipient. In a specific embodiment a tracer may optionally be added to the fluid to detect a compromised membrane of the expandable primary pumping element 20. Other fluids such as saline or other hydraulic fluids can serve to actuate the pumping chamber; optionally, a tracer substance such as indocyanine green or fluorescein can be included in the hydraulic liquid for detection of leaks from the pumping chamber.

Optionally, feedback sensors are provided for the operation of an inventive blood pump. Such sensors illustratively include a pressure transducer, an accelerometer, a strain gauge, an electrode, and species specific sensors such as pH, oxygen, creatine, nitric oxide or MEMS versions thereof. The output of such a sensor being transmitted as an electrical or optical signal to monitoring and regulatory equipment exterior to the body of the recipient.

Embodiments of the inventive cardiac pump alone or a plurality of such pumps in the aggregate displaces from about 20 to 70 cubic centimeters of blood upon inflation; each alone or collectively when several chambers are implanted and operating collectively. In a particular inventive embodiment, 50 to 70 cubic centimeters of blood are displaced per heartbeat by the present invention so as to allow an individual having an inventive pump implanted an active lifestyle. In still other embodiments, 60 to 65 cubic centimeters of blood per patient heartbeat by the present invention. The long axis of the primary pumping element and the pumping chamber are aligned along the long axis of the aorta. Alternatively, the pumping chamber is symmetric in at least two orthogonal axes, or the pumping chamber long axis extends helically or in some other non-linear form in a local segment of the aorta.

FIG. 5B illustrates the use of an implanted transcutaneous energy transfer module (TET) for providing one or more power or actuating connections (72, 72') via conduits 24 that are connected to one or more cardiac assist devices according to an embodiment of the invention. In a specific embodiment two or more ventricular assist devices may be placed in an aorta of a patient.

Figure 5C:
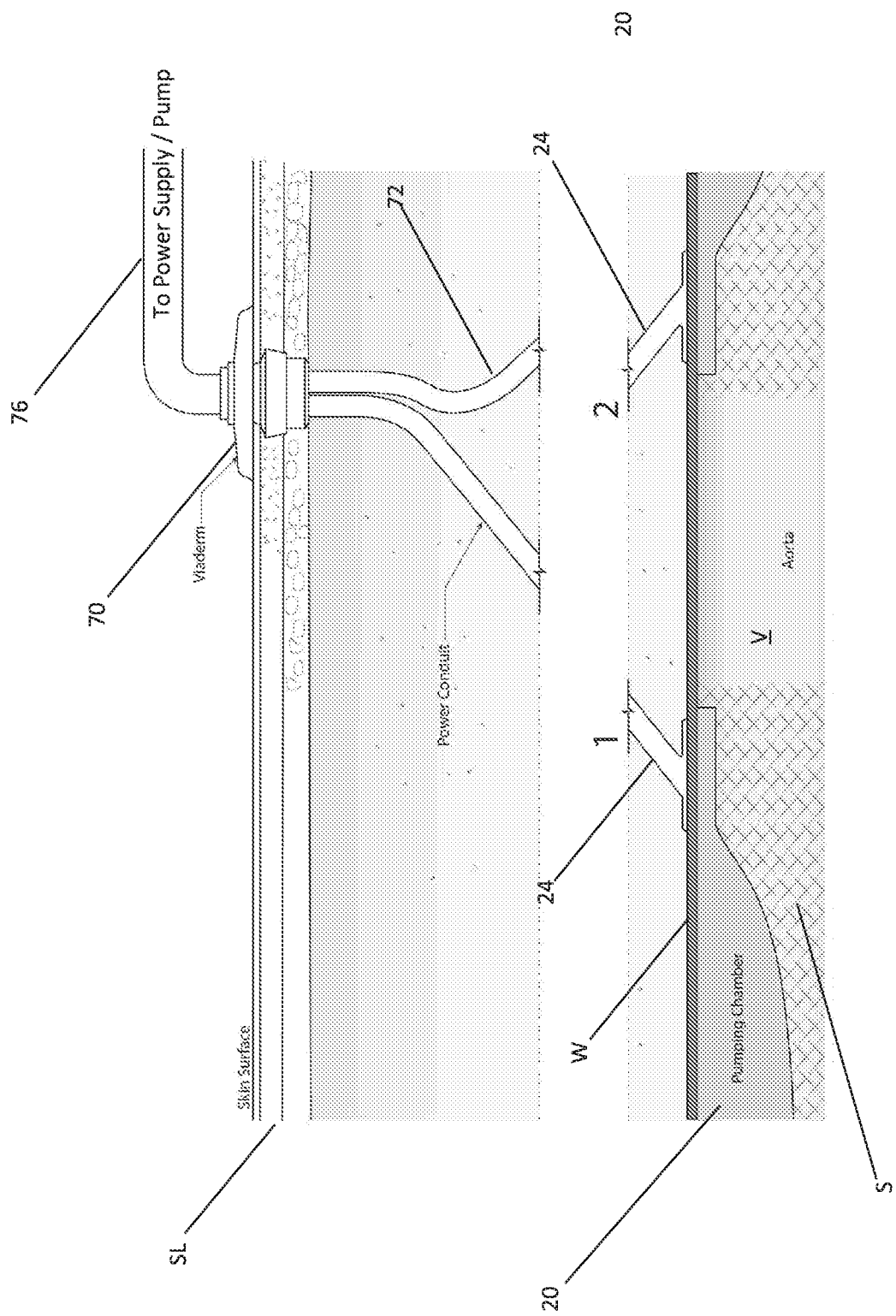
FIG. 5C illustrates a cross-sectional side view of a single percutaneous access portal implanted in a patient for providing a power or actuating connection to two cardiac pumps according to an embodiment of the invention.

FIG. 5C illustrates multiple power or actuating connections 72 emanating from a single PAD 70 that is connected to an external power supply pump 78 via external line 76.

Figure 5E:
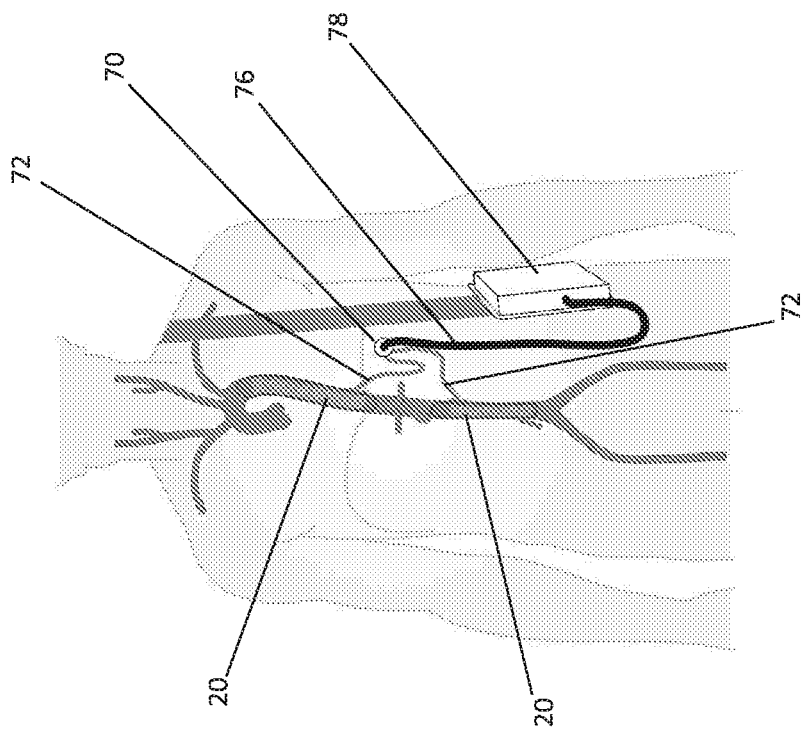
FIG. 5E illustrates an external power source or pump connected via a percutaneous access device to multiple cardiac assist devices as is shown in FIG. 5C according to an embodiment, of the invention.
Figure 5D:
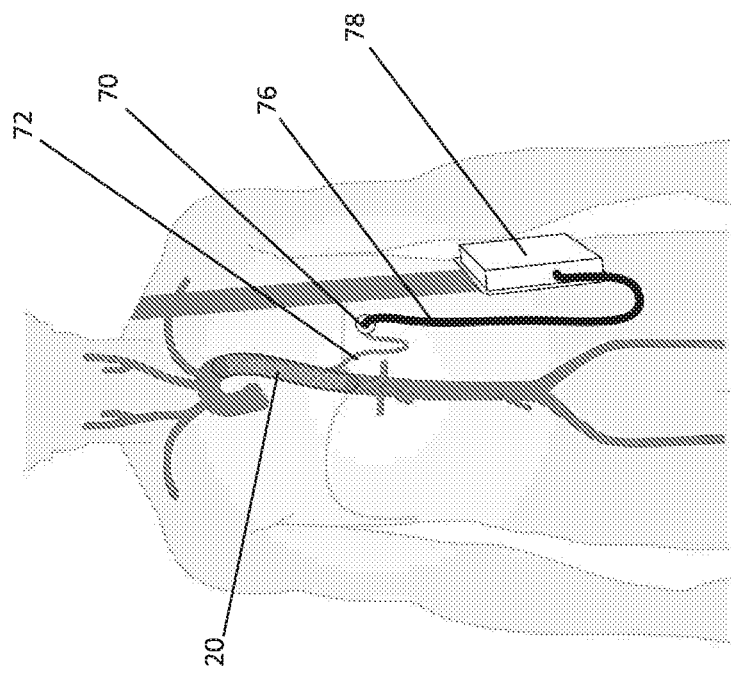
FIG. 5D illustrates an external power source or pump connected via a percutaneous access device to a cardiac assist device according to an embodiment of the invention.

FIG. 5E illustrates an external power source or pump 78 connected via a single percutaneous access device 70 to multiple cardiac assist devices 20 as is shown cross section in FIG. 5C.

Figure 5H:
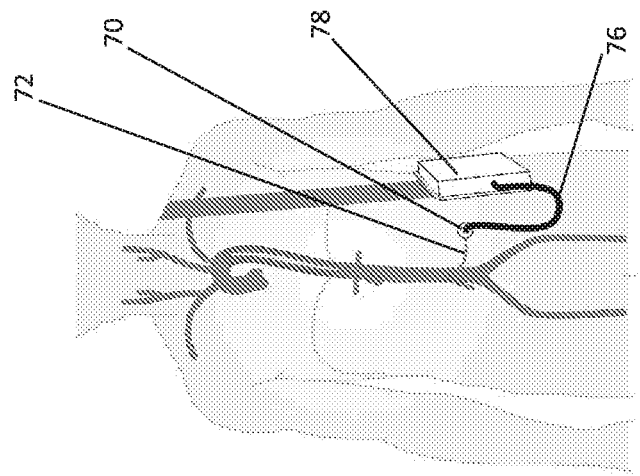
FIGS. 5G and 5H illustrate alternative positioning of the percutaneous access device and ventricle access points to the cardiac assist device in the aorta.
Figure 5G:
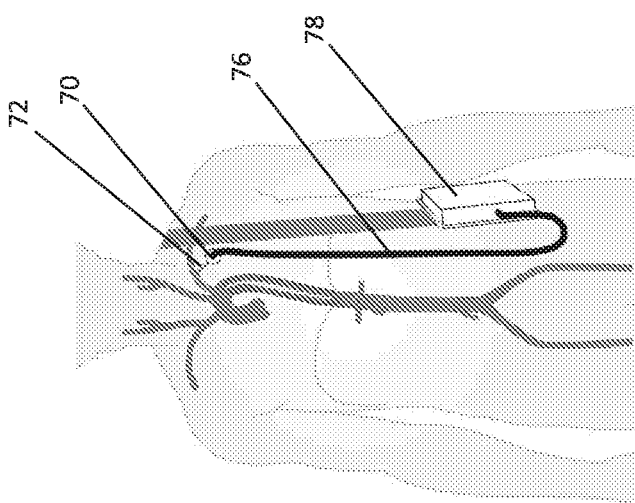
Figure 5F:
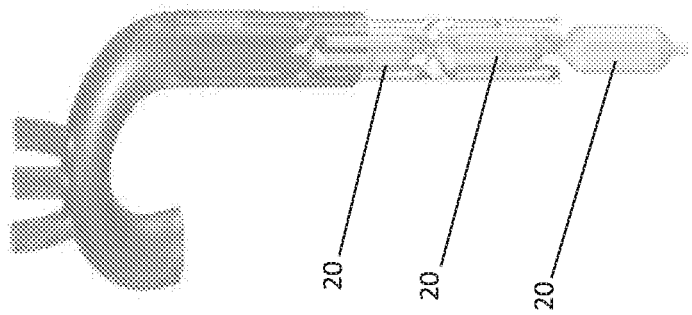
FIG. 5F illustrates multiple ventricular assist devices in a patient aorta in accordance with embodiments of the invention.

FIG. 5F illustrates multiple cardiac assist devices 20 along the aorta of a patient. It is appreciated that multiple cardiac pump chambers are synchronized together to blood flow in the aorta, with each of the multiple devices 20 have an independent fluid source and drive system, else two or more cardiac pump chambers are manifolded to share a single fluid source and/or drive system.

FIGS. 5G and 5H illustrate alternative positioning of the percutaneous access device 20 on the subjects' body and ventricle access points to the cardiac assist device in the aorta.

FIGS. 6A-6F are a series of cross-sectional side views showing the implementation and actuation of a cardiac assist device in accordance with embodiments of the invention. In FIG. 6A an initial stent S and primary pumping element 20 with a securement 12 are placed in the vessel V of the patient. Optical coherence tomography (OCT) is a recently developed technology that uses infrared light to generate micrometer-scale cross-sectional images (*Science*. 1991; 254:1178-1181). OCT is optionally used in the present invention to assess the microstructure of the aortic wall in the intended region of device placement to avoid fixturing of a device proximal to an aortic wall defect. Typically, OCT resolutions of 4 to 16 µm are adequate to assess aortic wall integrity. OCT is readily performed using a conventional intravascular OCT endoscope. It is appreciated that OCT with a micromotorcatheter affords high frame per second imaging, while MEMS-tunable vertical cavity surface emitting laser (VCSEL) OCT has still other advantages in terms of miniaturization and imaging quality (T-H Tsai et al, "Ultrahigh speed endoscopic optical coherence tomography using micromotor imaging catheter and VCSEL technology" Biomed Opt Express. 2013 Jul. 1; 4(7): 1119-1132.). OCT is also readily combined with fluorescent contrast for intravascular atherosclerotic imaging or embolism imaging.

In FIG. 6B a conduit 24 is secured to the securement 12 and the wall W of the vessel V. In FIG. 6C a clear channel is created between the conduit and the primary pumping element 20. In FIG. 6D the pumping chamber 38 is introduced into the expandable primary pumping element 20. FIG. 6E illustrates the state of the vessel V when the pumping chamber 38 is deflated, and FIG. 6F shows the state of the vessel with volume displacement with the pumping chamber 38 inflated in the primary pumping element 20.

In some inventive embodiments a vacuum source is applied to the pumping chamber 38 or the interstitial space between the primary pumping element 20 and the pumping chamber 38. Periodic vacuum application is readily applied for an extended period of time with limited or no inflation or as part of a pump inflation cycle. Vacuum application is used for various functions illustratively including microleak detection in the primary pumping element 20 or the pumping chamber 38, as well as promoting evaporation of condensate.

FIGS. 7A-7D illustrate an endovascular procedure where the components for an aortic assist device may be delivered in two stages with the elimination of the stage that introduces the secondary lurninal confinement (expandable primary pumping element) 20. It is appreciated that the elimination of the secondary luminal confinement leads to a less invasive procedure for both the initial implantation, and for the potential future replacement of the aortic assist device. It is also appreciated that a stent may also be introduced at the insertion site of aortic assist device 80, but is left out for clarity in the drawings.

Figure 7A:
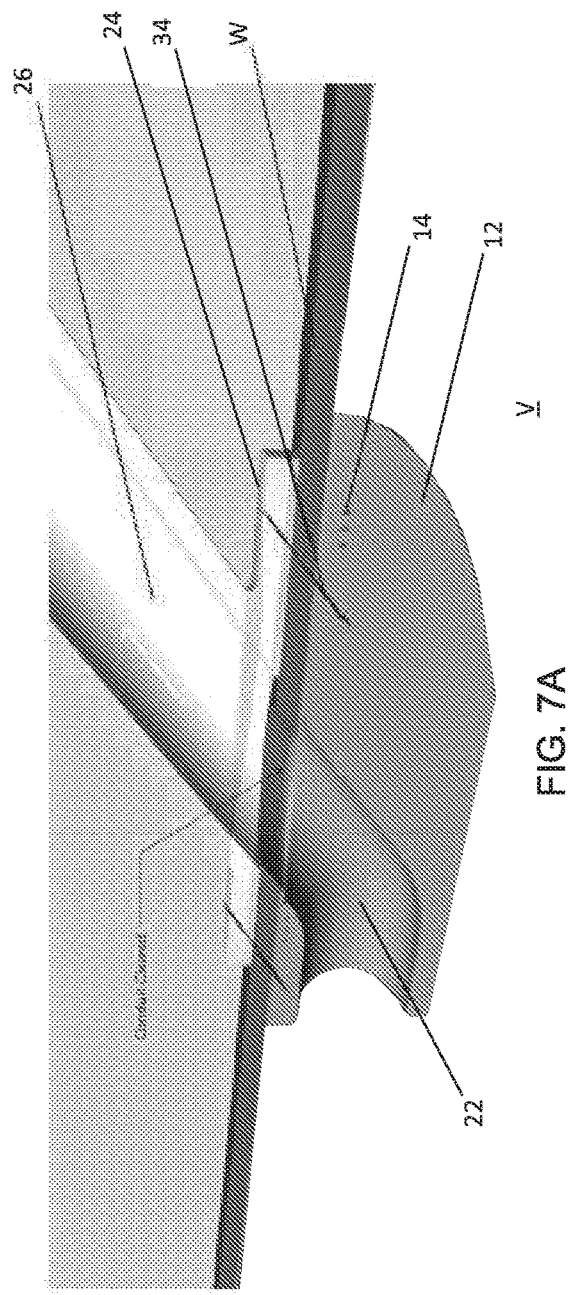
Figure 7B:
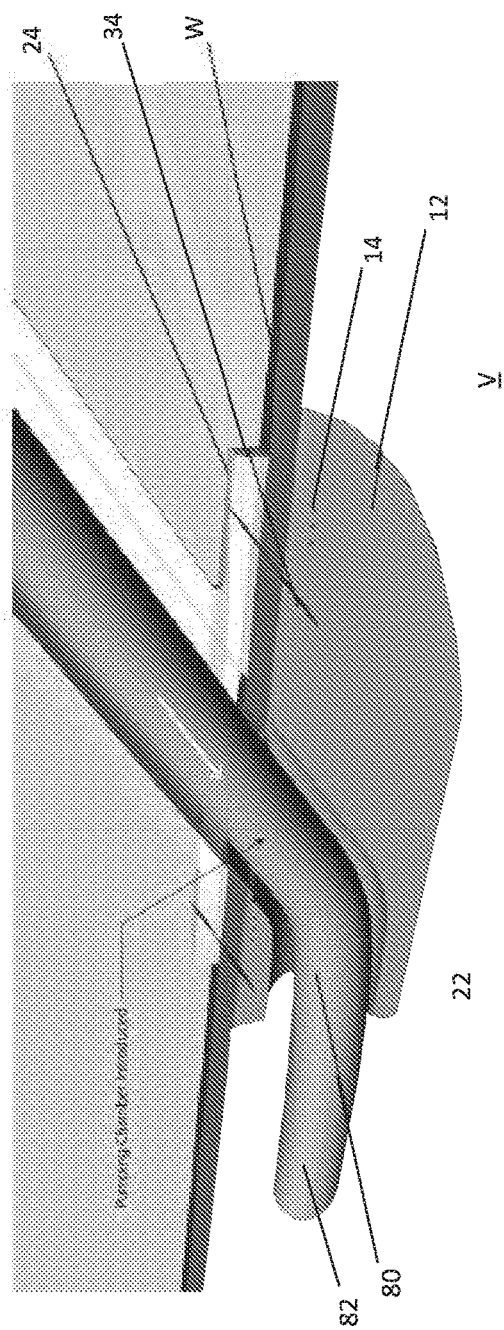
Figure 10A:
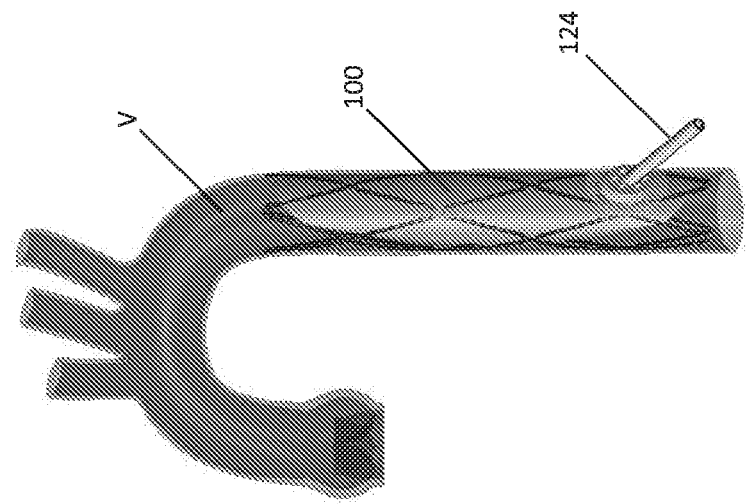
Figure 10B:
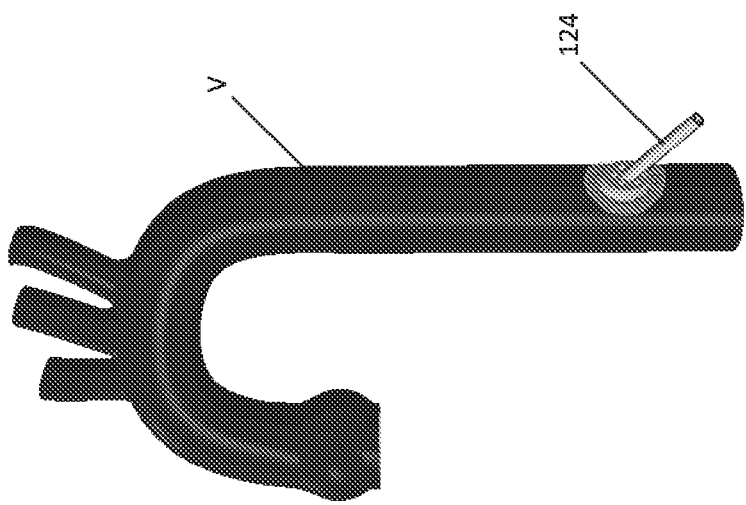
Figure 10C:
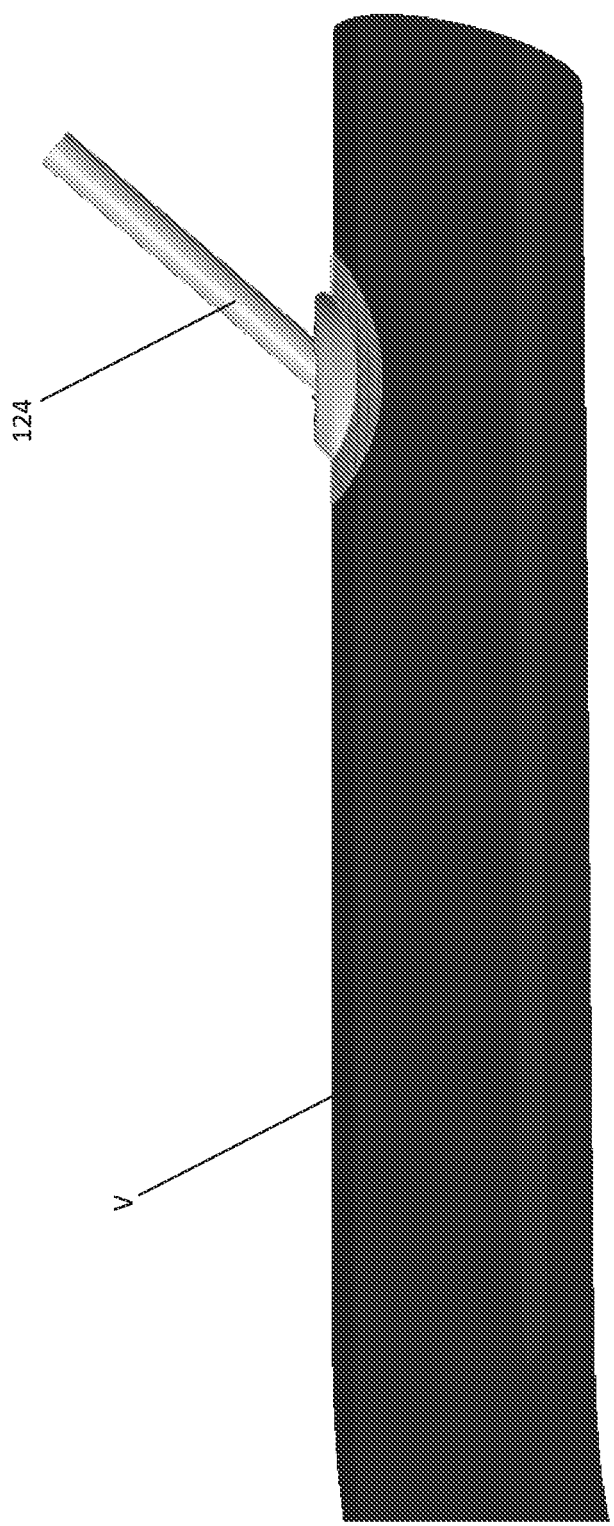
Figure 10G:
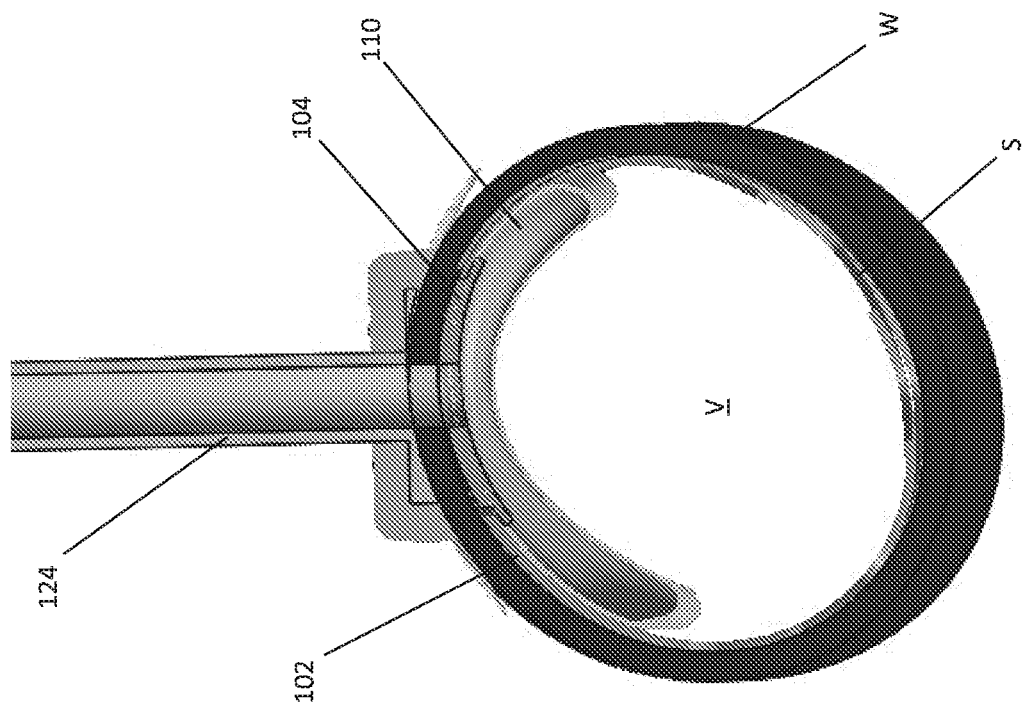
Figure 10H:
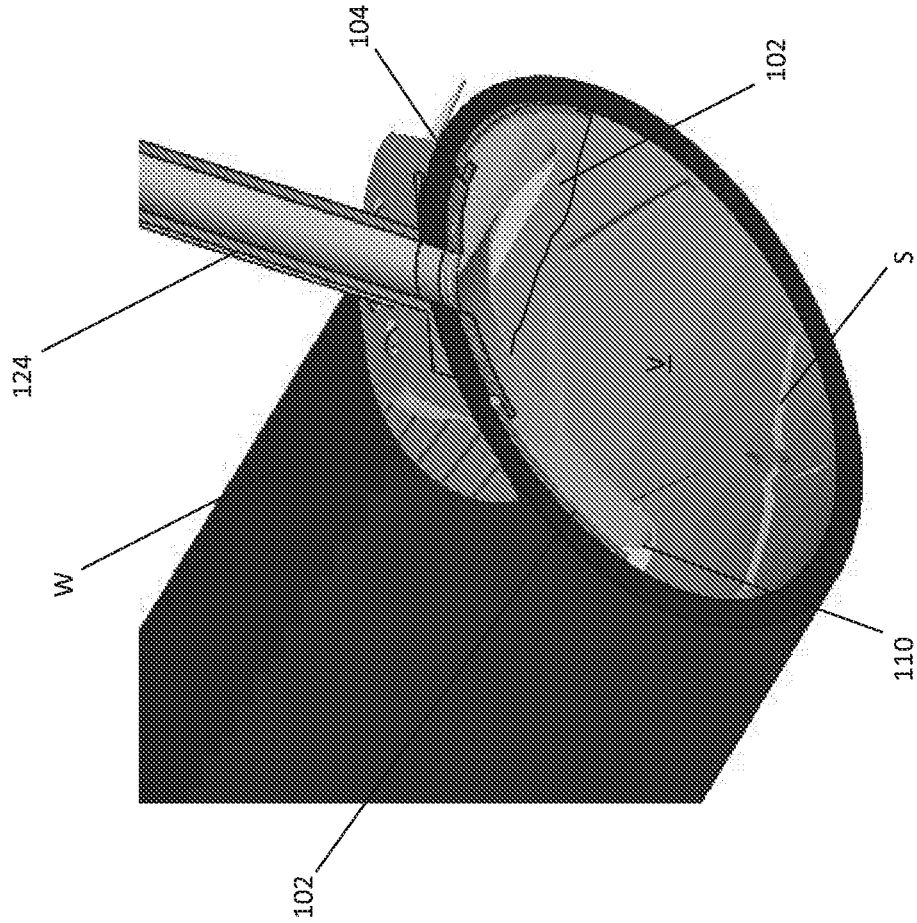
Figure 10I:
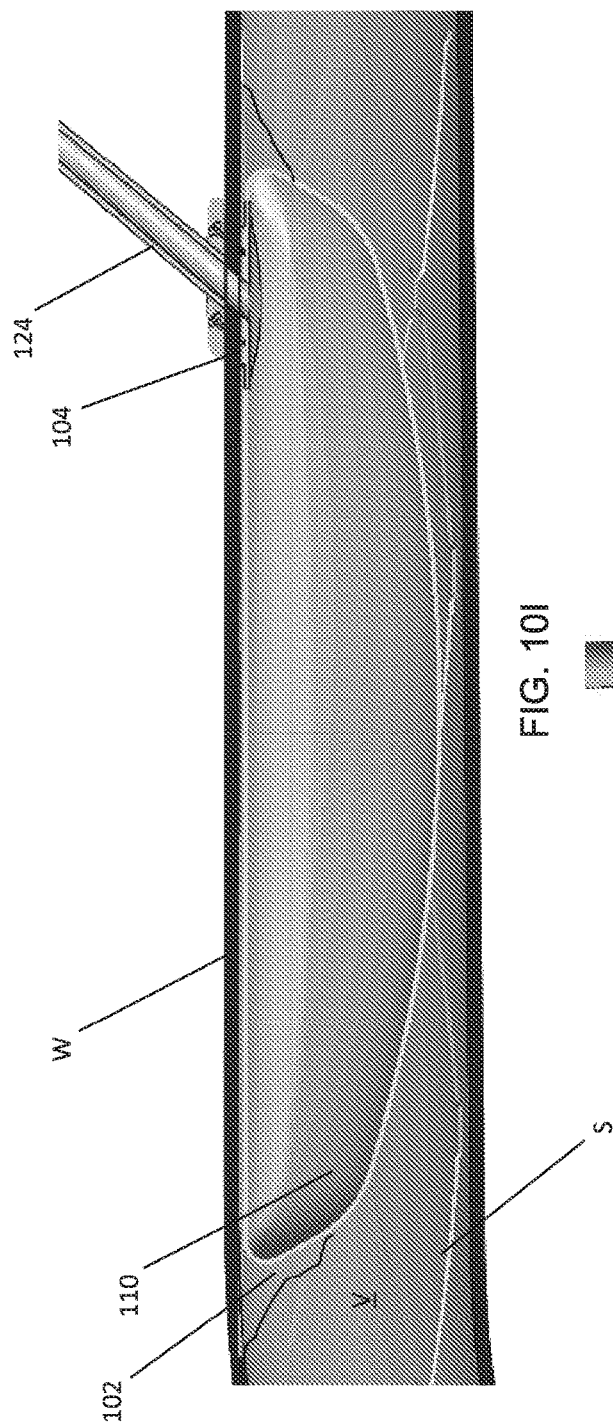
Figure 10J:
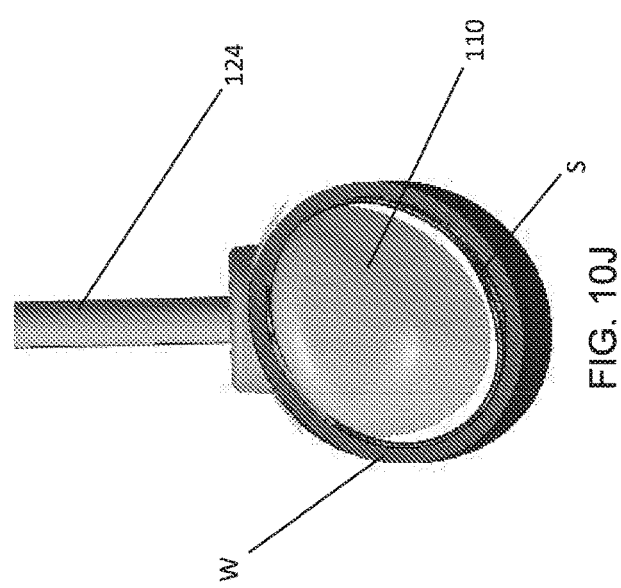
Figure 10K:
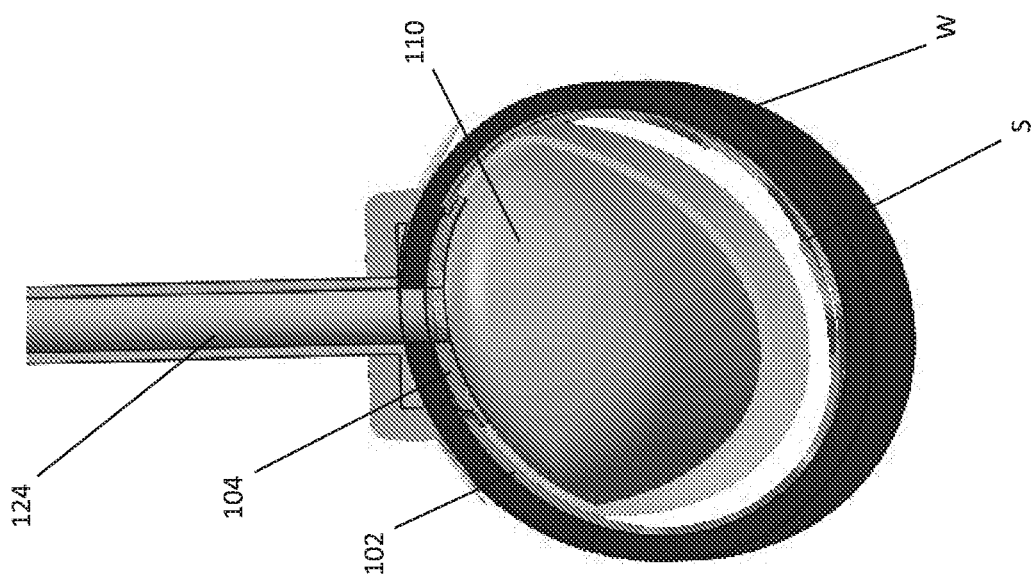
Figure 10L:
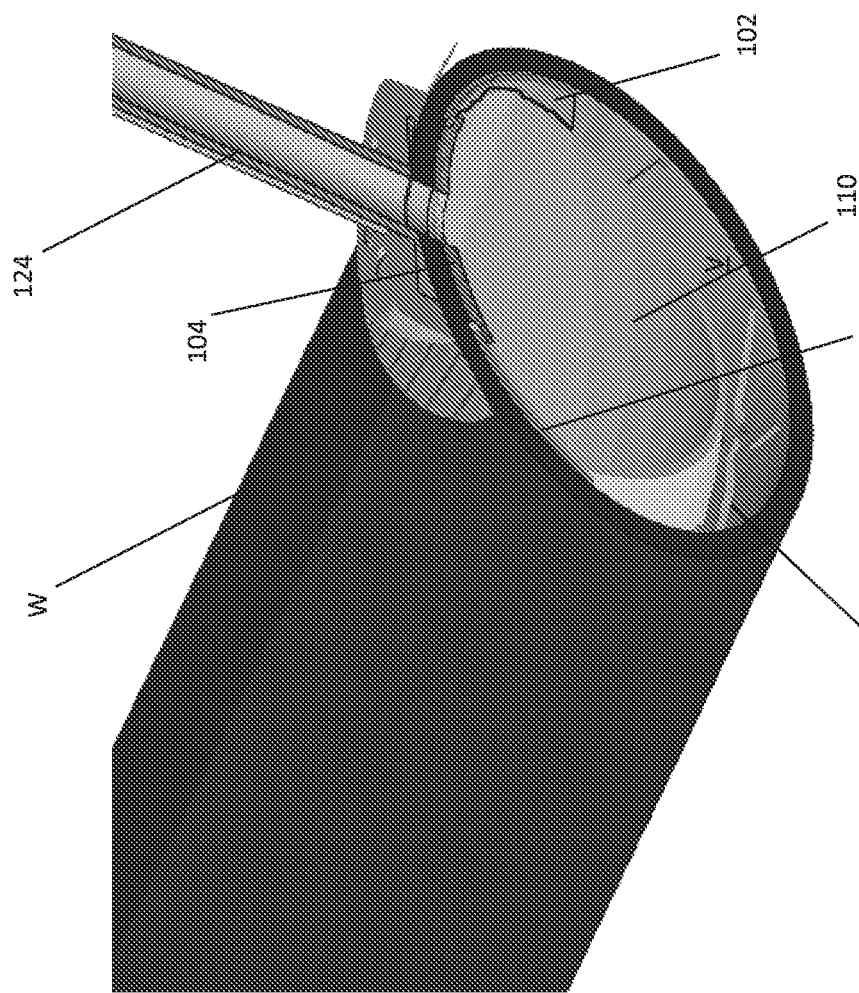

In the first stage, the securement 12 is delivered into the vessel (V), for example by a groin catheter The second stage introduces the aortic assist device 80 with a flexible encasement 82 and a balloon 84 inside, and may enter the vessel via the extra aortic conduit 24 after the flange of the conduit 24 is mounted to the securement 12 to deliver the aortic assist device 80 through the conduit 24. FIG. 7A illustrate the joining of the securement 12 to the flange of the conduit 24 via methods as described in the embodiments above to form an access channel that includes aperture 26 and introductory guide channel 22. In FIG. 7B, the delivery of the primary pumping element, synonymously referred to with respect to FIGS. 7B-8B as a flexible encasement 82 occurs exovascularly through the access channel. In FIG. 7C, the encases t 82 in a deflated state is fully inserted in the vessel with the insertion line 40 that is now visible. In a specific embodiment, the flexible encasement 82 and insertion line 40 are introduced into a patient via an embedded percutaneous access device (PAD) 70 as shown in FIG. 5A. FIG. 7D illustrates the inflation of the encasement 82 via inflation of the balloon 84.

FIGS. 8A and 8B are cross-sectional views of the aortic assist device 80 with a flexible encasement 82 and the balloon 84 inside (shown in dotted lines). The flexible encasement 82 protects the balloon from the blood flow in the vessel, and guards against a potential failure of the balloon 84. In FIG. 8A the balloon 84 is in a deflated state, and in FIG. 8B the balloon 84 is inflated.

It is appreciated that the flexible encasement 82 may be readily treated with a primary coating. Such coating substances illustratively include heparin, antibiotics, radiopaque agents, anti-thrombogenic agents, anti-proliferative agents, anti-angiogenic agents; each alone, or in combination. It is further appreciated that a secondary coating overlying the first coating is provided to promote sustained release of the underlying coating substance. Such secondary coatings illustratively include polylactic acid, polyglycolic acid, polyethylene oxide, polycaprolactone, polydioxanones, combinations thereof, and co-polymers thereof.

In certain inventive embodiments, the flexible encasement 82 may be formed from a material that induces immunocompatible granulation tissue overgrowth thereon or in-growth therein to effectively render the secondary luminal confinement 20 non-provocative from thrombotic events against the adluminal surface of the flexible encasement 82. Coatings operative herein illustratively include poly-L-lysine (PLL), polylmethyl coguanidine-cellulose sulphate (PMCG)-CS/PLL-sodium alginate (SA), polyethyleneimine, poly(dimethyldiallylammonium chloride), chitosan, polyacrylacid, carboxymethylcellulose, cellulose sulfate, pectin, and combinations thereof to form multilayers. It is appreciated that such coatings are readily impregnated with compounds that reduce the immune cascade, these illustratively include heparin and factor H.

FIGS. 9A-9D are a series of perspective and cross-sectional views of an aortic assist device 100 integrated with a stent S for delivery into an artery in accordance with an embodiment of the invention. The aortic assist device 100 has an elongated shell 102 integrated with the stent S. The shell 102 has a concave shape that is transverse to the length dimension of the shell 102, where the concave shape is modeled after the cross-sectional shape of the artery in which the aortic assist device 100 will operate. A portal 104 on the surface of the shell 102 serves as an attachment point for the exo-aortic conduit 124 that is shown in FIGS. 10A-10L. Seal 108 is removed to gain access to the expandable chamber 110 as shown in greater detail in FIG. 10F. Seal 108 aligns with the channel 125 of the conduit 124. Holes 106 on the surface of the portal 104 serve as entry points for fasteners 126. Once the aortic assist device 100 is delivered into the vessel (V), for example by a groin catheter, and is positioned in the aorta, the exo-aortic conduit 124 is attached to the portal 104 and external connections to a pump 78 are established as described above with respect to FIGS. 5A-5H.

FIGS. 10A-10L are a series of perspective and cross-sectional views showing the implementation and actuation of the aortic assist device 100 shown in FIGS. 9A-9D. FIGS. 10D-10H show the expandable chamber 110 in a deflated state. FIGS. 10I-10L show the expandable chamber in an expanded inflated state.

Figure 11A:
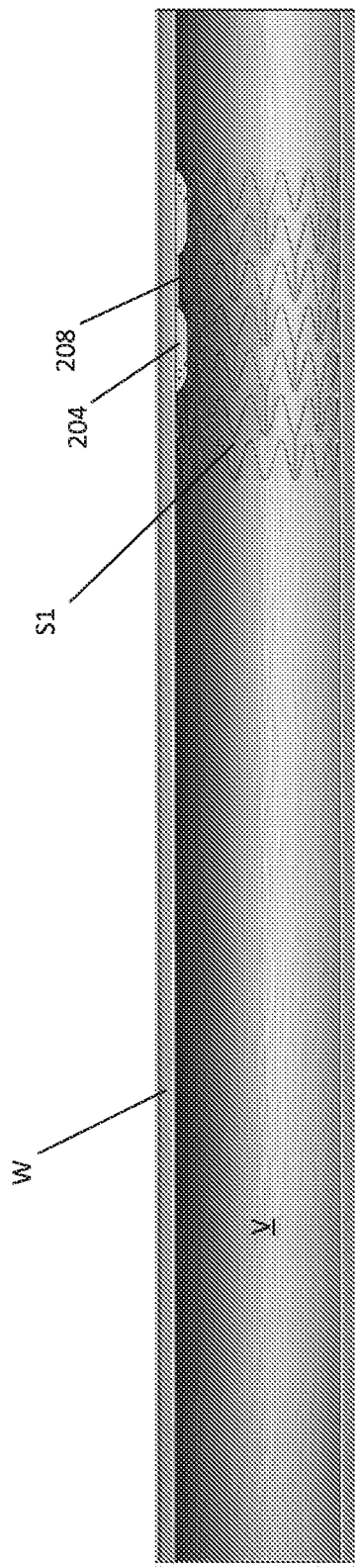
FIGS. 11A-11P are a series of cross-sectional side views showing the implementation and actuation of a ventricular assist device in accordance with embodiments of the invention.
Figure 11B:
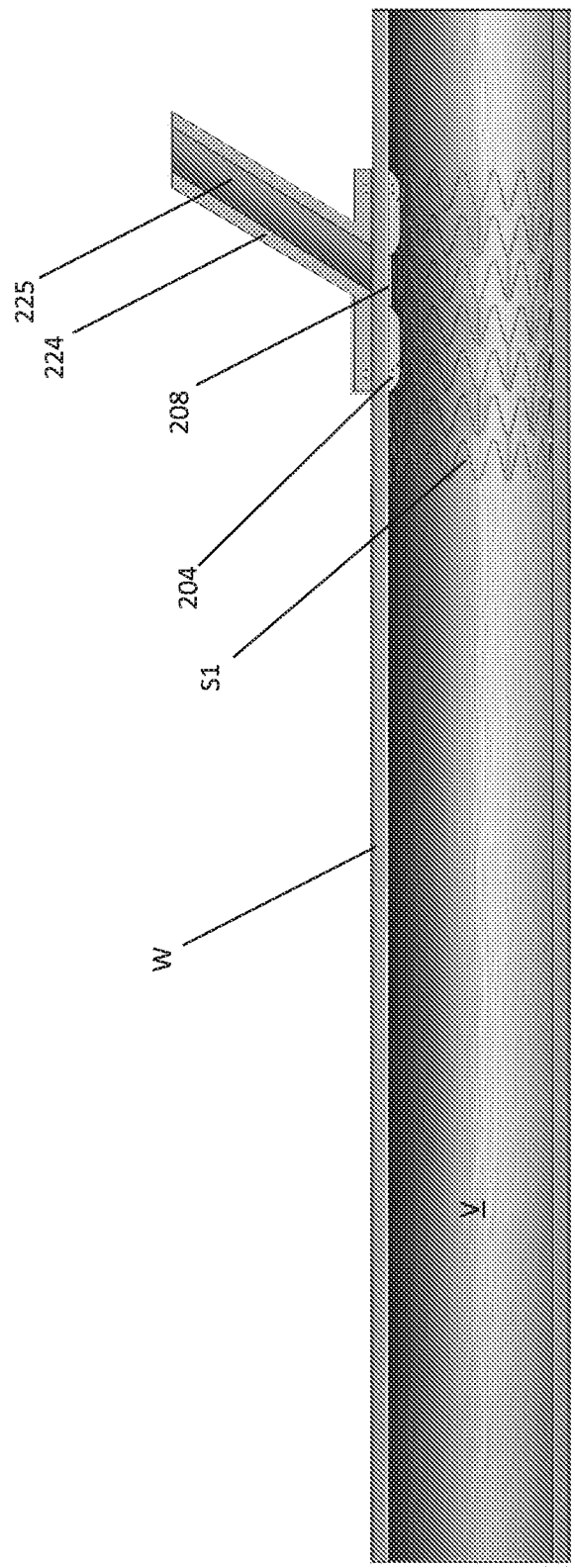
Figure 11E:
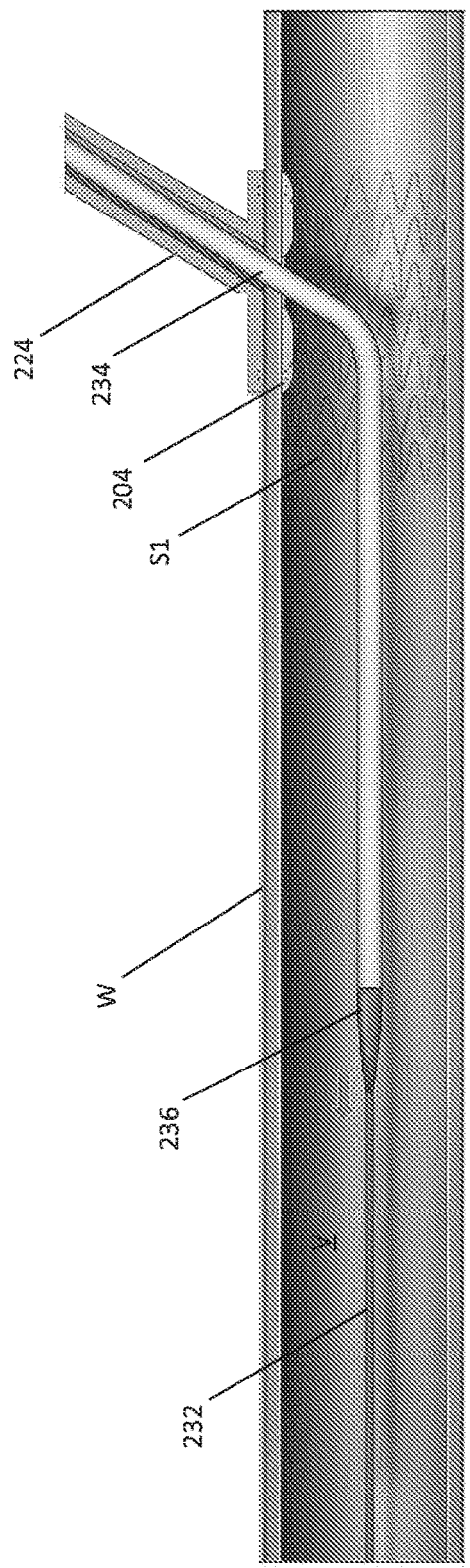
Figure 11F:
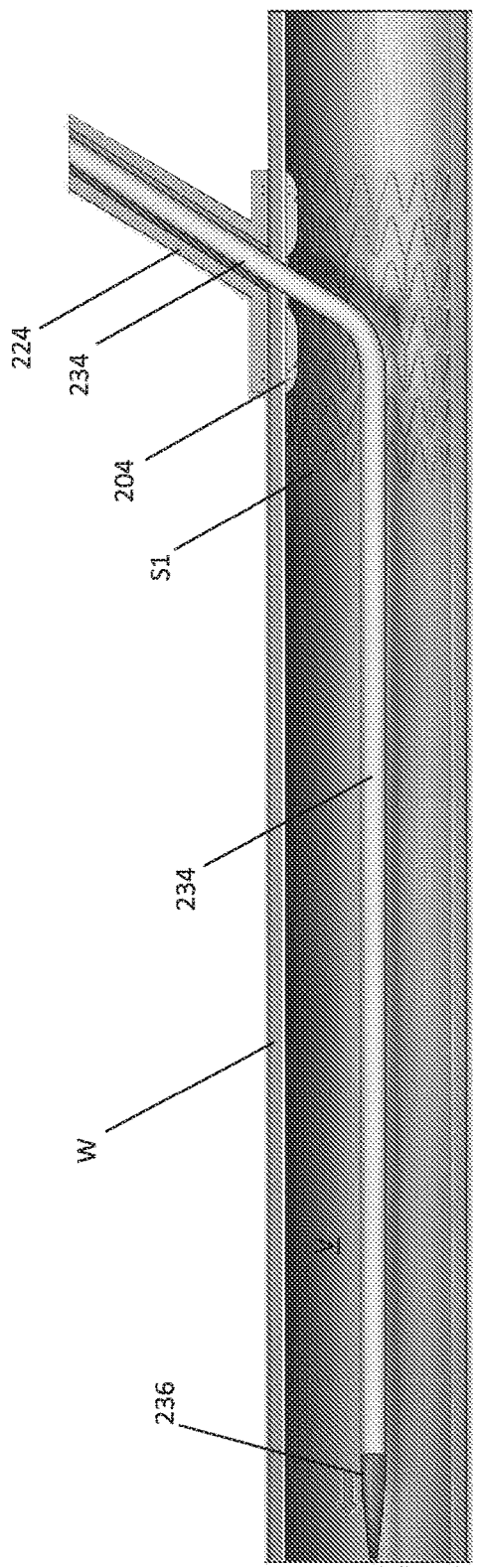

FIGS. 11A-11P are a series of cross-sectional side views showing the implementation and actuation of a ventricular assist device in accordance with embodiments of the invention. In FIG. 11A a first stent S1 is introduced and positioned in the artery V. Integrated to the stent is an attachment disk 204 with a removable seal 208. In FIG. 11B the seal 208 is aligned with the channel 225 of the conduit 224. The conduit 224 may be joined to the attachment disk 204 as described previously with respect to FIG. 1 and FIG. 2. In FIG. 11C a coaxial aortic punch 230 with a guide wire 232 are advanced via the channel 225 and through the wall W of the artery V and seal 208. As shown in FIG. 11D once the coaxial aortic punch 230 is centered in the artery V a guide wire 232 is advanced into the artery V. In FIGS. 11E and 11F an introducing sheath 234 with a detachable conical tip 236 is advanced into the artery V along the guide wire 232. In FIGS. 11G and 11H the introducing sheath 234 is retracted to expose and deploy an expanding second stent S2 and an expandable chamber 238. The expandable chamber has a thicker upper surface 240 that does not expand (stretch) or apply pressure on the wall W of the artery V. The interior facing lower surface 250 of the expandable chamber 238 is thinner and does expand (stretch). In FIG. 11I as the introducing sheath 234 exits the artery V the proximal end of the thicker upper surface 240 engages a grove 248 in the attachment disk 204 with a tongue 254 (see FIG. 11L for an expanded view). In FIGS. 11J and 11K as the detachable conical tip 236 is retracted with the introducing sheath 234 back through the channel 225 of the conduit 224 a liner portion 252 of the expandable chamber 238 expands against the walls of the channel 225. In FIG. 11k with the removal of the guide wire 232 a lower sealing arm 246 is allowed to articulate upward and tongue 254 on the lower sealing arm 246 engages the grove 248 in the attachment disk 204 to complete a sealed connection between the expandable chamber 238 and the attachment disk 204. In FIG. 11M the tip on the inflatable balloon 254 begins to become visible as the balloon 254 is introduced into the lined channel 225. In FIG. 11N as the balloon 254 advances into the expandable chamber 238, the insertion line 256 attached to the balloon 254 becomes visible in the lined channel 225. In FIG. 11O the deflated balloon 254 is fully inserted and seated in the expandable chamber 238. In FIG. 11P the expandable chamber 238 is in an expanded state with inflation of the balloon 254.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A cardiac assist device comprising:
a primary pumping element that forms an expandable pocket in mechanical communication with a securement positioned within a stent, where said primary pumping element and the stent are configured for placement within a vessel of a patient via an exovascular catheter;
a conduit external to the vessel, said conduit joined to said securement through a wall of the vessel;
at least one locating feature on said securement; and
a secondary pumping element insertable into said primary pumping element, said secondary pumping element is introduced into the patient via a percutaneous access device and through a wall of the vessel at the location of said securement.

2. The cardiac assist device of claim 1 wherein said primary pumping element is expandable and non-distensible.

3. The cardiac assist device of claim 1 further comprising a securement device fitting around said conduit, said securement device having complementary location features to the at least one locating feature on said securement.

4. The cardiac assist device of claim 1 wherein said conduit has an aperture configured for insertion of an alignment probe therethrough.

5. The cardiac assist device of claim 1 wherein the at least one locating feature is a transponder, a radiofrequency identification (RFID) tag, a light emitting diode (LED), an ultrasonic probe, a fiducial marker, or a combination thereof.

6. The cardiac assist device of claim 1 further comprising a sensor to detect an inflation pressure in said secondary pumping element.

7. The cardiac assist device of claim 1 wherein said securement has an aperture adapted to receive said primary pumping element via the exovascular catheter.

8. The cardiac assist device of claim 1 further comprising a stabilization/alignment target attached to said securement a detachable ring.

9. The cardiac assist device of claim 1 wherein said conduit further comprises a flange portion.

10. The cardiac assist device of claim 1 further comprising a fluid supply in fluid communication with an interior of said inflatable cardiac pumping chamber and at least one of a pump modifying a pressure of fluid in said secondary pumping element with a periodicity to aid in blood movement through the vessel or a transcutaneous energy transfer module modifying a pressure of fluid in said secondary pumping element with a periodicity to aid in blood movement through the vessel.

11. The cardiac assist device of claim 1 further comprising an immuno-isolation coating on said expandable primary pumping element.

12. A cardiac assist device comprising:
at least two expandable primary pumping elements that each separately form an expandable pocket, each of said at least two expandable primary pumping elements in mechanical communication with a securement positioned within a stent, where said at least two expandable primary pumping elements and each stent are configured for placement within a vessel of a patient via an exovascular catheter;
a first conduit external to the vessel, said first conduit joined to a first securement through a wall of the vessel;
a second conduit external to the vessel, said second conduit joined to a second securement through a wall of the vessel;
at least one locating first feature on said first securement;
at least one locating second feature on said second securement;
a first secondary pumping element insertable into a first of said at least two expandable primary pumping elements;
a second secondary pumping element insertable into a second of said at least two expandable primary pumping elements; and
wherein said first secondary pumping element and said second secondary pumping element are introduced into the patient via a percutaneous access device and through a wall of the vessel at the location of said first securement and said second securement, respectively.

13. The cardiac assist device of claim 12 further comprising a fluid supply in fluid communication with an interior of both said first secondary pumping element and said second secondary pumping element and at least one of: a single pump modifying a pressure of fluid in of both said first secondary pumping element and said second secondary pumping element with a periodicity to aid in blood movement through the vessel, or a transcutaneous energy transfer module modifying a pressure of fluid in of both said first inflatable cardiac pumping chamber and said second secondary pumping element with a periodicity to aid in blood movement through the vessel.

14. A process of implanting a cardiac device comprising:
inserting an expandable primary pumping element in mechanical communication with a securement within a vessel of a patient via an exovascular catheter;
creating an end-to-side anastomosis in a wall of a vessel at the location of said securement;
joining said expandable primary pumping with said securement within the vessel to a conduit external to the vessel, where said conduit is introduced into the patient via a percutaneous access device and is joined to said securement through the end-to-side anastomosis in the wall of the vessel; and
inserting a secondary pumping element into said expandable primary pumping element through said conduit via the percutaneous access device and through a wall of the vessel at the location of said securement.

15. The process of claim 14 wherein a securement device surrounding said conduit deploys staples for said joining step.

16. The process of claim 14 further comprising applying vacuum to at least one of said secondary pumping element or an interstitial space between said secondary pumping element and said expandable primary pumping element.

17. The process of claim 14 further comprising evaluating the wall of the vessel using prior optical coherence tomography to the creating of the end-to-side anastomosis.

18. The process of claim 14 further comprising inserting said primary pumping element exovascularly into said securement.

* * * * *